(12) United States Patent
Quertermous et al.

(10) Patent No.: US 7,041,801 B1
(45) Date of Patent: May 9, 2006

(54) ANTIBODIES BINDING TO POLYPEPTIDES ENCODED BY DEVELOPMENTALLY-REGULATED ENDOTHELIAL CELL LOCUS-1

(75) Inventors: Thomas Quertermous, Nashville, TN (US); Brigid Hogan, Brentwood, TN (US); H. Ralph Snodgrass, Powell, OH (US); Thomas Joel Zupancic, Worthington, OH (US)

(73) Assignees: Vanderbilt University; Valentis, Inc.

( * ) Notice: Subject to any disclaimer, the term of this patent is extended or adjusted under 35 U.S.C. 154(b) by 0 days.

(21) Appl. No.: 09/237,981

(22) Filed: Jan. 25, 1999

Related U.S. Application Data

(60) Division of application No. 08/659,235, filed on Jun. 5, 1996, now Pat. No. 5,877,281, which is a continuation-in-part of application No. 08/480,229, filed on Jun. 7, 1995, now Pat. No. 5,874,562.

(51) Int. Cl.
*C07K 16/00* (2006.01)

(52) U.S. Cl. .............................. 530/387.1; 530/387.3; 530/387.9; 530/388.2; 530/389.6

(58) Field of Classification Search ............. 530/387.1, 530/387.3, 387.9, 388.2, 389.6
See application file for complete search history.

(56) References Cited

U.S. PATENT DOCUMENTS

| | | | |
|---|---|---|---|
| 4,215,051 A | 7/1980 | Schroeder et al. | 260/346.7 |
| 4,868,112 A | 9/1989 | Toole, Jr. et al. | 435/68 |
| 4,946,778 A | 8/1990 | Ladner et al. | 435/69.6 |
| 5,096,825 A | 3/1992 | Barr et al. | 435/255 |
| 5,270,170 A | 12/1993 | Schatz et al. | 435/7.37 |
| 5,505,955 A | 4/1996 | Peterson et al. | 424/439 |
| 5,506,107 A | 4/1996 | Cunningham et al. | 435/7.21 |
| 5,508,199 A | 4/1996 | Gonzalez et al. | 435/320.1 |
| 6,168,946 B1 * | 1/2001 | Houghton et al. | 435/252.33 |

FOREIGN PATENT DOCUMENTS

| | | |
|---|---|---|
| WO | 94/11508 | 5/1994 |
| WO | 96/40769 | 12/1996 |

OTHER PUBLICATIONS

Allen et al., "Transgenes as probes for active chromosomal domains in mouse development," *Nature* 333:852-855 (1988).

Anderson, 1990, "Adhesion molecules and animal development," *Experentia* 46:2-13.

Aruffo et al., "CD44 is the principal cell surface receptor for hyaluronate," *Cell* 61:1303 (1990).

Ausubel et al.(editor), *Current Protocols in Molecular Biology*, John Wiley & Sons (1994) (Table of Contents for vols. 1 & 2).

Bevilacqua et al., "Endothelial leukocyte adhesion molecule 1: An inducible receptor for neutrophils related to complement regulatory proteins and lectins," *Science* 243:1160-1165 (1989).

Bevilacqua et al., "Selectins," *J. Clin. Invest.* 91:379-387 (1993).

Bhat et al., "Functional cloning of mouse chromosomal loci specifically active in embryonal carcinoma stem cells," *Mol. Cell. Biol.* 8:3251-3259 (1988).

Bisgrove et al., "The spEGF III gene encodes a member of the fibropellins: EGF repeat-containing proteins that form the apical lamina of the sea urchin embryo," *Develop. Biol.* 157:526-538 (1993).

Bitter et al., "Expression and secretion vectors for yeast," *Methods in Enzymology* 153:516-544 (1987).

Bitter, Heterologous Gene Expression in Yeast, *Methods in Enzymology* 152:673-684 (1987).

Breier et al., "Expression of vascular endothelial growth factor during embryonic angiogenesis and endothelial cell differentiation," *Development* 114:521-532 (1992).

Brisson et al., "Expression of a bacterial gene in plants by using a viral vector," *Nature* 310:511-514 (1984).

Broglie et al., "Light-regulated expression of a pea riboluse-1,5-biphosphate carboxylase small subunit gene in transformed plant cells," *Science* 224:838-843 (1984).

Brooks et al., 1994, "Integrin $\alpha_v\beta_3$ antagonists promote tumor regression by inducing apoptosis of angiogenic blood vessels," *Cell* 79:1157-1164.

(Continued)

*Primary Examiner*—Patrick J. Nolan
(74) *Attorney, Agent, or Firm*—Wong, Cabello, Lutsch, Rutherford & Brucculeri, LLP

(57) ABSTRACT

The present invention relates to a member of a novel gene family referred to as developmentally-regulated endothelial cell locus-1 (del-1). In particularly, the invention related to del-1 nucleotide sequences, Del-1 amino acid sequences, methods of expressing a functional gene product, and methods of using the gene and gene product. Since del-1 is expressed in endothelial cells and certain cancer cells, it may be useful as an endothelial cell and tumor marker. In addition, anti-Del-1 antibodies for immunological assessment of Del-1 protein expression as well as for inhibiting or stimulating Del-1 function are provided.

12 Claims, 33 Drawing Sheets

OTHER PUBLICATIONS

Figure 1:
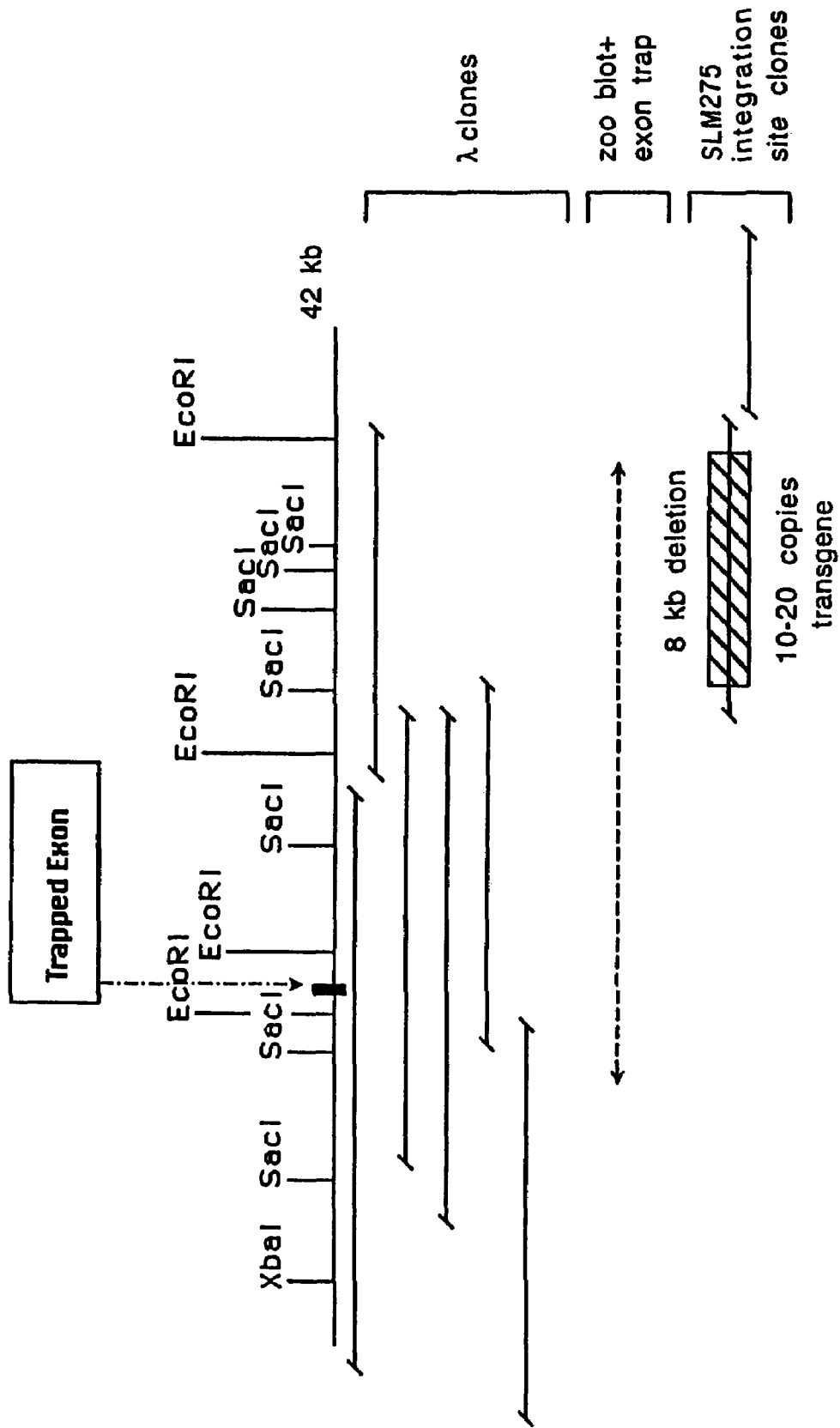

Broudy et al., "Interluekin 1 stimulates human endothelial cells to produce granulocyte-macrophage colony-stimulating factor and granulocyte colony-stimulating factor," *J. Immunol.* 139:464-468 (1987).

Caruthers et al., "New chemical methods for synthesizing polynucleotides," *Nuc. Acids Res. Symp. Ser.* 7:215-233 (1980).

Chow et al., "Synthesis of oligodeoxyribonucleotides on silica gel support," *Nuc. Acids Res.* 9(12):2807-2817 (1981).

Coffin et al., "Endothelial cell origin and migration in embryonic heart and cranial blood vessel development," *Anat. Rec.* 231:383-395 (1991).

Colberre-Garapin et al., "A new dominant hybrid selective maker for higher eukaryotic cells," *J. Mol. Biol.* 150:1-14 (1981).

Cole et al., "The EBV-Hybridoma technique and its application to human lung cancer," *Monoclonal Antibodies and Cancer Therapy* pp. 77-96 (1985).

Coruzzi et al., "Tissue-specific and light-regulated expression of a pea nuclear gene encoding the small subunit of riboluse-1, 5-bisphosphate carboxylase," *EMBO J.* 3:1671-1680 (1984).

Cote et al., "Generation of human monoclonal antibodies reactive with cellular antigens," *Proc. Natl. Acad. Sci.* 80:2026-2030 (1983).

Cotran et al., "Cytokine-endothelial interactions in inflammation, immunity, and vascular injury," *J. Am. Soc. Nephrol.* 1:225-235 (1990).

Couso et al., 1994, "Notch is required for wingless signaling in the epidermis of drosophila," Cell 79:259-272.

Crea et al., "Synthesis of oligonucleotides on cellulose by a phosphotriester method," *Nuc. Acids Res.* 9(10):2331-2348 (1980).

Creighton, *Proteins Structures and Molecular Principles*, W.H. Freeman and Co., N.Y. pp. 34-60 (1983).

Crowley et al., 1985, Phenocopy of discoidin I-minus mutants by antisense transformation in dictyostelium, Cell 43:633-641.

*Current Protocols in Molecular Biology*, vol. 2, Ed. Ausubel et al., Greene Publish. Associ. & Wiley Interscience, Ch. 13 (1988).

Del Amo et al., "Expression pattern of Motch, a mouse homolog of drosphila notch, suggests an important role in early postimplantation mouse development," *Development* 115:737-744 (1992).

Doolittle, "The genealogy of some recently evolved vertebrate proteins," *TIBS* pp. 233-237 (1985).

Dumont et al., "tek- a novel tyrosine kinase gene located on mouse chromosome 4, is expressed in endothelial cells and their presumptive precursors," *Oncogene* 7:1471-1480 (1992).

Dumont et al., "The endothelial-specific receptor tyrosine kinase, TEK, is a member of a new subfamily of receptors," Oncogene 8(5):1293-1301 (1993).

Durkin et al., "Amino acid sequence an domain structure of entactin. Homology with epidermal growth factor precursor and low density lipoprotein receptor," *J. Cell. Biol.* 107: 2749-2756 (1988).

Ekblom et al., "Role of mesenchymal nidogen for epithelial morphogenesis in vitro," *Development* 120:2003-2014 (1994).

Ellisen et al., "TAN-1, the human homolog of the drosphila notch gene, is broken by chromosomal translocations in T lymphoblastic neoplasms," *Cell* 66:649-661 (1991).

Engel, "EGF-like domains in extracellular matrix proteins: Localized signals for growth and differentiation," *FEBS Lett.* 251:1-7 (1989).

Familari et al., GenBank Accession No. L14608 (accessed Dec. 18, 1997) Jul. 14, 1993.

Fidler et al., "The implications of angiogenesis for the biology and therapy of cancer metastasis," *Cell* 79:185-188 (1994).

Folkman and Shing, "Angiogenesis," *J. Biol. Chem.* 267: 10931-10934 (1992).

Folkman et al., "Angiogenic factors," *Science* 235:442-447 (1987).

Fong et al., "Tumor progression and loss of heterozygosity at 5q and 18q in non-small cell lung cancer," *Cancer Res.* 55:220-223 (1995).

Fortini et al., 1994, "The suppressor of hairless protein participates in notch receptor signaling," Cell 79:273-282.

Francke, "Digitized and differentially shaded human chromosome ideograms for genomic applications," *Cytogenet. Cell Genet.* 65:206-219 (1994).

Frazier, "Thrombospondin: A modular adhesive glycoprotein of platelets and nucleated cells," *J. Cell. Biol.* 105:625 (1987).

Fukuzawa et al., 1988, "Monoclonia antibodies against discoidin I and discoidin II of the cellular slime mold Dictyosteium discoideum," J. Biochem 103:884-888.

Gimbrone et al., "Endothelial interleukin-8: A novel inhibitor of leukocyte-endothelial interactions," *Science* 246: 1601-1603 (1989).

Granger et al., "Molecular and cellular basis of myocardial angiogenesis," *Cell and Mol. Biol. Res.* 40:81-85 (1994).

Grierson et al., *Plant Molecular Biology* 2$^{nd}$ Ed. Blackie, London Ch. 7-9 (1988).

Gunning et al., "A Human β -actin Expression Vector System Directs High-level Accumulation of Antisense Transcripts," *Proc. Natl. Acad. Sci. USA* 84:4831-4835 (1987).

Gurley et al., "Upstream sequences required for efficient expression of a soybean heat shock gene," *Mol. Cell. Biol.* 6:559-565 (1986).

Harlow and Lane, *Antibody: A Laboratory Manual*, Cold Springs Harbor Laboratory (1988) (Table of Contents Only).

Hartman et al., "Two dominant-acting selectable markers for gene transfer studies in mammalian cells," *Proc. Natl. Acad. Sci.* 85:8047-8051 (1988).

Henderson et al., 1994, "Iag-2 may encode a signaling ligand for the GLP-1 and LIN-12 receptors of C. elegans," Development 120:2913-2924.

Hillier et al., GenBank Accession No. R56339 (accessed Dec. 18, 1997) May 23, 1995.

Hogan et al., *Manipulating the Mouse Embryo*, Cold Spring Harbor Press (1994) Table of Contents Only.

Hollenbaugh et al., "Construction of immunoglobulin fusion proteins," *Current Protocols in Immunology*, Unit 10.19 (1992).

Huse et al., "Generation of a large combinatorial library of the immunoglobulin repertoire in phage lambda," *Science* 246:1275-1281 (1989).

Hutter et al., "glp-1 and inductions establishing embryonic axes in C. elegans," *Development* 120:2051-2064 (1994).

Hynes, 1992, "Integrins: Versatility, modulation, and signaling in cell adhesion," Cell 69:11-25.

Inouye and Inouye, "Up-promotor mutations in the Ipp gene of *Escherichia coli*," *Nucleic Acids Research* 13(9):3100-3111 (1985).

Ishikawa et al., "Identification of angiogenic activity and the cloning and expression of platelet-derived endothelial cell growth factor," *Nature* 338:557-562 (1989).

Issekutz, "Lymphocyte homing to sites of inflammation," *Curr. Opin. Immunol.* 4:287-293 (1992).

Jackman et al., "Characterization of a thrombomodulin cDNA reveals structural similarity to the low density lipoprotein receptor," *Proc. Natl. Acad. Sci.* 83:8834-8838 (1986).

Janssens et al., "Cloning and expression of cDNA encoding human endothelium-derived relaxing factor/Nitric oxide synthase," *J. Biol. Chem.* 267:14519-14522 (1992).

Jenny et al., "Complete cDNA and derived amino acid sequence of human factor V," *Proc. Natl. Acad. Sci.* 84: 4846-4850 (1987).

Johnson et al, 1993, "A receptor tyrosine kinase found in breast carcinoma cells has an extracellular discoidin I-like domain," Proc. Natl. Acad. Sci. USA 90:5677-5681.

Kane et al., 1986, "Cloning of a cDNA coding for human factor V, a blood coagulation factor homologous to factor VIII and ceruloplasmin," PNAS 83:6800-6804.

Karls et al., "Structure, expression, and chromosome location of the gene for the β subunit of brain-specific $Ca^{2+}$/calmodulin-dependent protein kinase II identified by transgene integration in an embryonic lethal mouse mutant," *Mol. Cell. Biol.* 12:3644-3652 (1992).

Keck et al., "Vascular permeability factor, an endothelial cell mitogen related to PDGF," *Science* 246:1309-1312 (1989).

Kohler et al., "Continuous cultures of fused cells secreting antibody of predefined specificity," *Nature* 256:495-497 (1975).

Kothary et al., "A transgene containing lacZ inserted into the dystonia locus is expressed in neural tube," *Nature* 335:435-437 (1988).

Kozbor et al., "The production of monoclonal antibodies from human lymphocytes," *Immunology Today* 4:72-79 (1983).

Kronmiller et al., 1991, "EGF antisense oligodeoxynucleotides block murine odontogenesis in vitro," *Dev. Biol.* 147:485-488.

Lam et al., "A new type of synthetic peptide library for identifying ligand-binding activity," *Nature* 354:82-84 (1991).

Lamas et al., "Endothelial nitric oxide synthase: Molecular cloning and characterization of a distinct constitutive enzyme isoform," *Proc. Natl. Acad. Sci.* 89:6348-6352 (1992).

Larocca et al., 1991 "AM, 46,000 human milk fat globule protein that is highly expressed in human breast tumors contains factor VIII-like domains," Cancer Res. 51:4994-4998.

Lawler et al., "The structure of human thrombospondin, an adhesive glycoprotein with multiple calcium-binding sites and homologies with several different proteins," *J. Cell. Biol.* 103:1635-1648 (1986).

Leung et al., "Vascular endothelial growth factor is a secreted angiogenic mitogen," *Science* 246:1306-1309 (1989).

Locksley et al., "Tumor necrosis factors α and differ β differ in their capacities to generate interleukin 1 release from human endothelial cells," *J. Immunol.* 139:1891-1895 (1987).

Logan et al., "Adenovirus tripartite leader sequence enhances translation of mRNAs late after infection," *Proc. Natl. Acad. Sci.* 81:3655-3659 (1984).

Loppnow et al., "Comparative analysis of cytokine induction in human vascular endothelial and smooth muscle cells," *Lymphokine. Res.* 8:293-299 (1989).

Lowy et al., "Isolation of transforming DNA: Cloning the hamster aprt gene," *Cell* 22:817-823 (1980).

Luscher et al., "Endothelium-derived contracting factors," *Hypertension* 19:117-130 (1992).

Mackett et al., "General method for production and selection of infectious vaccinia virus recombinants expressing foreign genes," *J. Virol.* 49:857-864 (1984).

Mackett et al., "Vaccinia virus: A selectable eukaryotic cloning and expression vector," *Proc. Natl. Acad. Sci.* 79: 7415-7419 (1982).

Main et al., 1992, "The three-dimensional structure of the tenth type III module of fibronectin: An insight into RGD-mediated interactions," Cell 71:671-678.

Mantovani et al., "Cytokine regulation of endothelial cell function," *FASEB J.* 6:2591-2599 (1992).

Matteucci et al., "The synthesis of oligodeoxyprimidines on a polymer support," *Tetrahedron Letter* 21:719-722 (1980).

McConlogue, "Amplification and expression of heterologous ornithine decarboxylase in chinese hamster cells," *In:Current Communications in Molecular Biology*, Cold Spring Harbor Laboratory, pp. 79-87 (1987).

Millauer et al., "High affinity VEGF binding and developmental expression suggest Flk-1 as a major regulator of vasculogenesis and angiogenesis," *Cell* 72:835-846 (1993).

Morrison et al., "Chimeric human antibody molecules: Mouse antigen-binding domains with human constant region domains," *Proc. Natl. Acad. Sci.* 81:6851-6855 (1984).

Mulligan et al., "Selection for animal cells that express the *Escherichia coli* gene coding for xanthine-guanine phosphoribosyltransferase," *Proc. Natl. Acad. Sci.* 78:2072-2076 (1981).

Nabel et al., "Gene transfer Into vascular cells," *J. Am. Coll. Cardiol.* 17:189B-194B (1991).

Neuberger et al., "Recombinant antibodies possessing novel effector functions," *Nature* 312:604-608 (1984).

Noden, "Embryonic origins and assembly of blood vessels," *Am. Rev. Respir. Dis.* 140:1097-1103 (1989).

Noden, "Origins and patterning of avian outflow tract endocardium," *Development* 111:867-876 (1991).

Nomura et al. "Evidence for positive and negative regulatory elements in the 5'-flanking sequence of the mouse sparc (osteonectin) gene,"*J. Biol. Chem.* 264:12201-12207 (1989).

O'Hare et al., "Transformation of mouse fibroblasts to methotrexate resistance by a recombinant plasmid expessing a prokaryotic dihydrofolate reductase,"*Proc. Natl. Acad. Sci.*, 78:1527-1531 (1981).

O'Kane et al., "Detection in situ of genomic regulatory elements in drosophila," *Proc. Natl. Acad. Sci,* 84:9123-9127 (1987).

O'Reilly et al., "Angiostatin: A novel angiogenesis inhibitor that mediates the suppression of metastases by a Lewis Lung Carcinoma," *Cell* 79:315-328 (1994).

Orsini et al., 1991, "Radioimmunoassay of epidermal growth factor in human saliva and gastic juice," Clinical Biochem 24:135-141.

Osborn et al., "Direct expression cloning of vascular cell adhesion molecule 1, a cytokine-induced endothelial protein that binds to lymphocytes," *Cell* 59:1203-1211 (1989).

Panicali et al., "Construction of poxviruses as cloning vectors: Insertion of the tyhmidine kinases gene from herpes simplex virus into the DNA of infectious vaccinia virus," *Proc. Natl. Acad. Sci.* 79:4927-4931 (1982).

Pardanaud et al., "Relationship between vasculogenesis, angiogenesis and haemopoiesis during avian ontogeny," *Development* 105:473-485 (1989).

Pepper et al., "Chondrocytes inhibit endothelial sprout formation in vitro: Evidence for involvement of a transforming growth factor-beta," *J. Cell. Physiol.* 146:170-179 (1991).

Poole et al., "Sequence and expression of the discoidin I gene family in dictyostelium discoideum," *J. Mol. Biol.* 153:273-289 (1981).

Potts et al., "Epithelial-mesenchymal transformation of embryonic cardiac endothelial cells is inhibited by a modified antisense oligodeoxynucleotide to transforming growth factor β3," *Proc. Natl. Acad. Sci.* 88:1516-1520 (1991).

Quertermous el al., "Cloning and characterization of a basic helix-loop-helix protein expressed in early mesoderm and the developing somites," *Proc. Natl. Acad. Sci.* 91:7066-7070 (1994).

Raines et al., "Smooth muscle cells and the pathogenesis of the lesions of atherosclerosis," *Br. Heart J.* 69:S30-S37 (1993).

Reaume et al., "Expesion analysis of a notch homologue in the mouse embryo," *Develop. Biol.* 154:377-387 (1992).

Rebay et al., 1991, "Specific EGF repeats of notch mediate interactions with delta and serrate: Implications for notch as a multifunctional receptor, " *Cell* 67:687-699.

Reddy et al., GenBank Accession No. T09857 (accessed Dec. 18, 1997) Nov. 29, 1993.

Risau et al., "Endothelial cell growth factors in embryonic and adult chick brain are related to human acidic fibroblast growth factor, " *EMBO J.* 7:959-962 (1988).

Rogers et al., "Gene transfer in plants: Production of transformed plants using ti plasmid vectors," *Methods for Plant Molecular Biology* Ed. Weissbach & Weissbach, Academic Press, N.Y. Section VIII, pp. 421-463 (1988).

Rothstein, "Ch. 3: Cloning in Yeast," *DNA Cloning* vol. II, Ed. Glover, IRL Press, Wash. D.C. (1986).

Ruther and Muller-Hill, "Easy identification of cDNA clones," *EMBO J.* 2(10):1791-1794 (1983).

Sambrook et al., *Molecular Cloning: A Laboratory Manual*, $2^{nd}$ *Edition*, Cold Spring Harbor Laboratory Press (1989) (Table of Contents—All Three Volumes).

Santerre et al., "Expression of prokaryotic genes for hygromycin B and G418 resistance as dominant-selection markers in mouse L cells," *Gene* 30:147-156 (1984).

Seelentag et al., "Additive effects of interleukin 1 and tumour necrosis factor-α on the accumulation of the three granulocyte and macrophage colony-stimulating factor mRNAs in human endothelial cells," *EMBO J.* 6:2261-2265 (1987).

Sinning et al., "Multiple glycoproteins localize to a particulate form of extracellular matrix in regions of the embryonic heart where endothelial cells transform into mesenchyme," *Anat. Rec.* 232:285-292 (1992).

Smith et al., "Molecular engineering of the *Autographa californica* nuclear polyhedrosis virus genome: Deletion mutations within the polyhedrin gene," *J. Viol.* 46:584-593 (1983).

Soininen et al., "The mouse Enhancer trap locus 1 (Etl-1): A novel mammalian gene related to drosophila and yeast transcriptional regulatory genes," *Mechanisms of Development* 39:111-123 (1992).

Staunton et al., "Functional cloning of ICAM-2, a cell adhesion ligand for LFA-1 homologous to ICAM-1," *Nature* 339:61-64 (1989).

Staunton et al., "Primary structure of ICAM-1 demonstrates interaction between members of the immunoglobulin and integrin supergene families," *Cell* 52:925-933 (1988).

Stubbs et al., 1990, "cDNA cloning of a mouse mammary epithelial cell surface protein reveals the existence of epidermal growth factor-like sequences," PNAS 87:8417-8421.

Szybalska et al., "Genetics of human cell lines, IV. DNA-mediated heritable transformation of a biochemical trait," *Proc. Natl. Acad. Sci.* 48:2026-2034 (1962).

Takagi et al., "The A5 antigen, a candidate for the neuronal recognition molecule, has homologies to complement components and coagulation factors," *Neuron* 7:295-307 (1991).

Takamatsu et al., "Expression of bacterial chloramphenicol acetylransferase gene in tobacco plants mediated by TMV-RNA," *EMBO J.* 6:307-311 (1987).

Takeda et al., "Construction of chimaeric processed immunoglobulin genes containing mouse variable and human constant region sequences," *Nature* 314:452-454 (1985).

Taraboletti et al., "Platelet thrombospondin modulates endothelial cell adhesion, motility, and growth: A potential angiogenesis regulatory factor," *J. Cell. Biol.* 111:765-772 (1990).

Toole et al., "Molecular cloning of a cDNA encoding human antihaemophilic factor," *Nature* 312:342-347 (1984).

Van Heeke and Schuster, "Expression of Human Asparagine Synthetase in *Escherichia coli,"* *J. Biol. Chem.* 264(10): 5503-5509 (1989)

Vogel et al., "Apolipoprotein E: A potent inhibitor of endothelial and tumor cell proliferation," *J. Cell. Biochem.* 54:299-308 (1994).

Vu et al., "Molecular cloning of a functional thrombin receptor reveals a novel proteolytic mechanism of receptor activation," *Cell* 64:1057-1068 (1991).

Warner et al., "Interleukin 1 induces interleukin 1: II. Recombinant human interleukin 1 induces interleukin 1 production by adult human vascular endothelial cells," *J. Immunol.* 139:1911-1917 (1987).

Wei et al., "Directed endothelial differentiation of cultured embryonic yolk sac cells in vivo provides a novel cell-based system for gene therapy," *Stem Cell* 13:541-547 (1995).

Wieland et al., "Allelic deletion mapping on chromosome 5 in human lung carcinomas," *Oncogene* 12:97-102 (1996).

Wieland et al., "Frequent allelic deletion at a novel locus on chromosome 5 in human lung cancer," *Cancer Res.* 54: 1772-1774 (1994).

Wigler et al., "Transfer of purified herpes virus thymidine kinase gene to cultured mouse cells," *Cell* 11:223-232 (1977).

Wigler et al., "Transformation of mammalian cells with an amplifiable dominant-acting gene," *Proc. Natl. Acad. Sci.* 77:3567-3570 (1980).

Williams et al., "Adhesion molecules involved in the microvascular inflammatory response," *Am. Rev. Respir. Dis.* 146:S45-S50 (1992).

Woychik et al., "'Formins': proteins deduced from the alternative transcripts of the limb deformity gene," *Nature* 346:850-853 (1990).

Wu et al., "Deduced amino acid sequence of mouse blood-coagulation factor IX," *Gene* 86:275-278 (1990).

Yamaguchi et al., "flk-1, an flt-related receptor tyrosine kinase is an early marker for endothelial cell precursors," *Development* 118:489-498 (1993).

Yanagisawa et al., "A novel potent vasoconstrictor peptide produced by vascular endothelial cells," *Nature* 332:411-415 (1988).

* cited by examiner

```
SEQ ID NO:1 m-del1     DLLVPTKVTG IITQG---AKD FGDVLFVGSY KLAYSNDGEH WMVHQDEKQR cont.
SEQ ID NO:2 h-MFG      DLGSSKEVTG IITQG---ARN FGSVQFVASY KVAYSNDSAN WTEYQDPRTG cont.
SEQ ID NO:3 h-FV       DLLKIKKITA IITQG---CKS LSSEMYVKSY TIHYSEQGVE WKPYRLKSSM cont.
SEQ ID NO:4 m-FV111    DLQKTMKVTG IITQG---VKS LFTSMFVKEF LISSSQDGHH WT--QILYNG cont.
SEQ ID NO:5 X-A5b1     DLENLRFVSG IGTQGAISKE TKKKYFVKSY KVDISSNGED WI-TLKDGN  cont.
SEQ ID NO:6 X-A5b2     DLAEEKIVRG VIIQG---GKH KENKVFMRKF KIGYSNNGTE WEMIMDSSKN cont.
SEQ ID NO:7 dis-1      GCEVPRTFMC VALQC----RG -DADQWTSY  KIRYSLDNVS WF-----EYR cont.
SEQ ID NO:8 CONSENSUS  DL......VTG IITQG----K.  .....FV.SY KI.YS.DG.. W.........  cont.

SEQ ID NO:1 m-del1     KDKVFQGNFD NDTHRKNVID PPIYARFIRI LPL--
SEQ ID NO:2 h-MFG      SSKVFQGNLD NNSHKKNIFE KPFMARYVRV LPV--
SEQ ID NO:3 h-FV       VDKIFEGNTN TKGHVKNFFN PPIISRFIRV IPK--
SEQ ID NO:4 m-FV111    KVKVFQGNQD SSTPMMNSLD PPLLTR----- -----
SEQ ID NO:5 X-A5b1     KHLVFTGNTD ATDVVYRPFS KPVITRFVRL RPVTW
SEQ ID NO:6 X-A5b2     KPKTFEGNTN YDTPELRTF- AHITTGFIRI IP---
SEQ ID NO:7 dis-1      NGAAITGVTD RNTVVNHFFD TPIRARSIAI HPLT-
SEQ ID NO:8 CONSENSUS  K.KVF.GNTD ..T...N.F. .PI..RFIR. .P.

FIG. 2
```

```
        EcoRI       Hpal
         ▼           ▼
     GAATTCCGGT TAACTGAGGA CAAAGGGTAA TGCAGAAGTG ATATTTGATT TCCATTCTCA    60

Dral
                               ▼
     TTCCCAGTGG CCTTGATATT TAAACTGATT CCTGCCACCA GGTCCTTGGG CCACCCTGTC   120

EspBI        SphI
                     ▼            ▼
     CCTGCGTCTC ATATTTCTGC ATGCTGCTTT GTTTGTATAT AGTGCGCTCC TGGCCTCAGG   180

CTCGCTCCCC TCCAGCTCTC GCTTCATTGT TCTCCAAGTC AGAAGCCCCC GCATCCGCCG   240

BssHII
                                                              ▼
     CGCAGCAGCG TGAGCCGTAG TCACTGCTGG CCGCTTCGCC TGCCTGCGCG CACGGAAATC   300

GGGGAGCCAG GAACCCAAGG AGCCGCCGTC CGCCCGCTGT GCCTCTGCTA GACCACTCGC   360

AGCCCCAGCC TCTCTCAAGC GCACCCACCT CCGCGCACCC CAGCTCAGGC GAAGCTGGAG   420

TGAGGGTGAA TCACCCTTTC TCTAGGGCCA CCACTCTTTT ATCGCCCTTC CCAAGATTTG   480

Eco47III         AatII
          ▼                ▼
     AGAAGCGCTG CGGGAGGAAA GACGTCCTCT TGATCTCTGA CAGGGCGGGG TTTACTGCTG   540

BssHIII
           PstI
            ▼▼
     TCCTGCAGGC GCGCCTCGCC TACTGTGCCC TCCGCTACGA CCCCGGACCA GCCCAGGTCA   600

BspHI
                    ▼
     CGTCCGTGAG AAGGGATCAT GAAGCACTTG GTAGCAGCCT GGCTTTTGGT TGGACTCAGC   660
                          M   K   H   L   V   A   A   W   L   L   V   G   L   S

CTCGGGGTGC CCCAGTTCGG CAAAGGTGAC ATTTGCAACC CGAACCCCTG TGAAAATGGT   720
     L   G   V   P   Q   F   G   K   G   D   I   C   N   P   N   P   C   E   N   G
```

FIG.3A

```
                                                              BspMI
                                                               ▼
GGCATCTGTC TGTCAGGACT GGCTGATGAT TCCTTTTCCT GTGAGTGTCC AGAAGGCTTC 780
 G  I  C  L  S  G  L  A  D  D  S  F  S  C  E  C  P  E  G  F
                                                              BspMI
                                                               ▼
GCAGGTCCGA ACTGCTCTAG TGTTGTGGAG GTTGCATCAG ATGAAGAAAA GCCTACTTCA 840
 A  G  P  N  C  S  S  V  V  E  V  A  S  D  E  E  K  P  T  S

GCAGGTCCCT GCATCCCTAA CCCATGCCAT AACGGAGGAA CCTGTGAGAT AAGCGAAGCC 900
 A  G  P  C  I  P  N  P  H  N  G  G  T  C  E  I  S  E  A

TATCGAGGAG ACACATTCAT AGGCTATGTT TGTAAATGTC CTCGGGGATT TAATGGGATT 960
 Y  R  G  D  T  F  I  G  Y  V  C  K  C  P  R  G  F  N  G  I

CACTGTCAGC ACAATATAAA TGAATGTGAA GCTGAGCCTT GCAGAAATGG CGGAATATGT 1020
 H  C  Q  H  N  I  N  E  C  E  A  E  P  C  R  N  G  G  I  C

BsmI
                              ▼
ACCGACCTTG TTGCTAACTA CTCTTGTGAA TGCCCAGGAG AATTTATGGG ACGAAATTGT 1080
 T  D  L  V  A  N  Y  S  C  E  C  P  G  E  F  M  G  R  N  C

CAATATAAAT GCTCTGGGCA CTTGGGAATC GAAGGTGGGA TCATATCTAA TCAGCAAATC 1140
 Q  Y  K  C  S  G  H  L  G  I  E  G  G  I  S  N  Q  Q  I

SacI
              EclI36II
               ▼
ACAGCTTCAT CTAATCACCG AGCTCTTTTT GGACTCCAGA AGTGGTATCC CTACTATGCT 1200
 T  A  S  S  N  H  R  A  L  F  G  L  Q  K  W  Y  P  Y  Y  A

NcoI
                                                              MscI
                              PvuII                           BalI
                               ▼                               ▼
CGACTTAATA AGAAGGGCCT TATAAATGCC TGGACAGCTG CTGAAAATGA CAGATGGCCA 1260
 R  L  N  K  K  G  L  I  N  A  W  T  A  A  E  N  D  R  W  P

TGGATTCAGA TAAATTTGCA AAGAAAAATG AGAGTCACTG GTGTTATTAC CCAAGGAGCA 1320
 W  I  Q  I  N  L  Q  R  K  M  R  V  T  G  V  I  T  Q  G  A

AAAAGGATTG GAAGCCCAGA GTACATAAAA TCCTACAAAA TTGCCTACAG CAATGACGGG 1380
 K  R  I  G  S  P  E  Y  I  K  S  Y  K  I  A  Y  S  N  D  G
```

FIG.3B

```
                Bbs I                        Ear I
                  ▼                            ▼
AAGACCTGGG CAATGTACAA AGTAAAAGGC ACCAATGAAG AGATGGTCTT TCGTGGAAAT 1440
 K  T  W  A  M  Y  K  V  K  G  T  N  E  E  M  V  F  R  G  N

Nde I
                            ▼
GTTGATAACA ACACACCATA TGCTAATTCT TTCACACCCC CAATCAAAGC TCAGTATGTA 1500
 V  D  N  N  T  P  Y  A  N  S  F  T  P  P  I  K  A  Q  Y  V

AGACTCTACC CCCAAATTTG TCGAAGGCAT TGTACTTTAA GAATGGAACT TCTTGGCTGT 1560
 R  L  Y  P  Q  I  C  R  R  H  C  T  L  R  M  E  L  L  G  C

Sac I
  Ecl136II
  ▼▼
GAGCTCTCAG GCTGTTCAGA ACCTTTGGGG ATGAAATCAG GCATATACA AGACTACCAG 1620
 E  L  S  G  C  S  E  P  L  G  M  K  S  G  H  I  Q  D  Y  Q

Bbs I
             ▼
ATCACTGCCT CCAGCGTCTT CAGAACACTC AACATGGACA TGTTTACTTG GGAACCAAGG 1680
 I  T  A  S  S  V  F  R  T  L  N  M  D  M  F  T  W  E  P  R

AAAGCCAGGC TGGACAAGCA AGGCAAAGTA AATGCCTGGA CTTCCGGCCA TAACGACCAG 1740
 K  A  R  L  D  K  Q  G  K  V  N  A  W  T  S  G  H  N  D  Q

TCACAATGGT TACAGGTTGA TCTTCTTGTC CCTACTAAGG TGACAGGCAT CATTACACAA 1800
 S  Q  W  L  Q  V  D  L  L  V  P  T  K  V  T  G  I  I  T  Q

Pml I
                                     ▼
GGAGCTAAAG ATTTTGGTCA CGTGCAGTTT GTTGGGTCAT ACAAACTAGC TTACAGCAAT 1860
 G  A  K  D  F  G  H  V  Q  F  V  G  S  Y  K  L  A  Y  S  N

ApaL I
                   ▼
GATGGAGAAC ACTGGATGGT GCACCAGGAT GAAAAACAGA GGAAAGACAA GGTTTTTCAA 1920
 D  G  E  H  W  M  V  H  Q  D  E  K  Q  R  K  D  K  V  F  Q

GGCAATTTTG ACAATGACAC TCACAGGAAA AATGTCATCG ACCCTCCCAT CTATGCACGA 1980
 G  N  F  D  N  D  T  H  R  K  N  V  I  D  P  P  I  Y  A  R
```

FIG. 3C

```
TTCATAAGAA TCCTTCCTTG GTCCTGGTAT GGAAGGATCA CTCTGCGGTC AGAGCTGCTG 2040
 F  I  R  I  L  P  W  S  W  Y  G  R  I  T  L  R  S  E  L  L

Fspl
          ▼
GGCTGCGCAG AGGAGGAATG AAGTGCGGGG CCGCACATCC CACAATGCTT TTCTTTATTT 2100
 G  C  A  E  E  E

TCCTATAAGT ATCTCCACGA AATGAACTGT GTGAAGCTGA TGGAAACTGC ATTTGTTTTT 2160

HindIII
                                                  ▼
TTCAAAGTGT TCAAATTATG GTAGGCTACT GACTGTCTTT TTAGGAGTTC TAAGCTTGCC 2220

TTTTTAATAA TTTAATTTGG TTTCCTTTGC TCAACTCTCT TATGTAATAT CACACTGTCT 2280

Earl
          ▼
GTGAGTTACT CTTCTTGTTC TCT                                    2303
```

FIG.3D

```
                 9              18              27              36              45              54
5' TCT CTT TAG TCA CCA CTC TCG CCC TCT CCA AGA ATT TGT TTA ACA AAG GCG TGA
   --- --- --- --- --- --- --- --- --- --- --- --- --- --- --- --- --- ---
    S   L   *   S   P   L   S   P   S   P   R   I   C   L   T   K   R   *
                63              72              81              90              99             108
   GGA AAG AGA ACG TCT TCT TGA ATT CTT TAG TAG GGG CGG AGT CTG CTG CTG CCC
   --- --- --- --- --- --- --- --- --- --- --- --- --- --- --- --- --- ---
    G   K   R   T   S   S   *   I   L   *   *   G   R   S   L   L   L   P
               117             126             135             144             153             162
   TGC GCT GCC ACC TCG GCT ACA CTG CCC TCC GCG ACG ACC CCT GAC CAG CCG GGG
   --- --- --- --- --- --- --- --- --- --- --- --- --- --- --- --- --- ---
    C   A   A   T   S   A   T   L   P   S   A   T   T   P   D   Q   P   G
               171             180             189             198             207             216
   TCA CGT CCG GGA GAC GGG ATC ATG AAG CGC TCG GTA GCC GTC TGG CTC TTG GTC
   --- --- --- --- --- --- --- --- --- --- --- --- --- --- --- --- --- ---
    S   R   P   G   D   G   I   M   K   R   S   V   A   V   W   L   L   V
               225             234             243             252             261             270
   GGG CTC AGC CTC GGT GTC CCC CAG TTC GGC AAA GGT GAT ATT TGT GAT CCC AAT
   --- --- --- --- --- --- --- --- --- --- --- --- --- --- --- --- --- ---
    G   L   S   L   G   V   P   Q   F   G   K   G   D   I   C   D   P   N
               279             288             297             306             315             324
   CCA TGT GAA AAT GGA GGT ATC TGT TTG CCA GGA TTG GCT GTA GGT TCC TTT TCC
   --- --- --- --- --- --- --- --- --- --- --- --- --- --- --- --- --- ---
    P   C   E   N   G   G   I   C   L   P   G   L   A   V   G   S   F   S
               333             342             351             360             369             378
   TGT GAG TGT CCA GAT GGC TTC ACA GAC CCC AAC TGT TCT AGT GTT GTG GAG GTT
   --- --- --- --- --- --- --- --- --- --- --- --- --- --- --- --- --- ---
    C   E   C   P   D   G   F   T   D   P   N   C   S   S   V   V   E   V
               387             396             405             414             423             432
   GCA TCA GAT GAA GAA GAA CCA ACT TCA GCA GGT CCC TGC ACT CCT AAT CCA TGC
   --- --- --- --- --- --- --- --- --- --- --- --- --- --- --- --- --- ---
    A   S   D   E   E   E   P   T   S   A   G   P   C   T   P   N   P   C
               441             450             459             468             477             486
   CAT AAT GGA GGA ACC TGT GAA ATA AGT GAA GCA TAC CGA GGG GAT ACA TTC ATA
   --- --- --- --- --- --- --- --- --- --- --- --- --- --- --- --- --- ---
    H   N   G   G   T   C   E   I   S   E   A   Y   R   G   D   T   F   I
               495             504             513             522             531             540
   GGC TAT GTT TGT AAA TGT CCC CGA GGA TTT AAT GGG ATT CAC TGT CAG CAC AAC
   --- --- --- --- --- --- --- --- --- --- --- --- --- --- --- --- --- ---
    G   Y   V   C   K   C   P   R   G   F   N   G   I   H   C   Q   H   N
               549             558             567             576             585             594
   ATA AAT GAA TGC GAA GTT GAG CCT TGC AAA AAT GGT GGA ATA TGT ACA GAT CTT
   --- --- --- --- --- --- --- --- --- --- --- --- --- --- --- --- --- ---
    I   N   E   C   E   V   E   P   C   K   N   G   G   I   C   T   D   L
               603             612             621             630             639             648
   GTT GCT AAC TAT TCC TGT GAG TGC CCA GGC GAA TTT ATG GGA AGA AAT TGT CAA
   --- --- --- --- --- --- --- --- --- --- --- --- --- --- --- --- --- ---
    V   A   N   Y   S   C   E   C   P   G   E   F   M   G   R   N   C   Q
```

FIG. 4A

```
          657              666             675             684             693             702
TAC AAA TGC TCA GGC CCA CTG GGA ATT GAA GGT GGA ATT ATA TCA AAC CAG CAA
--- --- --- --- --- --- --- --- --- --- --- --- --- --- --- --- --- ---
 Y   K   C   S   G   P   L   G   I   E   G   G   I   I   S   N   Q   Q
          711              720             729             738             747             756
ATC ACA GCT TCC TCT ACT CAC CGA GCT CTT TTT GGA CTC CAA AAA TGG TAT CCC
--- --- --- --- --- --- --- --- --- --- --- --- --- --- --- --- --- ---
 I   T   A   S   S   T   H   R   A   L   F   G   L   Q   K   W   Y   P
          765              774             783             792             801             810
TAC TAT GCA CGT CTT AAT AAG AAG GGG CTT ATA AAT GCG TGG ACA GCT GCA GAA
--- --- --- --- --- --- --- --- --- --- --- --- --- --- --- --- --- ---
 Y   Y   A   R   L   N   K   K   G   L   I   N   A   W   T   A   A   E
          819              828             837             846             855             864
AAT GAC AGA TGG AAC CGG TGG ATT CAG ATA AAT TTG CAA AGA AAA ATG AGA GTT
--- --- --- --- --- --- --- --- --- --- --- --- --- --- --- --- --- ---
 N   D   R   W   N   R   W   I   Q   I   N   L   Q   R   K   M   R   V
          873              882             891             900             909             918
ACT GGT GTG ATT ACC CAA GGG GCC AAG AGG ATT GGA AGC CCA GAG TAT ATA AAA
--- --- --- --- --- --- --- --- --- --- --- --- --- --- --- --- --- ---
 T   G   V   I   T   Q   G   A   K   R   I   G   S   P   E   Y   I   K
          927              936             945             954             963             972
TTC TAC AAA ATT GCC TAC AGT AAT GAT GGA AAG ACT TGG GCA ATG TAC AAA GTG
--- --- --- --- --- --- --- --- --- --- --- --- --- --- --- --- --- ---
 F   Y   K   I   A   Y   S   N   D   G   K   T   W   A   M   Y   K   V
          981              990             999            1008            1017            1026
AAA GGC ACC AAT GAA GAC ATG GTG TTT CGT GGA AAC ATT GAT AAC AAC ACT CCA
--- --- --- --- --- --- --- --- --- --- --- --- --- --- --- --- --- ---
 K   G   T   N   E   D   M   V   F   R   G   N   I   D   N   N   T   P
         1035             1044            1053            1062            1071            1080
TAT GCT AAC TCT TTC ACA CCC CCC ATA AAA GCT CAG TAT GTA AGA CTC TAT CCC
--- --- --- --- --- --- --- --- --- --- --- --- --- --- --- --- --- ---
 Y   A   N   S   F   T   P   P   I   K   A   Q   Y   V   R   L   Y   P
         1089             1098            1107            1116            1125            1134
CAA GTT TGT CGA AGA CAT TGC ACT TTG CGA ATG GAA CTT CTT GGC TGT GAA CTG
--- --- --- --- --- --- --- --- --- --- --- --- --- --- --- --- --- ---
 Q   V   C   R   R   H   C   T   L   R   M   E   L   L   G   C   E   L
         1143             1152            1161            1170            1179            1188
TCG GGT TGT TCT GAG CCT CTG GGT ATG AAA TCA GGA CAT ATA CAA GAC TAT CAG
--- --- --- --- --- --- --- --- --- --- --- --- --- --- --- --- --- ---
 S   G   C   S   E   P   L   G   M   K   S   G   H   I   Q   D   Y   Q
         1197             1206            1215            1224            1233            1242
ATC ACT GCC TCC AGC ATC TTC AGA ACG CTC AAC ATG GAC ATG TTC ACT TGG GAA
--- --- --- --- --- --- --- --- --- --- --- --- --- --- --- --- --- ---
 I   T   A   S   S   I   F   R   T   L   N   M   D   M   F   T   W   E
         1251             1260            1269            1278            1287            1296
CCA AGG AAA GCT CGG CTG GAC AAG CAA GGC AAA GTG AAT GCC TGG ACC TCT GGC
--- --- --- --- --- --- --- --- --- --- --- --- --- --- --- --- --- ---
 P   R   K   A   R   L   D   K   Q   G   K   V   N   A   W   T   S   G
```

FIG. 4B

```
      1305          1314          1323          1332          1341          1350
CAC AAT GAC CAG TCA CAA TGG TTA CAG GTG GAT CTT CTT GTT CCA ACC AAA GTG
--- --- --- --- --- --- --- --- --- --- --- --- --- --- --- --- --- ---
 H   N   D   Q   S   Q   W   L   Q   V   D   L   L   V   P   T   K   V
      1359          1368          1377          1386          1395          1404
ACT GGC ATC ATT ACA CAA GGA GCT AAA GAT TTT GGT CAT GTA CAG TTT GTT GGC
--- --- --- --- --- --- --- --- --- --- --- --- --- --- --- --- --- ---
 T   G   I   I   T   Q   G   A   K   D   F   G   H   V   Q   F   V   G
      1413          1422          1431          1440          1449          1458
TCC TAC AAA CTG GCT TAC AGC AAT GAT GGA GAA CAC TGG ACT GTA TAC CAG GAT
--- --- --- --- --- --- --- --- --- --- --- --- --- --- --- --- --- ---
 S   Y   K   L   A   Y   S   N   D   G   E   H   W   T   V   Y   Q   D
      1467          1476          1485          1494          1503          1512
GAA AAG CAA AGA AAA GAT AAG GTT TTC CAG GGA AAT TTT GAC AAT GAC ACT CAC
--- --- --- --- --- --- --- --- --- --- --- --- --- --- --- --- --- ---
 E   K   Q   R   K   D   K   V   F   Q   G   N   F   D   N   D   T   H
      1521          1530          1539          1548          1557          1566
AGA AAA AAT GTC ATC GAC CCT CCC ATC TAT GCA CGA CAC ATA AGA ATC CTT CCT
--- --- --- --- --- --- --- --- --- --- --- --- --- --- --- --- --- ---
 R   K   N   V   I   D   P   P   I   Y   A   R   H   I   R   I   L   P
      1575          1584          1593          1602          1611          1620
TGG TCC TGG TAC GGG AGG ATC ACA TTG GCG TCA GAG CTG CTG GGC TGC ACA GAG
--- --- --- --- --- --- --- --- --- --- --- --- --- --- --- --- --- ---
 W   S   W   Y   G   R   I   T   L   A   S   E   L   L   G   C   T   E
      1629          1638          1647          1656          1665          1674
GAG GAA TGA GGG GAG GCT ACA TTT CAC AAC CGT CTT CCC TAT TTG GGT AAA AGT
--- --- --- --- --- --- --- --- --- --- --- --- --- --- --- --- --- ---
 E   E   *   G   E   A   T   F   H   N   R   L   P   Y   L   G   K   S
      1683          1692          1701          1710          1719          1728
ATC TCC ATG GAA TGA ACT GTG TAA AAT CTG TAG GAA ACT GAA TGG TTT TTT TTT
--- --- --- --- --- --- --- --- --- --- --- --- --- --- --- --- --- ---
 I   S   M   E   *   T   V   *   N   L   *   E   T   E   W   F   F   F
      1737          1746          1755          1764          1773
TTT TCA TGA AAA AGT GGT CAA ATT ATG GTA GGC AAC TAA CGG TGT TTT TAC C  3'
--- --- --- --- --- --- --- --- --- --- --- --- --- --- --- --- ---
 F   S   *   K   S   G   Q   I   M   V   G   N   *   R   C   F   Y
```

FIG. 4C

```
          10         20         30         40         50         60
GACAGATGGC CATGGATTCA GATAAATTTG CAAAGAAAAA TGAGAGTCAC TGGTGTTATT
          70         80         90        100        110        120
ACCCAAGGAG CAAAAAGGAT TGGAAGCCCA GAGTACATAA AATCCTACAA AATTGCCTAC
         130        140        150        160        170        180
AGCAATGACG GGAAGACCTG GGCAATGTAC AAAGTAAAAG GCACCAATGA AGAGATGGTC
         190        200        210        220        230        240
TTTCGTGGAA ATGTTGATAA CAACACACCA TATGCTAATT CTTTCACACC CCCAATCAAA
         250        260        270        280        290        300
GCTCAGTATG TAAGACTCTA CCCCCAAATT TGTCGAAGGC ATTGTACTTT AAGAATGGAA
         310        320        330        340        350        360
CTTCTTGGCT GTGAGCTC.. .......... .......... .......... ..........
```

FIG. 5

```
     1                                                                        70
N-   CSTQLGMEGGAIADSQISASYVYMGFMGLQRWGPELARLYRTGIVNAWHASNYD-SKPWIQVNLLRKMRV
     **  ****  *    **  **                ***         *       *      ******
N-   CSGPLGIEGGIISNQQITASSTHRALFGLQKWYPYYARLNKKGLINAWTAAENDRWNRWIQINLQRKMRV
     1        10        20        30        40        50        60        70

71                                                                     140
     SGVMTQGASRAGRAEYLKTFKVAYSLDG-RKFEFIQDESGGDKEFLGNLDNNSLKVNMFNPTLEAQYIRL
     **  ****  *    ** *  ***  **          *  * ***  ***       *      ** **
     TGVITQGAKRIGSPEYIKFYKIAYSNDGKTWAMYKVKGTNEDMVFRGNIDNNTPYANSFTPPIKAQYVRL
     71        80        90       100       110       120       130       140

141                                                                    210
     YPVSCHRGCTLRFELLGCELHGCLEPLGLKNNTIPDSQMSASSSYKTWNLRAFGWYPHLGRLDNQGKINA
     **  *  ****  **********  ***  *** ***  ***    * *** **** *  ** *** **
     YPQVCRRHCTLRMELLGCELSGCSEPLGMKSGHIQDYQITASSIFRTLNMDMFTWEPRKARLDKGKVNA
     141       150       160       170       180       190       200       210

211                                                                    280
     WTAQSNSAKEWLQVDLGTQRQVTGIITQGARDFGHIQYVESYKVAHSDDGVQWTVY--EEQGSSKVFQGN
     **  *    ****   **  **********  *** *  *** *   *   * **          ******
     WTSGHNDQSQWLQVXLLVPTKVTGIITQGAKDXGHVQFVGSYKLAYSNDGEHWTVXQDEKQRKDKVXQGN
     211       220       230       240       250       260       270       280

281                            320
     LDNNSHKKNIFEKPFMARYVRVLPVSWHNRITLRLELLGC*  -C
     **  *    *  *  * ** **    ****    ******
     FDNDTHRKNVIDPPIYARHIRILPWSWYGRITLASELLGCT  -C
     281       290       300       310       320
```

1) CDPNPCENGGICLPGLAVG-----SFSCECPDGFTDPNCS SVVEVASDEEEPTSAGP
2) CTPNPCHNGGTCEISEAYRGDTFIGYVCKCPRGFNGIHCQ HNINE
3) CEVEPCKNGGICTDLVA-------NYSCECPGEFMGRNCQ YK

CONSENSUS   C---PC-NGG-C--------------Y-C-C--GY-G--C-
EGF DOMAIN                                F       F

FIG. 10

```
            9              18              27              36              45              54
5'-GT GAT ATT TGT GAT CCC AAT CCA TGT GAA AAT GGA GGT ATC TGT TTG CCA GGA
   --- --- --- --- --- --- --- --- --- --- --- --- --- --- --- --- ---
    X   D   I   C   D   P   N   P   C   E   N   G   G   I   C   L   P   G
           63              72              81              90              99             108
   TTG GCT GTA GGT TCC TTT TCC TGT GAG TGT CCA GAT GGC TTC ACA GAC CCC AAC
   --- --- --- --- --- --- --- --- --- --- --- --- --- --- --- --- ---
    L   A   V   G   S   F   S   C   E   C   P   D   G   F   T   D   P   N
          117             126             135             144             153             162
   TGT TCT AGT GTT GTG GAG GTT GGT CCC TGC ACT CCT AAT CCA TGC CAT AAT GGA
   --- --- --- --- --- --- --- --- --- --- --- --- --- --- --- --- ---
    C   S   S   V   V   E   V   G   P   C   T   P   N   P   C   H   N   G
          171             180             189             198             207             216
   GGA ACC TGT GAA ATA AGT GAA GCA TAC CGA GGG GAT ACA TTC ATA GGC TAT GTT
   --- --- --- --- --- --- --- --- --- --- --- --- --- --- --- --- ---
    G   T   C   E   I   S   E   A   Y   R   G   D   T   F   I   G   Y   V
          225             234             243             252             216             270
   TGT AAA TGT CCC CGA GGA TTT AAT GGG ATT CAC TGT CAG CAC AAC ATA AAT GAA
   --- --- --- --- --- --- --- --- --- --- --- --- --- --- --- --- ---
    C   K   C   P   R   G   F   N   G   I   H   C   Q   H   N   I   N   E
          279             288             297             306
   TGC GAA GTT GAG CCT TGC AAA AAT GGT GGA ATA TGT ACA G 3'
   --- --- --- --- --- --- --- --- --- --- --- --- ---
    C   E   V   E   P   C   K   N   G   G   I   C   T
```

FIG. 11

```
     EcoRI                               SacII   ApaI
     ▼                                    ▼       ▼
    GAATTCCGGG AGGGAGGGTA GGGGGGCGGG CCGCGGGGGC CCAAAGCCAG CTAGGCTCAG    60

TCTCACACGC GCGCCGCCAC TGTTTGTATA TAGTGCGCTC CTGGCCTCAG GCTCGCTCCC   120

CTCCAGCTCT CGCTTCATTG TTCTCCAAGT CAGAAGCCCC CGCATCCGCC GCGCAGCAGC   180

GTGAGCCGTA GTCACTGCTG GCCGCTTCGC CTGCGTGCGC GCACGGAAAT CGGGGAGCCA   240

GGAACCCAAG GAGCCGCCGT CCGCCCGCTG TGCCTCTGCT AGACCACTCG CAGCCCCAGC   300

CTCTCTCAAG CGCACCCACC TCCGCGCACC CCAGCTCAGG CGAAGCTGGA GTGAGGGTGA   360
                                                                Eco47III
                                                                ▼
    ATCACCCTTT CTCTAGGGCC ACCACTCTTT TATCGCCCTT CCCAAGATTT GAGAAGCGCT   420

AatII                                          PstI
                   ▼                                              ▼
    GCGGGAGGAA AGACGTCCTC TTGATCTCTG ACAGGGCGGG GTTTACTGCT GTCCTGCAGG   480

CGCGCCTCGC CTACTGTGCC CTCCGCTACG ACCCCGGACC AGCCCAGGTC ACGTCCGTGA   540

BspHI
       ▼
    GAAGGGATCA TGAAGCACTT GGTAGCAGCC TGGCTTTTGG TTGGACTCAG CCTCGGGGTG   600
               M  K  H  L  V  A  A   W  L  L  V   G  L  S   L  G  V

CCCCAGTTCG GCAAAGGTGA CATTTGCAAC CCGAACCCCT GTGAAAATGG TGGCATCTGT   660
     P  Q  F  G   K  G  D   I  C  N   P  N  P  C   E  N  G   G  I  C

BspMI
                                               ▼
    CTGTCAGGAC TGGCTGATGA TTCCTTTTCC TGTGAGTGTC CAGAAGGCTT CGCAGGTCCG   720
     L  S  G  L   A  D  D   S  F  S   C  E  C  P   E  G  F   A  G  P
```

FIG.12A

```
                                          BspMI
                                            ▼
AACTGCTCTA GTGTTGTGGA GGTTGCATCA GATGAAGAAA AGCCTACTTC AGCAGGTCCC 780
 N  C  S  S  V  V  E  V  A  S  D  E  E  K  P  T  S  A  G  P

TGCATCCCTA ACCCATGCCA TAACGGAGGA ACCTGTGAGA TAAGCGAAGC CTATCGAGGA 840
 C  I  P  N  P  H  N  G  G  T  C  E  I     S  E  A  Y  R  G

GACACATTCA TAGGCTATGT TTGTAAATGT CCTCGGGGAT TTAATGGGAT TCACTGTCAG 900
 D  T  F  I  G  Y  V  C  K  C  P  R  G  F  N  G  I  H  C  Q

CACAATATAA ATGAATGTGA AGCTGAGCCT TGCAGAAATG GCGGAATATG TACCGACCTT 960
 H  N  I  N  E  C  E  A  E  P  C  R  N  G  G  I  C  T  D  L

BsmI
                       ▼
GTTGCTAACT ACTCTTGTGA ATGCCCAGGA GAATTTATGG GACGAAATTG TCAATATAAA 1020
 V  A  N  Y  S  C  E  C  P  G  E  F  M  G  R  N  C  Q  Y  K

TGCTCTGGGC ACTTGGGAAT CGAAGGTGGG ATCATATCTA ATCAGCAAAT CACAGCTTCA 1080
 C  S  G  H  L  G  I  E  G  G  I  I  S  N  Q  Q  I  T  A  S

SacI
           EcI136II
           ▼▼
TCTAATCACC GAGCTCTTTT TGGACTCCAG AAGTGGTATC CCTACTATGC TAGACTTAAT 1140
 S  N  H  R  A  L  F  G  L  Q  K  W  Y  P  Y  Y  A  R  L  N

NcoI
                                                       MscI
                           PvuII                       BalI
                             ▼                          ▼▼
AAGAAGGGCC TTATAAATGC CTGGACAGCT GCTGAAAATG ACAGATGGCC ATGGATTCAG 1200
 K  K  G  L  I  N  A  W  T  A  A  E  N  D  R  W  P  W  I  Q

GTAACAGTGG GATGAGACAA ATCCATTTCC CAAATTATCA GAATCATTAT AGAAGTAGGT 1260
 V  T  V  G

TAGGGAGAAT TGGCTGTGAT TCTTTCTCAT GGTTAAAATG TGATTTAGTT CAGAATTAAC 1320
```

FIG.12B

```
ATGGTTCGAA ACTCTAAAAA ATGTGGAAAA CAGGAACATT CTATGTCTGA AAATCTGAAA 1380

ATAGCATCAA GATGAAAACA TTCTTTAGTC ATAAATATAC TCTTTTAAGT TATAGTAGAG 1440

BglII
          ▼
AAAAAGATCT TATCATTTCA TAAGTGGACT TTTGGGATAG CATTGGAAAT GTAAATGAAA 1500

SspI
                                        ▼
TAAATACCTA ATTGAAAAAA GTTTATTCTA AAGTGTTAAT ATTTAGCAAC AGATTCAGAG 1560

ACAAGAAAGT AACAATTCAA TCTGTGTATT TTTTGTGAGA AATAGTTTCC CATGTGCAAA 1620

FspI   BspHI                    PstI
        ▼      ▼                        ▼
TATAAAGTGC GCATCATATC ATGATAATAT CCAACTGTCT GCAGAACTCC CTTTCATAAA 1680

TGAGAGAATT TTAATTCATA GTGCCTTATA TCCTCATCAG CCATCTGACT TACTACAGA 1740

NsiI
               ▼
AGAAAACAAT GAAATGATGC ATTAAGTGCT TTGCTAGAAG AAACATCATA GCAAAGCTGA 1800

XhoI
              HindIII   PaeR7I
                ▼         ▼
TAGCCCACAT TCTGTGCANN NAAGCTTCCA GAGCACTCGA GAAAAAGCAG AAATGAGATG 1860

BclI
                                  ▼
TTTTATGAAA ACCGAAAAGA TAATCTGATT TCTGTGAAAT ATACTTTTGA TCATGTGGTT 1920

CTTTAAGATA GTCACTAACA AGTCATTAGT AGCAGATACC AAATGGGAGA AAATTTCCAG 1980

BstI1071
    ▼
TATACTGACG GTCAAGGCAG TCATGCTGAA ACTACATGAG GTCAGGAAAG TTTTGAAATA 2040
```

FIG. 12C

```
AGGTGATTTT GGAAGGATAC CTTCAACTGG CCTAGATTTT CAAGAAACAG TGTAATCAAC  2100

AGCCAAACAT GAGAATCTAG CTAACAGCAT TTAGAAAACC AGAACTAAGA GTGTTACTGG  2160

DraI
                  ▼
GGAATTGCAT TTAAATCCAG TATGAGAGTT TGCAAATGCC GTATTCTTCT AAGGGGTTTG  2220

NcoI
                  ▼
TGCCACATTT TGTTACCATG GAGTCCTCTG TAAGAACTTT ATTAGATAAA TCATCTTTAC  2280

EcoRI
                     ▼
ACTATAATTT GAATAAAAGC CGGAATTC                                     2308
```

FIG.12D

US 7,041,801 B1

ANTIBODIES BINDING TO POLYPEPTIDES ENCODED BY DEVELOPMENTALLY-REGULATED ENDOTHELIAL CELL LOCUS-1

This is a divisional application of U.S. patent application Ser. No. 08/659,235, filed Jun. 5, 1996, now U.S. Pat. No. 5,877,281, issued on Mar. 2, 1999, which is a continuation-in-part of U.S. patent application Ser. No. 08/480,229, filed Jun. 7, 1995, now U.S. Pat. No. 5,874,562, issued on Feb. 23, 1999, each of which is incorporated herein in its entirety.

This invention was made, in part, with government support under HD 25580 awarded by the National Institutes of Health. The government may have certain rights in the invention.

FIELD OF THE INVENTION

1. Introduction

The present invention relates to a member of a novel gene family referred to as developmentally-regulated endothelial cell locus-1 (del-1). In particular, the invention relates to Del-1 nucleotide sequences, Del-1 amino acid sequences, methods of expressing a functional gene product, antibodies specific for the gene product, and methods of using the gene and gene product. Since Del-1 is expressed in endothelial cells and certain cancer cells, it may be useful as an endothelial cell and tumor marker. In addition, the ability of Del-1 protein to inhibit vascular formation provides for its use as an anti-angiogenic agent.

BACKGROUND OF THE INVENTION

2.1 Endothelial Cell Biology and Blood Vessel Development

The endothelium occupies a pivotal position at the interface between the circulating humoral and cellular elements of the blood, and the solid tissues which constitute the various organs. In this unique position, endothelial cells regulate a large number of critical processes. Such processes include leukocyte adherence and transit through the blood vessel wall, local control of blood vessel tone, modulation of the immune response, the balance between thrombosis and thrombolysis, and new blood vessel development (Bevilacqua et al., 1993, *J. Clin. Invest.* 91: 379–387; Folkman et al., 1987, *Science* 235: 442–447; Folkman et al., 1992, *J. Biol. Chem.* 267: 10931–10934; Gimbrone, 1986, Churchill Livingstone, London; Issekutz, 1992, *Curr. Opin. Immunol.* 4:287–293; Janssens et al., 1992, *J. Biol. Chem.* 267:14519–14522; Lamas et al. 1992, *Proc. Natl. Acad. Sci. U.S.A.* 89:6348–6352, Luscher et al. 1992, *Hypertension* 19:117–130; Williams et al., 1992, *Am. Rev. Respir. Dis.* 146:S45–S50; Yanagisawa, et al., 1988, *Nature* 332:411–415).

Endothelial cell dysfunction has been postulated as a central feature of vascular diseases such as hypertension and atherosclerosis. In this context, the ability of the endothelium to synthesize smooth muscle cell mitogens and factors which control smooth muscle contraction has received much attention (Janssens et al., 1992, *J. Biol. Chem.* 267:14519–14522; Lamas et al., 1992, *Proc. Natl. Acad. Sci. U.S.A.* 89:6348–6352; Luscher et al., 1992, *Hypertension* 19:117–130; Raines et al., 1993, *Br. Heart J.* 69:S30–S37; Yanagisawa et al., 1988, *Nature* 332:411–415). The endothelial cell has also become the focus of attention in the study of diseases which are not primarily vascular in nature. Diverse disease processes such as adult respiratory distress syndrome, septic shock, solid tumor formation, tumor cell metastasis, rheumatoid arthritis, and transplant rejection are now understood to be related to normal or aberrant function of the endothelial cell. A rapidly increasing number of pharmacologic agents are being developed whose primary therapeutic action will be to alter endothelial cell function. In addition, recent attention on gene therapy has focused on the endothelial cell (Nabel et al., 1991, *J. Am. Coll. Cardiol.* 17:189B–194B). Transfer of genes into the endothelial cell may afford a therapeutic strategy for vascular disease, or the endothelium may serve simply as a convenient cellular factory for a missing blood borne factor. Hence, information regarding fundamental processes in the endothelial cell will aid the understanding of disease processes and allow more effective therapeutic strategies.

Studies from a number of laboratories have characterized the ability of the endothelial cell to dramatically alter basic activities in response to cytokines such as tumor [3]necrosis factor (TNF)-alpha. TNF-alpha stimulation induces significant alterations in the production of vasoactive compounds such as nitric oxide and endothelin, increases surface stickiness toward various types of leukocytes, and modulates the expression of both pro- and anti-coagulant factors (Cotran et al., 1990, *J. Am. Soc. Nephrol.* 1:225–235; Mantovani et al., 1992, *FASEB J.* 6:2591–2599). In turn, endothelial cells have been shown to be an important source for the production of cytokines and hormones, including interleukin 1, 6 and 8 (Gimbrone et al., 1989, *Science* 246:1601–1603; Locksley et al. 1987, *J. Immunol.* 139:1891–1895; Loppnow et al., 1989, *Lymphokine. Res.* 8:293–299; Warner et al., 1987, *J. Immunol.* 139:1911–1917).

The ability of endothelial cells to produce granulocyte, granulocyte-macrophage, and macrophage colony stimulating factors has led to speculation that endothelial cells are an important facet of hematopoietic development (Broudy et al., 1987, *J. Immunol.* 139:464–468; Seelentag et al., 1987, *EMBO J.* 6:2261–2265). Early studies have provided the foundation for the cloning of a large number of "endothelial cell-specific" genes. Some of these include ICAM-1, ICAM-2, VCAM-1, ELAM-1, endothelin-1, constitutive endothelial cell nitric oxide synthetase, thrombomodulin, and the thrombin receptor (Bevilacqua et al., 1989, *Science* 243: 1160–1165; Jackman et al., 1986, *Proc. Natl. Acad. Sci. U.S.A.* 83:8834–8838; Janssens et al., 1992, *J. Biol. Chem.* 267:14519–14522; Lamas et al., 1992, *Proc. Natl. Acad. Sci. U.S.A.* 89:6348–6352; Osborn et al., 1989, *Cell* 59:1203–1211; Staunton et al., 1–969, *Nature* 339:61–64, Staunton et al., 1988, *Cell* 52:925–933; Vu et al, 1991, *Cell* 64:1057–1068; Yanagisawa et al., 1988, *Nature* 332:411–415).

All blood vessels begin their existence as a capillary, composed of only endothelial cells. Much of the molecular research investigating the role of endothelial cells in blood vessel development has focused on this process in the adult organism, in association with pathological conditions. In these situations, new blood vessels are formed by budding and branching of existing vessels. This process, which depends on endothelial cell division, has been termed angiogenesis. Research on this process has focused primarily on small proteins which are growth factors for endothelial cells (Folkman et al., 1987, *Science* 235:442–447; Folkman et al., 1992, *J. Biol. Chem.* 267:10931–10934). Sensitive bioassays for angiogenesis have allowed the characterization of a number of angiogenic factors, from both diseased and normal tissues. Members of the fibroblast growth factor (FGF) family, platelet-derived endothelial cell growth factor, and vascular endothelial cell growth factor (vascular permeability factor), are a few of the angiogenic factors which have been characterized (Folkman et al., 1987, *Science* 235: 442–447; Folkman et al., 1992, *J. Biol. Chern.* 267:10931–10934; Ishikawa et al., 1989, *Nature* 338:557–562; Keck et al., 1989, *Science* 246:1309–1312; Leung et al., 1989, *Science* 246:1306–1309).

Such information has provided some insight into the study of blood vessel development in the embryo. Studies linking vascular development to an angiogenic factor have resulted in the work with vascular endothelial cell growth factor (VEGF). VEGF expression has been correlated in a temporal and spatial fashion with blood vessel development in the embryo (Breier et al., 1992, *Development* 114:521–532). A high affinity VEGF receptor, flk-1, has been shown to be expressed on the earliest endothelial cells in a parallel fashion (Millauer et al., 1993, *Cell* 72:835–846).

Blood vessels form by a combination of two primary processes. Some blood vessel growth depends on angiogenesis, in a process very similar to that associated with pathological conditions in the adult. For instance, the central nervous system depends solely on angiogenesis for development of its vascular supply (Noden, 1989, *Am. Rev. Respir. Dis.* 140:1097–1103; Risau et al., 1988, *EMBO J.* 7:959–962). A second process, vasculogenesis, depends on the incorporation of migratory individual endothelial cells (angioblasts) into the developing blood vessel. These angioblasts appear to be components of almost all mesoderm, and are able to migrate in an invasive fashion throughout the embryo (Coffin et al., 1991, *Anat. Rec.* 231:383–395; Noden, 1989, *Am. Rev. Respir. Dis.* 140:1097–1103; Noden 1991, *Development* 111:867–876). The precise origin of this cell, and the characteristics of its differentiation have not been defined.

Understanding of the molecular basis of endothelial cell differentiation in blood vessel development may allow manipulation of blood vessel growth for therapeutic benefit. The ability to suppress blood vessel growth may also provide therapeutic strategies for diseases such as solid tumors and diabetic retinopathy. On the other hand, diseases such as coronary artery disease may be treated through pharmacologic induction of directed blood vessel growth, through increasing collateral circulation in the coronary vascular bed. Both vascular diseases such as atherosclerosis and hypertension and nonvascular diseases which depend on the endothelial cell will benefit from a better understanding of endothelial cells.

2.2 Epidermal Growth Factor-Like Domain

Epidermal growth factor (EGF) stimulates growth of a variety of cell types. EGF-like domains have been found in a large number of extracellular and membrane bound proteins (Anderson, 1990, *Experientia* 46(1): 2; and Doolittle, 1985, *TIBS*, June:233). These proteins include molecules that function as soluble secreted proteins, growth factors, transmembrane signal and receptor molecules, and components of the extracellular matrix (Lawler and Hynes, 1986, *J. Cell Biol.* 103:1635; Durkin et al., 1988, *J. Cell Biol.* 107:2749; Wu et al., 1990, *Gene* 86:275; Bisgrove and Raff, 1993, *Develop. Biol.* 157:526).

In many cases, multiple tandem repeats of a characteristic 40 amino acid long, 6 cysteine-containing sequence are observed (Anderson, 1990, *Experientia* 46(1): 2). EGF-like domains are homologous to the peptide growth factor EGF which consists of a single copy of the standard EGF domain. These domains have been highly conserved in evolution, being found in species as diverse as nematodes, *Drosophila*, sea urchins, and vertebrates.

The EGF molecule and the closely related transforming growth factor (TGF) alpha induce cell proliferation by binding to a tyrosine kinase receptor. It has been suggested that other EGF-like domains also function as ligands for receptor molecules (Engel, 1989, *FEBS Lett.* 251:1–7). Fundamentally, EGF repeats are protein structures that participate in specific protein-protein binding interactions.

The *Drosophila* Notch protein, the Nematode lin-12 and glp-1 proteins, and the closely related vertebrate homologs, Motch (mouse Notch), Xotch (*Xenopus* Notch), rat Notch, and TAN 1 (human Notch) are membrane bound receptor molecules that control the specification of cell fate for a variety of cell types early in embryogenesis (Rebay et al., 1991, *Cell* 67:687; Hutter and Schnabel, 1994, *Development* 120:2051; Del Amo et al. 1992, *Development* 115:737; Reaume et al. 1992 *Develop. Biol.* 154:377; and Ellisen et al., 1991, *Cell* 66:649). Specific EGF-like repeats in the Notch receptors are binding sites that attach to protein ligands leading to signal transduction (Rebay et al., 1991 *Cell* 67:687; Couso and Arias, 1994, *Cell* 79:259; Fortini and Artavanis-Tsakonas, 1994, *Cell* 79:273; Henderson et al., 1994, *Development* 120:2913). Extracellular matrix proteins such as thrombospondin, entactin, tenascin and laminin play key roles in morphogenesis by providing the physical scaffold to which cells attach to form and maintain tissue morphologies (Frazier, 1987, *J. Cell. Biol.* 105:625; Taraboletti et al., 1990, *J. Cell. Biol.* 111:765; Ekblom et al., 1994, *Development* 120:2003).

2.3 Discoidin I/Factor VIII-Like Domains

A homologous domain structure has been discovered in coagulation factors VIII and V (Kane and Davie, 1986, *Proc. Natl. Acad. Sci. U.S.A.* 83:6800). This domain is related to a more ancient structure first observed in the discoidin I protein produced by the cellular slime mold *Dictyostelium discoideum*. Discoidin I is a carbohydrate binding lectin secreted by *Dictyostelium* cells during the process of cellular aggregation and is involved in cell-substratum attachment and ordered cell migration (Springer et al., 1984, *Cell* 39:557).

Discoidin I/factor VIII-like domains have also been observed in a number of other proteins. For example, milk fat globule protein (BA46), milk fat globule membrane protein (MFG-E8), breast cell carcinoma discoidin domain receptor (DDR), and the *Xenopus* neuronal recognition molecule (A5) (Stubbs et al., 1990, *Proc. Natl. Acad. Sci. U.S.A.* 87:8417; Larocca et al., 1991, *Cancer Res.* 51:4994; Johnson et al., 1993, *Proc. Natl. Acad. Sci. U.S.A.* 90:5677). The discoidin I/factor VIII-like domains of the vertebrate proteins are all distantly related to the *Dictyostelium* sequence but more closely related to each other.

Discoidin I/factor VIII-like domains are rich in positively charged basic amino acids and are believed to bind to negatively charged substrates such as anionic phospholipids or proteoglycans. Both of the milk fat globule proteins have been shown to associate closely with cell membranes and the coagulation factors VIII and V interact with specific platelet membrane proteins (Stubbs et al., 1990 *Proc. Natl. Acad. Sci. U.S.A.* 87:8417; Larocca et al., 1991, *Cancer Res.* 51:4994).

3. SUMMARY OF THE INVENTION

The present invention relates to a novel gene family referred to as del-1. In particular, it relates to del-1 nucleotide sequences, expression vectors containing the sequences, genetically-engineered host cells expressing del-1, Del-1 protein, Del-1 mutant polypeptides, methods of expressing del-1 and methods of using del-1 and its gene product in various normal and disease conditions such as cancer.

The invention is based, in part, upon Applicants' isolation of a murine DNA clone (SEQ ID NO: 9), del-1, and its homologous human counterpart, (SEQ ID NO: 11). Structural features of the Del-1 protein are deduced by homology comparisons with sequences in the Genbank and NBRF-PIR databases. The protein is a modular molecule composed of repeats of two different sequence motifs which are present in a number of distinct proteins. The two sequence motifs are known as the EGF-like domain (SEQ ID NO: 26) and the discoidin I/factor VIII-like domain (SEQ ID NOS: 1–8). These domains are defined by characteristic patterns of conserved amino acids distributed throughout the molecule at specific locations. While Del-1 shows certain sequence homology with other proteins, it is unique in both its primary sequence and its overall structure. In all cases in which EGF-like and discoidin I-like domains have been identified, both of these structures are always found in extracellular locations. Variant forms of Del-1 protein exist, and one form is shown herein to be an extracellular matrix protein and is associated with the cell surface. The expression pattern of del-1 further indicates that it is involved in endothelial cell function. In addition, a number of human tumor cells express del-1. Furthermore, host-derived blood vessels that traverse the tumor nodule also express del-1. The Del-1 protein inhibits vascular morphogenesis and binds to $\alpha V \beta 3$ as its cellular receptor. Therefore, a wide variety of uses are encompassed by the present invention, including but not limited to, the use of Del-1 as a tumor marker for cancer diagnosis and treatment, the isolation of embryonic endothelial cells, the identification of Del-1 binding partners, and the stimulation or inhibition of endothelial cell growth and blood vessel formation.

4. BRIEF DESCRIPTION OF THE DRAWINGS

FIG. 1. Genomic organization of 42 kb of the murine del-1 locus, as characterized by cloning from a λfix library constructed from the SLM275 transgenic mouse, and a wildtype 129SV λfix library. The dashed line indicates DNA studied to date by zoo blot and exon trapping. The location of the exon identified by exon trapping is shown.

FIG. 2. Homology analysis between the deduced amino acid sequence of the putative del-1 gene (m-del1) (SEQ ID NO: 1) and other proteins with "discoidin-like domains." Identical residues are boxed, conserved residues are in bold (Geneworks, Intelligenetics, Mountain View, Calif.). m-del-1 sequence (SEQ ID NO: 1) was derived from a trapped exon and mouse embryo cDNAs. Abbreviations: h-MFG, human milk fat globule protein (SEQ ID NO: 2); h-FV, human coagulation factor V (SEQ ID NO: 3); m-FVIII, mouse coagulation factor VIII (SEQ ID NO: 4); X-A5b1 (SEQ ID NO: 5) and X-A5b2 (SEQ ID NO: 6), b1 and b2 domains of Xenopus neuronal antigen A5; dis-I, discoidin I (SEQ ID NO: 7); consensus sequence (SEQ ID NO: 8).

FIG. 3A-3D. Nucleotide sequence and deduced amino acid sequence of murine del-1 cDNA (SEQ ID NO: 9) and (SEQ ID NO: 10).

FIG. 4A-4C. Nucleotide sequence and deduced amino acid sequence of sequence of human del-1 cDNA (SEQ ID NO: 11) and (SEQ ID NO: 14).

FIG. 5. Murine del-1 fragment (SEQ ID NO: 19) used as probe for human del-1 cloning and Northern blot analysis.

Figure 6:
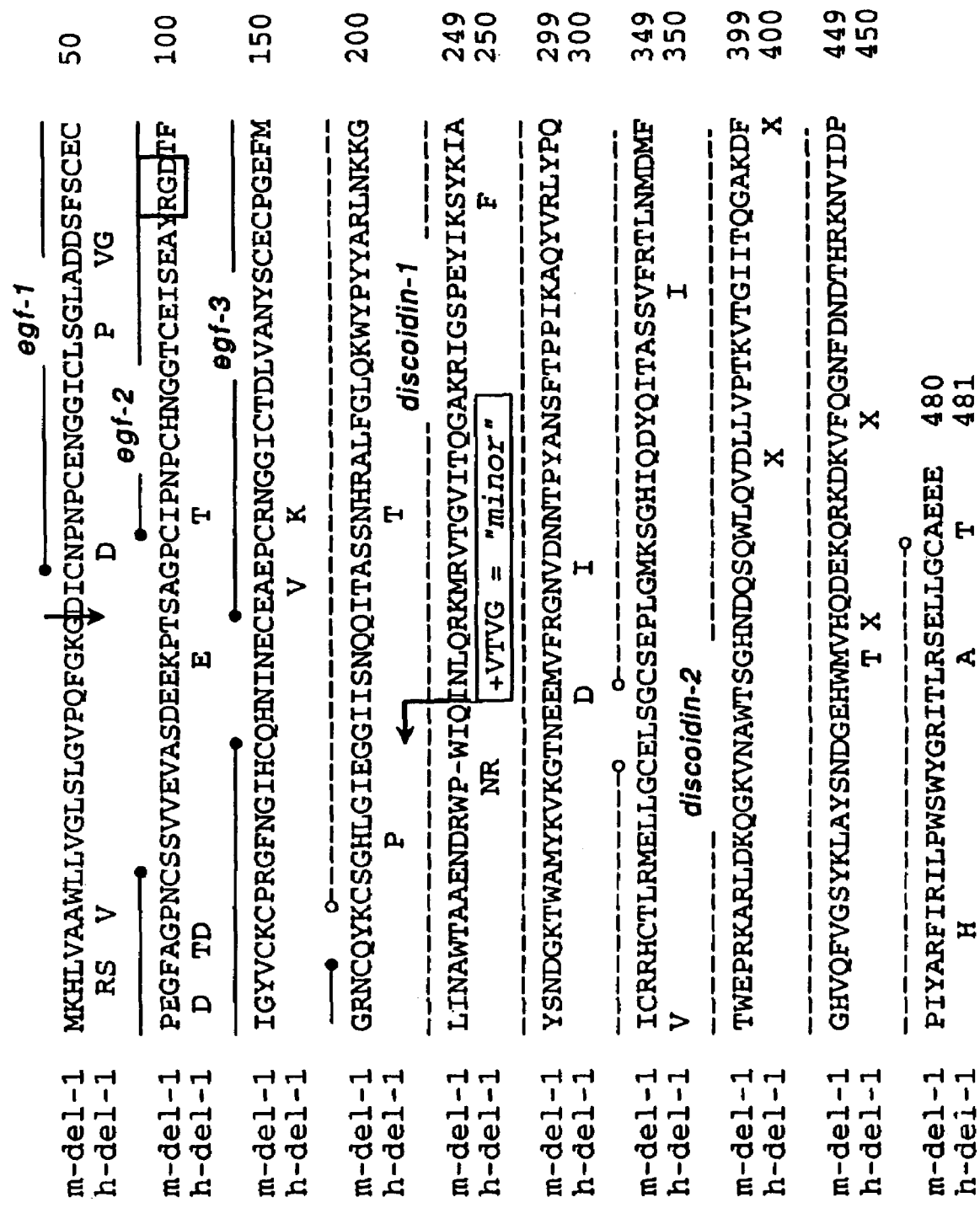

FIG. 6. Amino acid sequence comparison between murine (m-del-1) (SEQ ID NO: 10) and human (h-del-1) (SEQ ID NO: 30) Del-1-proteins. The EGF-like and discoidin-like domains are indicated by "egf" and "discoidin," respectively.

Figure 7:
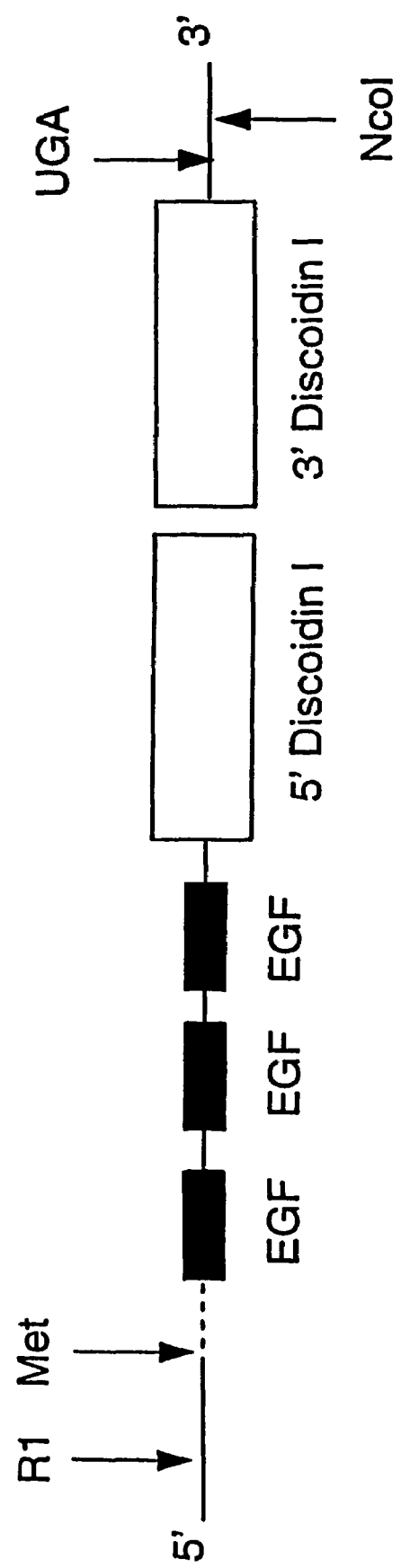

FIG. 7. The small rectangles labeled "EGF" show the location and relative sizes of the three EGF-like domains of Del-1. These regions of the protein are approximately 40 amino acids long. Each EGF-like domain contains six cysteine residues and additional conserved amino acids, distributed in a pattern which is highly conserved among proteins that contain this common motif. In addition, the amino acid sequence RGD occurs in the center of the second EGF-like repeat. This sequence is found in a variety of extracellular matrix proteins and, in some cases, it is required for binding to integrin proteins. An RGD sequence is present in the same position in the second EGF-like repeat of MFG-E8. The large rectangles on the right side represent tandem discoidin I/factor VIII-like domains. This protein motif is based on a conserved pattern of amino acids defined by the homology between the D. discoidium discoidin I protein and mammalian coagulation factor VIII.

FIG. 8. The 54.2% amino acid homology between human Del-1 (SEQ ID NO:21) and MFG-E8 (SEQ ID NO: 20) in the tandem discoidin I/factor VIII domains is shown. These domains are rich in the basic amino acids arginine and lysine. The 5' domain contains 12 arginines and 12 lysines versus 9 acidic residues, while the 3' domain contains 8 arginines and 10 lysines versus 16 acidic residues. A similar domain in the coagulation factor VIII protein is believed to bind to negatively charged phospholipids on the surface of platelets. The MFG-E8 protein has been found to associate tightly with milk fat globule membranes.

FIG. 9. The predicted amino acid sequence at the amino terminus of the human Del-1 protein (SEQ ID NO: 22) shows characteristics common to signal peptides. The putative signal sequence of human Del-1 (SEQ ID NO. 22 from residues # 3 to #21) begins with a basic arginine residue and is followed by a stretch of 18 amino acids rich in hydrophobic residues. Signal peptides typically end with a small amino acid such as glycine or alanine. In addition, the Chou and Fasman algorithm predicts that the putative signal sequence is followed by a protein turn structure, a feature commonly found after signal peptides. The Del-1 protein is secreted by expressing cells.

FIG. 10. Sequence similarities between the three EGF-like domains of Del-1 EGF-like domain of Del-1 (1): SEQ ID NO. 23: EGF-like domain of Del-1 (2): SEQ ID NO. 24; EGF-like domain of Del-1 (3): SEQ ID NO. 25) and homology with the consensus EGF-like domain amino acid sequence (CONSENSUS EGF DOMAIN: SEQ ID NO: 26). Also, the amino acid sequence RGD is in the center of the second EGF-like repeat. This sequence is found in a variety of extracellular matrix proteins and, in some cases is required for binding to integrin proteins. An RGD sequence is present in the same position in the second EGF-like repeat of MFG-E8.

FIG. 11. Human del-1 splicing variant partial sequence (Nucleotide sequence: SEQ ID NO: 27; amino acid sequence: SEQ ID NO. 31) showing the variation as compared with the major form.

FIG. 12A-12D. Murine del-1 truncated minor nucleotide and deduced amino acid sequences (SEQ ID NO: 28) and (SEQ ID NO: 29).

FIG. 13A-13H. X-gal staining in whole mount and tissue sections of embryos from the SLM275 line. (13A) Embryo at 7.5 days pc (headfold stage) stained as whole mount.

X-gal staining is seen in cells of the extraembryonic mesoderm (xm) which will give rise to the yolk sac and associated blood islands. Abbreviations: ng, neural groove. Photographed at 70×. (13B) Section of yolk sac blood islands from 8 day pc embryo stained as a whole mount with membranes intact and subsequently sectioned and counterstained. Clusters of round cells in the blood islands show X-gal staining (arrow), while mature endothelial cells do not stain (open arrowhead). Photographed at 400×. (13C) Embryo at 9.5 days pc. Prominent X-gal staining (blue-green) is seen in the heart and outflow tract (mid-portion of embryo). In addition, the aorta (arrowhead) and intervertebral vessels are stained. Photographed at approximately 30×, darkfield illumination. (13D) Section of 9.5 day embryo showing heart and outflow tract. This section indicates that X-gal staining in the heart and outflow tract is restricted to the endothelial cells (endocardium). Section was counterstained with hematoxylin and eosin, photographed at 200×. (13E) Embryo at 13.5 days pc, dissected and X-gal stained as a whole mount. At this stage, as confirmed by study of tissue sections, endothelial cells lining the ventricle (v) and large vessels such as the aorta (filled arrowhead) have lost most of their staining. Staining of the endothelial cells of the atrium (a) has diminished but is still apparent in the whole mount. Most pronounced at this stage is staining in the developing lungs (open arrowheads). X-gal staining cells are clearly associated with the glandular buds of the lung, but it is not possible to identify these cells in the whole mount. The only non-cardiovascular cells which exhibit X-gal staining are cells in the regions of ossification, such as in the proximal ribs shown here. Photographed at 50×. (13F) Embryo at 13.5 days, stained as whole mount, sectioned, counterstained with nuclear fast red. X-gal staining in lung tissue shown here is associated with endothelial cells, as seen in vascular channels cut in transverse (arrow) and longitudinal (arrowhead) planes. Staining is not associated with bronchial cells. Section was photographed at 400×. (13G) Cross-section through a valve forming in the outflow tract of a 13.5 day embryo. Endothelial cells in blood vessel wall are undergoing an epithelial-mesenchymal transformation, leading to formation of the valve tissue. Stained cells are seen within the forming valve structure, indicating that these cells continue to express the del-1 marker during this phenotypic transformation. The embryo was stained as a whole mount, sectioned, counterstained with nuclear fast red and photographed at 400×. (13H) Spiral septal formation in the outflow tract of the heart at 9.5 days pc. Endothelial cells are undergoing an epithelial-mesenchymal transformation, becoming mesenchymal in morphology and behavior. Endothelial cells continue to express the transgene marker for some time after this transformation. Section from whole mount stained embryo, 200×.

Figure 14A:
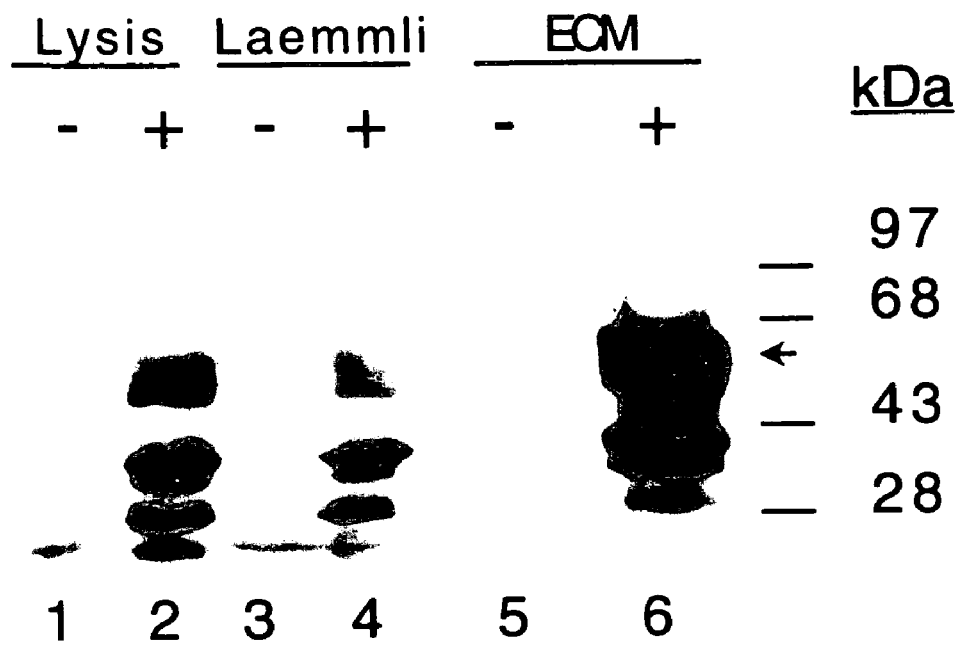
Figure 14B:

FIGS. 14A & 14B. Immunoblotting employing del-1 transfected yolk sac cells. (14A) Yolk sac YS-B cells stably transfected with a eukaryotic expression vector encoding the murine major form of del-1 (+), or an empty expression vector (−) were selected and evaluated as pools for expression of Del-1 protein. Protein was isolated from cells lysed in cell lysis buffer (Lysis) or standard Laemmli gel loading buffer (Laemmli), or from the extracellular matrix remaining after transfected cells were removed from the culture dish (ECM). The dominant band corresponds to a molecular weight of 52 kilodaltons (kDa). Lower molecular weight bands most likely represent protein degradation products, although the use of alternative translation initiation sites is also possible. (14B) YS-B cells were stably transfected with the del-1 expression construct, or the empty expression plasmid, and selected as individual clones. Clones expressing del-1 were selected for varying levels of protein production, as assayed by western blot analysis of extracellular matrix protein. Clone L10 shows the highest level of del-1 mRNA, clones L13 and L14 have an intermediate amount of: message, and a negative control clone does not express del-1.

Figures 15A, 15B:
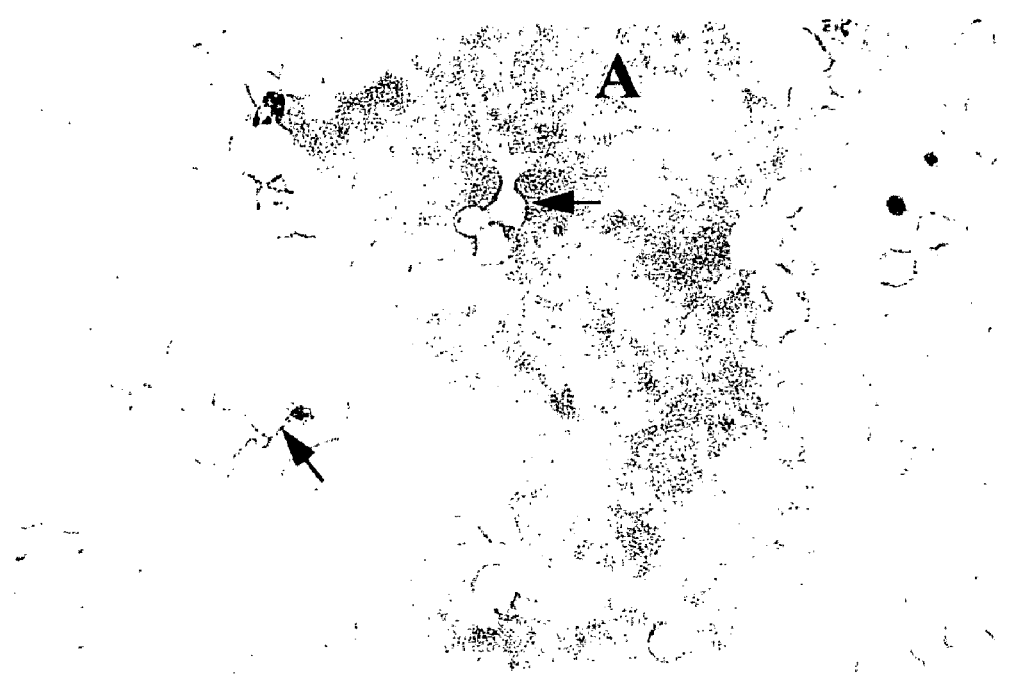

FIG. 15A-15B. Immunostaining of yolk sac cells. (15A) del-1 transfected yolk sac cells and the extracellular matrix are stained with anti-Del-1 antibody. The arrows indicate cell membrane staining. (15B) Mock-transfected yolk sac cells are not stained with antibody.

Figure 16:

FIG. 16. Immunostaining of Del-1 in the developing bone (vertebral column) of a 13.5 day mouse embryo. The lacunae within the bone are structures composed of extracellular matrix proteins and they are stained for Del-1.

FIG. 17. Immunostaining of human glioma grown in nude mice. (17A) tumor cells are stained with anti-Del-1 antibody. Polarized staining pattern is observed (arrows). (17B) a blood vessel is stained with anti-Del-1 within the tumor.

FIG. 18A-18H. (18A) The parental yolk sac cell line YS-B under routine culture conditions. Phase contrast, photo 100×. (18B) YS-B cells after 24 hrs on "MATRIGEL" show a pattern of vascular morphogenesis. Cells were stained with toluidine blue. Brightfield, photo 40×. (18C) Negative control transfectants form a vascular network on "MATRIGEL" after 24 hours. Light areas represent organized cells; photographed under dark field illumination at 50×. (18D) Yolk sac transfectant, clone L10, after 24 hrs on "MATRIGEL" shows no evidence of vascular formation, cells instead produce numerous aggregates. Darkfield illumination, photo 50×. (18E) Parental yolk sac YS-B cells grown on a matrix produced by negative control transfectants make a complex structural network. Light areas represent organized cells; photographed under darkfield illumination at 30×. (18F) Parental YSB cells grown on a matrix produced by del-1 transfectants. Cells are forming a dense monolayer, with no evidence of organization. Photographed under darkfield illumination at 30×. (18G) Aggregates of negative control transfected yolk sac cells are placed onto polymerized "MATRIGEL". After 24 hrs, cells show sprouting angiogenesis. Photographed under phase contrast, at 100×. (18H) Aggregates of del-1 transfected yolk sac clone L10 are placed onto polymerized "MATRIGEL" as in 18G. Photographed after 24 hrs (100×), these cells show no evidence of sprouting.

Figure 19:
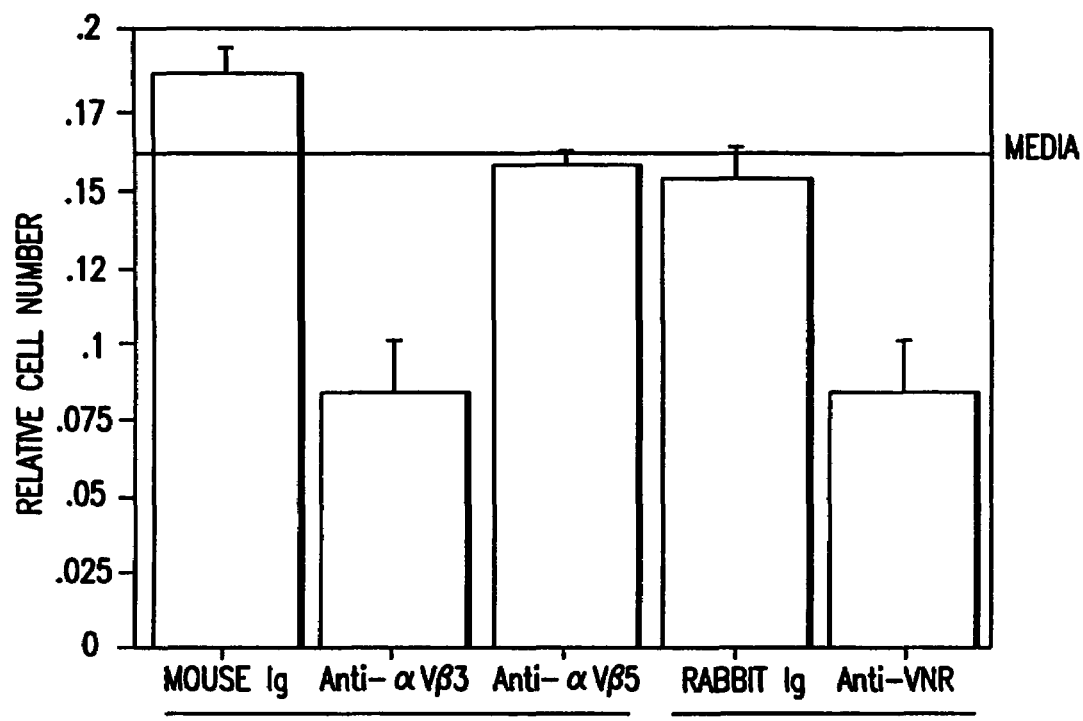

FIG. 19. The binding of murine recombinant Del-1 to HUVEC is inhibited by an anti-αVβ3 antibody. The relative cell number of HUVEC adhered to plates coated with recombinant Del-1 is shown in the presence of various antibodies.

Figure 20:
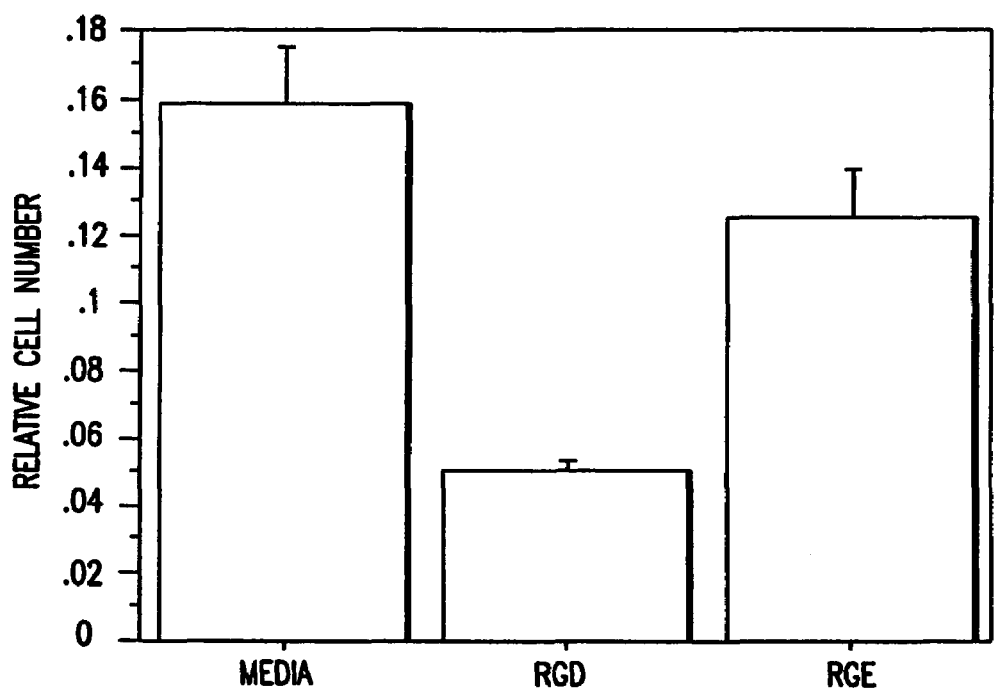

FIG. 20. The binding of murine recombinant Del-1 to HUVEC is inhibited by RGD peptides. The relative cell number of HUVEC adhered to plates coated with recombinant Del-1 is shown in the presence of RGD and RGE peptides at 10 µg/ml.

Figure 21A:
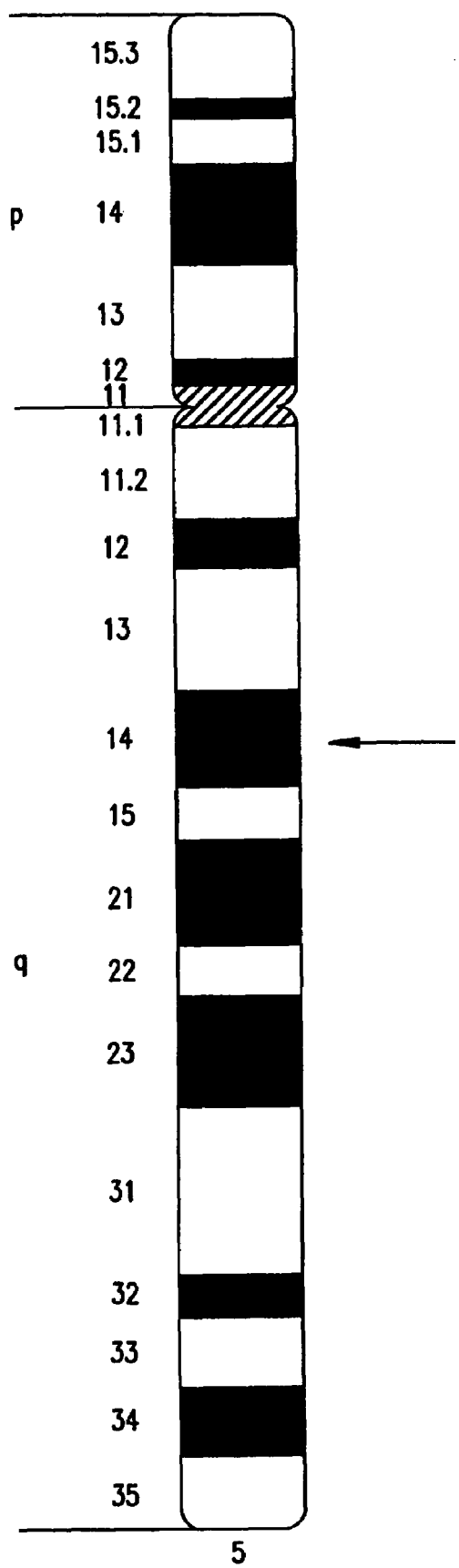
Figure 21B:
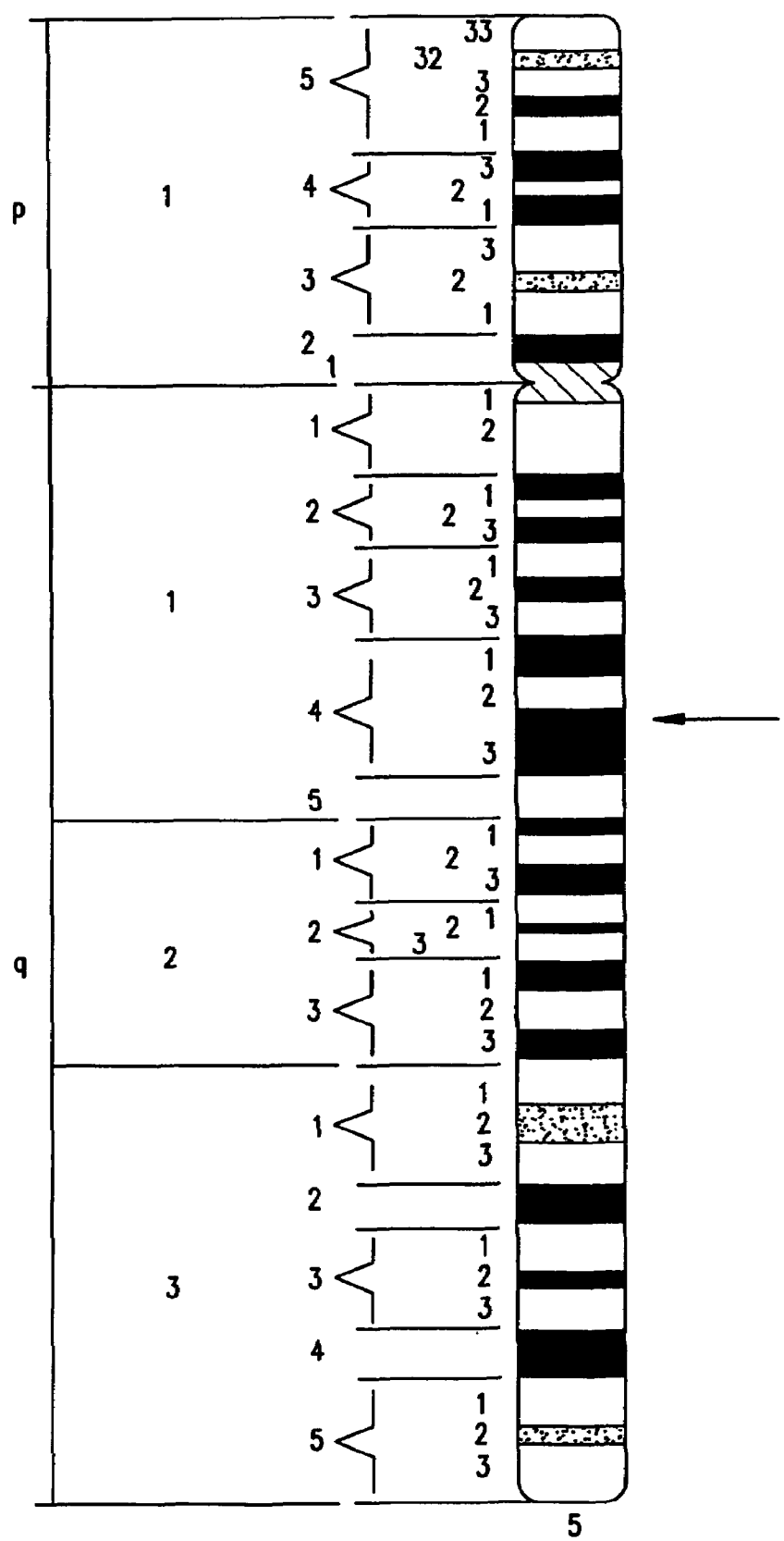

FIGS. 21A & 21B. Two ideograms illustrating the chromosomal position of P1 clone 10043 at 5q14. (21A) nomenclature for human chromosomes adopted from the International System for Human Cytogenetic Nomenclature (1985). (21B) an ideogram adopted from *Cytogenet. Cell Genet.* 65: 206–219 (1994) which shows the relative band positions and arm ratios derived from actual chromosome measurements.

5. DETAILED DESCRIPTION OF THE INVENTION

The present invention relates to a novel family of genes herein referred to as del-1. Described below are methods for cloning members of this gene family, characteristics of a murine member and its human homolog, expression of recombinant gene products, and methods of using the gene and its gene product. Structurally, members of this gene family contain three EGF-like domains and two discoidin I/factor VIII-like domains.

The overall structure of the del-1 molecule is similar to the milk fat globule membrane protein (MFG-E8) (Stubbs et al., 1990, *Proc. Natl. Acad. Sci. U.S.A.* 87:8417). MFG-E8 is highly expressed by a large portion of human breast tumors as well as by lactating mammary epithelial cells. It consists of two tandem EGF-like domains followed by two discoidin I/factor VIII-like domains. The function of MFG-E8 is not known but it has been shown to associate closely with cell membranes and has been investigated as a target for antibody-based tumor imaging techniques. The observed association of MFG-E8 with cell membranes indicates the potential use of antibodies against Del-1 to identify and sort endothelial cells from mixed cell populations, and to target tumor cells that express Del-1 for diagnosis and therapy.

The second EGF-like repeat of MFG-E8 contains the amino acid sequence arg-gly-asp (RGD) in the same position as the second EGF-like repeat of Del-1. The RGD sequence has been shown to be a cell binding site for fibronectin, discoidin I, nidogen/entactin, and tenascin (Anderson, 1990, *Experientia* 46:2). The binding of fibronectin to cell surface integrin molecules through the RGD sequence has been extensively studied (Main et al., 1992, *Cell* 71:671; Hynes, 1992, *Cell* 69:11). Integrins appear to be the major receptors by which cells attach to extracellular matrices. Substrate binding to integrins has been shown to initiate signal transduction leading to events such as tyrosine phosphorylation, cytoplasmic alkalinization, activation of secretion and differentiation (Hynes, 1992, *Cell* 69:11). The presence of the RGD sequence in Del-1 indicates that this portion of the molecule may bind cell surface integrins, possibly triggering certain developmental events. In particular, Del-1 is shown to bind to integrin αVβ3 on endothelial cells. In several cases, synthetic peptides containing the RGD sequence have been shown to compete with native protein for integrin binding and prevent the initiation of downstream events (Brooks et al., 1994, *Cell* 79:1157).

For clarity of discussion, the invention is described in the subsections below by way of example for the del-1 genes and their products in mice and in humans. However, the findings disclosed herein may be analogously applied to other members of the del-1 family in all species.

5.1 The DEL-1 Coding Sequence

The present invention relates to nucleic acid molecules and polypeptides of the del-1 gene family. In a specific embodiment by way of example in Section 6, infra, murine and human del-1 nucleic acid molecules were cloned, and their nucleotide and deduced amino acid sequences characterized. Both the nucleotide coding sequence and deduced amino acid sequence of del-1 are unique. In accordance with the invention, any nucleotide sequence which encodes the amino acid sequence of the del-1 gene product can be used to generate recombinant molecules which direct the expression of del-1 gene.

Enhancer trapping is a strategy which has been successfully employed in genetic analysis in *Drosophila* but is also applicable to higher organisms. This method identifies regulatory regions in genomic loci through their influence on reporter genes (Okane et al., 1987, *Proc. Natl. Acad. Sci. U.S.A.* 84:9123–9127). The reporter gene, as a transcriptional unit under the control of a weak constitutively expressed eukaryotic promoter, is introduced into a large number of organisms. The offsprings of these organisms are then screened by analysis of the pattern of reporter gene expression. Lines which show expression in the appropriate cells at the appropriate time are maintained for further study. This strategy has successfully identified a number of loci in *Drosophila* involved in complex developmental processes.

Enhancer trap experiments have been employed in mice to a limited extent (Allen et al., 1988, *Nature* 333:852–855). A number of such experiments were through fortuitous integration of a reporter gene into a locus of interest (Kothary et al., 1988, *Nature* 335:435–437). Using this method coupled with genomic and cDNA cloning, the murine del-1 locus associated with the transgene was identified. A genomic library is generated from the transgenic mouse, and a probe from the transgene used to isolate clones containing the transgene and sequences flanking the integration site. Characterization of the regulatory region is accomplished by employing flanking sequences in functional assays, via transfection experiments with an appropriate cell culture line, or via further transgenic experiments (Bhat et al., 1988, *Mol. Cell. Biol.* 8:3251–3259).

For analysis of the transcription unit, it is necessary to identify a region of flanking sequence which contains a portion of exon. This has been accomplished by blindly using flanking genomic sequences as probes in northern blots or zoo blots (Soinen et al., 1992, *Mechanisms of Development* 39:111–123). DNA fragments thus identified to contain exon sequence are employed as probes for cDNA cloning. Similar cloning experiments have been conducted to characterize loci inactivated by insertional mutagenesis associated with transgene integration. These experiments indicate that deletions of large regions of genomic DNA may accompany transgene integration, and that complexity of the transcription unit may greatly complicate this type of analysis (Karls et al., 1992, *Mol. Cell. Biol.* 12:3644–3652; Woychik et al., 1990, *Nature* 346:850–853).

Subsequent analysis of the del-1 sequence has revealed both EGF-like and discoidin I/factor VIII-like domains. The shared homology between del-1 and other known molecules is discussed in Section 6.2, infra. However, this molecule also contains regions of previously unreported unique nucleotide sequences. Northern blot hybridization analysis indicates that del-1 mRNA is highly expressed in fetal cells. In addition, the del-1 sequence is expressed in certain tumor cells.

In order to clone the full length cDNA sequence from any species encoding the entire del-1 cDNA or to clone variant forms of the molecule, labeled DNA probes made from nucleic acid fragments corresponding to any murine and human of the partial cDNA disclosed herein may be used to screen a cDNA library. More specifically, oligonucleotides corresponding to either the 5' or 3' terminus of the cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCl, pH 7.5, before being allowed to air dry. The filters are prehybridized in casein hybridization buffer containing 10% dextran sulfate, 0.5M NaCl, 50 mM Tris HCl, pH 7.5, 0.1% sodium pyrophosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography. After developing, film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage well may then be replated and rescreened to obtain single, well isolated positive plaques. Positive plaques may be isolated and the cDNA clones sequenced using primers based on the known cDNA sequence. This step may be repeated until a full length cDNA is obtained.

It may be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. 5'-RACE-Ready cDNA synthesized from human fetal liver containing a unique anchor sequence is commercially available (Clontech). To obtain the 5' end of the cDNA, PCR is carried out on 5'-RACE-Ready cDNA using the provided anchor primer and the 3' primer. A secondary PCR reaction is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, EGF-like domain, discoidin I-like domain, a potential signal sequence and transmembrane domain, and finally overall structural similarity to the del-1 genes disclosed herein.

5.2 Expression of DEL-1 Sequence

In accordance with the invention, a del-1 polynucleotide sequence which encodes the Del-1 protein, mutant polypeptides, peptide fragments of Del-1, Del-1 fusion proteins or functional equivalents thereof, may be used to generate recombinant DNA molecules that direct the expression of Del-1 protein, Del-1 peptide fragments, fusion proteins or a functional equivalent thereof, in appropriate host cells. Such del-1 polynucleotide sequences, as well as other polynucleotides which selectively hybridize to at least a part of such del-1 polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the Del-1 protein. Such DNA sequences include those which are capable of hybridizing to the murine and/or human del-1 sequences under stringent conditions. The phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a Del-1 sequence, which result in a silent change thus producing a functionally equivalent Del-1 protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter a del-1 coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc.

Based on the domain organization of the Del-1 protein, a large number of Del-1 mutant polypeptides can be constructed by rearranging the nucleotide sequences that encode the Del-1 domains. Since the EGF-like domains of Del-1 are known to be involved in protein binding, Del-1 may directly bind to other cell surface receptors or extracellular matrix proteins via these domains, thereby controlling cell fate determination or differentiation in a manner similar to Notch and Notch ligands. Additionally, the RGD sequence in the second EGF-like domain is known to bind to certain integrins, thus Del-1 may regulate cell adhesiveness, migration, differentiation and viability via this sequence. The discoidin I-like domains of Del-1 are involved in a separate type of cell binding activity. In accordance with the observed properties of Factors V and VIII, Del-1 may directly bind proteoglycans in the extracellular matrix or on the cell surface via those domains. Therefore, the combination of various domains of full-length Del-1 permits the molecule to perform diverse types of binding. For example, the major form of Del-1 may be able to cluster integrin receptors by way of both EGF-like and discoidin I-like domains. In contrast, smaller fragments of Del-1 or its minor form would bind integrins without the ability to induce receptor clustering, and thus induce alternative signals to cells.

In view off the foregoing, the Del-1 mutant polypeptides can be generated and their functional activities compared. In addition to the minor form, Del-1 mutants may be constructed to contain only the EGF-like or discoidin I-like domains. Additionally, smaller polypeptides can be made from constructs that contain any one of the EGF-like and discoidin I-like domains.

In another embodiment of the invention, a del-1 or a modified del-1 sequence may be ligated to a heterologous sequence to encode a fusion protein. For example, for screening of peptide libraries for molecules that bind Del-1, it may be useful to encode a chimeric Del-1 protein expressing a heterologous epitope that is recognized by a commercially available antibody. A fusion protein may also be engineered to contain a cleavage site located between a Del-1 sequence and the heterologous protein sequence, so that the Del-1 may be cleaved away from the heterologous moiety.

In an alternate embodiment of the invention, the coding sequence of Del-1 could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10): 2331; Matteucci and Caruthers, 1980, *Tetrahedron Letter* 21:719, and Chow and Kempe, 1981, *Nuc. Acids Res.* 9(12):2807–2817. Alternatively, the protein itself could be produced using chemical methods to synthesize a Del-1 amino acid sequence in whole or in part. For example, peptides can be synthesized by solid phase techniques, cleaved from the resin, and purified by preparative high performance liquid chromatography. (e.g., see Creighton, 1983, *Proteins Structures and Molecular Principles*, W.H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles*, W.H. Freeman and Co., N.Y., pp. 34–49).

In order to express a biologically active Del-1, the nucleotide sequence coding for Del-1, or a functional equivalent, is inserted into an appropriate expression vector, i.e., a vector which contains the necessary elements for the transcription and translation of the inserted coding sequence. The del-1 gene products as well as host cells or cell lines transfected or transformed with recombinant del-1 expression vectors can be used for a variety of purposes. These include but are not limited to generating antibodies (i.e., monoclonal or polyclonal) that competitively inhibit activity of Del-1 protein and neutralize its activity; and antibodies that mimic the activity of Del-1 binding partners such as a receptor. Anti-Del-1 antibodies may be used in detecting and quantifying expression of Del-1 levels in cells and tissues such as endothelial cells and certain tumor cells, as well as isolating Del-1 positive cells.

5.3 Expression Systems

Methods which are well known to those skilled in the art can be used to construct expression vectors containing the del-1 coding sequence and appropriate transcriptional/translational control signals. These methods include in vitro recombinant DNA techniques, synthetic techniques and in vivo recombination/genetic recombination. See, for example, the techniques described in Sambrook et al., 1989, *Molecular Cloning A Laboratory Manual*, Cold Spring Harbor Laboratory, N.Y. and Ausubel et al., 1989, *Current Protocols in Molecular Biology*, Greene Publishing Associates and Wiley Interscience, N.Y.

A variety of host-expression vector systems may be utilized to express the del-1 coding sequence. These include but are not limited to microorganisms such as bacteria transformed with recombinant bacteriophage DNA, plasmid DNA or cosmid DNA expression vectors containing the del-1 coding sequence; yeast transformed with recombinant yeast expression vectors containing the del-1 coding sequence; insect cell systems infected with recombinant virus expression vectors (e.g., baculovirus) containing the del-1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the del-1 coding sequence; or animal cell systems. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the del-1 DNA, SV40-, BPV- and EBV-based vectors may be used with an appropriate selectable marker.

In bacterial systems a number of expression vectors may be advantageously selected depending upon the use intended for the del-1 expressed. For example, when large quantities of del-1 are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, *EMBO J.* 2:1791), in which the del-1 coding sequence may be ligated into the vector in frame with the lacZ coding region so that a hybrid AS-lacZ protein is produced; pIN vectors (Inouye & Inouye, 1985, *Nucleic acids Res.* 13:3101–3109; Van Heeke & Schuster, 1989, *J. Biol. Chem.* 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety. In particular, murine del-1 major and minor coding sequences have been inserted in pET28a (Novagen Inc.) which contains a T7 promoter, and pMALC2 (New England Biolabs). These vectors encode fusion proteins which can be readily purified.

In yeast, a number of vectors containing constitutive or inducible promoters may be used. For a review see, *Current Protocols in Molecular Biology*, Vol. 2, 1988, Ed. Ausubel et al., Greene Publish. Assoc. & Wiley Interscience, Ch. 13; Grant et al., 1987, *Expression and Secretion Vectors for Yeast*, in Methods in Enzymology, Eds. Wu & Grossman, 1987, Acad. Press, N.Y., Vol. 153, pp. 516–544; Glover, 1986, *DNA Cloning*, Vol. II, IRL Press, Wash., D.C., Ch. 3; and Bitter, 1987, *Heterologous Gene Expression in Yeast*, Methods in Enzymology, Eds. Berger & Kimmel, Acad. Press, N.Y., Vol. 152, pp. 673–684; and *The Molecular Biology of the Yeast Saccharomyces*, 1982, Eds. Strathern et al., Cold Spring Harbor Press, Vols. I and II.

In cases where plant expression vectors are used, the expression of the del-1 coding sequence may be driven by any of a number of promoters. For example, viral promoters such as the $^{35}$S RNA and 19S RNA promoters of CaMV (Brisson et al. 1984, *Nature* 310:511–514), or the coat protein promoter of TMV (Takamatsu et al., 1987, *EMBO J.*

6:307–311) may be used; alternatively, plant promoters such as the small subunit of RUBISCO (Coruzzi et al., 1984, *EMBO J.* 3:1671–1680; Broglie et al., 1984, *Science* 224: 838–843); or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, *Methods for Plant Molecular Biology*, Academic Press, NY, Section VIII, pp. 421–463; and Grierson & Corey, 1988, *Plant Molecular Biology*, 2d Ed., Blackie, London, Ch. 7–9.

An alternative expression system which could be used to express del-1 is an insect system. In one such system, *Autographa californica* nuclear polyhedrosis virus (AcNPV) is used as a vector to express foreign genes. The virus grows in *Spodoptera frugiperda* cells. The del-1 coding sequence may be cloned into non-essential regions (for example the polyhedrin gene) of the virus and placed under control of an AcNPV promoter (for example the polyhedrin promoter). Successful insertion of the del-1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, *J. Viol.* 46:584; Smith, U.S. Pat. No. 4,215,051). A commercially available baculovirus expression vector pFastBac 1 (Gibco BRL, Inc.) has been constructed to contain the murine del-1 coding sequence.

In mammalian host cells, a number of viral based expression systems may be utilized. In cases where an adenovirus is used as an expression vector, the del-1 coding sequence may be ligated to an adenovirus transcripton/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing del-1 in infected hosts. (e.g., See Logan & Shenk, 1984, *Proc. Natl. Acad. Sci. USA* 81:3655–3659). Alternatively, the vaccinia 7.5K promoter may be used. (See, e.g., Mackett et al., 1982, *Proc. Natl. Acad. Sci. USA* 79:7415–7419; Mackett et al., 1984, *J. Virol.* 49:857–864, Panicali et al., 1982, *Proc. Natl. Acad. Sci. USA* 79:4927–4931).

Additionally, both the murine del-1 and human coding sequences have been inserted in a mammalian expression vector, pcDNA3 (Invitrogen, Inc.), which is under the control of the cytomegalovirus promoter. Regulatable expression vectors such as the tetracycline inducible vectors may also be used to express the coding sequences in a controlled fashion.

Specific initiation signals may also be required for efficient translation of inserted del-1 coding sequences. These signals include the ATG initiation codon and adjacent sequences. In cases where the entire del-1 gene, including its own initiation codon and adjacent sequences, is inserted into the appropriate expression vector, no additional translational control signals may be needed. However, in cases where only a portion of the del-1 coding sequence is inserted, exogenous translational control signals, including the ATG initiation codon, must be provided. Furthermore, the initiation codon must be in phase with the reading frame of the del-1 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of several consensus N-glycosylation sites in the del-1 extracellular domain support the possibility that proper modification may be important for Del-1 function. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, W138, yolk sac cells, etc.

For long term, high-yield production of recombinant proteins, stable expression is preferred. For example, cell lines which stably express the del-1 may be engineered. Rather than using expression vectors which contain viral origins of replication, host cells can be transformed with the del-1 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Del-1 protein on the cell surface. Such engineered cell lines are particularly useful in screening for molecules or drugs that affect del-1 function.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowry, et al., 1980, *Cell* 22:817) genes can be employed in tk-, hgprt- or aprt-cells, respectively. Also, antimetabolite resistance can be used as the basis of selection for dhfr, which confers resistance to methotrexate (Wigler, et al., 1980, *Proc. Natl. Acad. Sci. USA* 77:3567; O'Hare, et al., 1981, *Proc. Natl. Acad. Sci. USA* 78:1527); gpt, which confers resistance to mycophenolic acid (Mulligan & Berg, 1981), *Proc. Natl. Acad. Sci. USA* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85:8047) and ODC (ornithine decarboxylase) which confers resistance to the ornithine decarboxylase inhibitor, 2-(difluoromethyl)-DL-ornithine, DFMO (McConlogue L., 1987, In: *Current Communications in Molecular Biology*, Cold Spring Harbor Laboratory ed.).

5.4 Identification of Cells that Express DEL-1

The host cells which contain the coding sequence and which express a biologically active del-1 gene product or fragments thereof may be identified by at least four general approaches; (a) DNA-DNA or DNA-RNA hybridization, (b) the presence or absence of "marker" gene functions; (c) assessing the level of transcription as measured by the expression of del-1 mRNA transcripts in the host cell; and (d) detection of the gene product as measured by immunoassay or by its biological activity. Prior to the identification of gene expression, the host cells may be first mutagenized in an effort to increase the level of expression of del-1, especially in cell lines that produce low amounts of del-1.

In the first approach, the presence of the del-1 coding sequence inserted in the expression vector can be detected by DNA-DNA or DNA-RNA hybridization using probes comprising nucleotide sequences that are homologous to the del-1 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, the del-1 coding sequence is inserted within a marker gene sequence of the vector, recombinants containing the del-1 coding sequence can be identified by the absence of the marker gene function. Alternatively, a marker gene can be placed in tandem with the del-1 sequence under the control of the same or different promoter used to control the expression of the del-1 coding sequence. Expression of the marker in response to induction or selection indicates expression of the del-1 coding sequence.

In the third approach, transcriptional activity for the del-1 coding region can be assessed by hybridization assays. For example, RNA can be isolated and analyzed by Northern blot using a probe homologous to the del-1 coding sequence or particular portions thereof. Alternatively, total nucleic acids of the host cell may be extracted and assayed for hybridization to such probes. Additionally, RT-PCR may be used to detect low-levels of gene expression.

In the fourth approach, the expression of the Del-1 protein product can be assessed immunologically, for example by Western blots, immunoassays such as radioimmunoprecipitation, enzyme-linked immunoassays and the like. This can be achieved by using an anti-Del-1 antibody and a Del-1 binding partner such as αVβ3. Alternatively, the biologic activities of Del-1 can be determined by assaying its ability to inhibit vascular morphogenesis of endothelial cells.

5.5 Uses of DEL-1 Engineered Cell Lines

In an embodiment of the invention, the Del-1 protein and/or cell lines that express Del-1 may be used to screen for antibodies, peptides, small molecules natural and synthetic compounds or other cell bound or soluble molecules that bind to the Del-1 protein. For example, anti-Del-1 antibodies may be used to inhibit or stimulate Del-1 function. Alternatively, screening of peptide libraries with recombinantly expressed soluble Del-1 protein or cell lines expressing Del-1 protein may be useful for identification of therapeutic molecules that function by inhibiting or stimulating the biological activity of Del-1. The uses of the Del-1 protein and engineered cell lines, described in the subsections below, may be employed equally well for other members of the del-1 gene family in various species.

In an embodiment of the invention, engineered cell lines which express most of the del-1 coding region or a portion of it fused to another molecule such as the immunoglobulin constant region (Hollenbaugh and Aruffo, 1992, *Current Protocols in Immunology*, Unit 10.19, Aruffo et al., 1990, *Cell* 61:1303) may be utilized to produce a soluble molecule to screen and identify its binding partners. The soluble protein or fusion protein may be used to identify such a molecule in binding assays, affinity chromatography, immunoprecipitation, Western blot, and the like. Alternatively, portions of del-1 may be fused to the coding sequence of the EGF receptor transmembrane and cytoplasmic regions. Assuming that Del-1 can function as a cell-bound receptor, this approach provides for the use of the EGF receptor signal transduction pathway as a means for detecting molecules that bind to Del-1 in a manner capable of triggering an intracellular signal. On the other hand, Del-1 may be used as a soluble factor in binding to cell lines that express specific known receptors such as integrins. Synthetic compounds, natural products, and other sources of potentially biologically active materials can be screened in assays that are well known in the art.

Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, *Nature* 354:82–84). The screening of peptide libraries may have therapeutic value in the discovery of pharmaceutical agents that stimulate or inhibit the biological activity of receptors through their interactions with the given receptor.

Identification of molecules that are able to bind to the Del-1 protein may be accomplished by screening a peptide library with recombinant soluble Del-1 protein. Methods for expression and purification of Del-1 are described in Section 5.2, supra, and may be used to express recombinant full length del-1 or fragments of del-1 depending on the functional domains of interest. For example, the EGF-like and discoidin I/factor VIII domains of del-1 may be separately expressed and used to screen peptide libraries.

To identify and isolate the peptide/solid phase support that interacts and forms a complex with Del-1, it is necessary to label or "tag" the Del-1 molecule. The Del-1 protein may be conjugated to enzymes such as alkaline phosphatase or horseradish peroxidase or to other reagents such as fluorescent labels which may include fluorescein isothiocyanate (FITC), phycoerythrin (PE) or rhodamine. Conjugation of any given label to Del-1 may be performed using techniques that are well known in the art. Alternatively, del-1 expression vectors may be engineered to express a chimeric Del-1 protein containing an epitope for which a commercially available antibody exists. The epitope specific antibody may be tagged using methods well known in the art including labeling with enzymes, fluorescent dyes or colored or magnetic beads.

The "tagged" Del-1 conjugate is incubated with the random peptide library for 30 minutes to one hour at 22° C. to allow complex formation between Del-1 and peptide species within the library. The library is then washed to remove any unbound protein. If Del-1 has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3,3',4,4"-diaminobenzidine (DAB), respectively. After incubating for several minutes, the peptide/solid phase-Del-1 complex changes color, and can be easily identified and isolated physically under a dissecting microscope with a micromanipulator. If a fluorescent tagged Del-1 molecule has been used, complexes may be isolated by fluorescence activated sorting. If a chimeric Del-1 protein expressing a heterologous epitope has been used, detection of the peptide/Del-1 complex may be accomplished by using a labeled epitope specific antibody. Once isolated, the identity of the peptide attached to the solid phase support may be determined by peptide sequencing.

In addition to using soluble Del-1 molecules, in another embodiment, it is possible to detect peptides that bind to cell surface receptors using intact cells. The use of intact cells is preferred for use with receptors that are multi-subunits or labile or with receptors that require the lipid domain of the cell membrane to be functional. Methods for generating cell lines expressing del-1 are described in Section 5.3. The cells used in this technique may be either live or fixed cells. The cells may be incubated with the random peptide library and bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

Various procedures known in the art may be used for the production of antibodies to epitopes of the natural and recombinantly produced Del-1 protein. Such antibodies include but are not limited to polyclonal, monoclonal, chimeric, single chain, Fab fragments and fragments produced by a Fab expression library. Neutralizing antibodies, i.e., those which compete for the ligand binding site of the Del-1 protein are especially preferred for diagnostics and therapeutics.

Monoclonal antibodies that bind Del-1 may be radioactively labeled allowing one to follow their location and distribution in the body after injection. Radioisotope tagged antibodies may be used as a non-invasive diagnostic tool for imaging de novo cells of tumors and metastases.

Immunotoxins may also be designed which target cytotoxic agents to specific sites in the body. For example, high affinity Del-1 specific monoclonal antibodies may be covalently complexed to bacterial or plant toxins, such as diphtheria toxin, ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Del-1 expressing tumor cells.

For the production of antibodies, various host animals may be immunized by injection with the recombinant or naturally purified Del-1 protein, fusion protein or peptides, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*bacilli* Calmette-Guerin) and *Corynebacterium parvum*.

Monoclonal antibodies to Del-1 may be prepared by using any technique which provides for the production of antibody molecules by continuous cell lines in culture. These include but are not limited to the hybridoma technique originally described by Kohler and Milstein, (*Nature*, 1975, 256: 495–497), the human B-cell hybridoma technique (Kosbor et al., 1983, *Immunology Today*, 4:72; Cote et al., 1983, *Proc. Natl. Acad. Sci.*, 80:2026–2030) and the EBV-hybridoma technique (Cole et al., 1985, *Monoclonal and Cancer Therapy*, Alan R. Liss, Inc., pp. 77–96). In addition, techniques developed for the production of "chimeric antibodies" (Morrison et al., 1984, *Proc. Natl. Acad. Sci.*, 81:6851–6855; Neuberger et al., 1984, *Nature*, 312:604–608; Takeda et al., 1985, *Nature*, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce Del-1 specific single chain antibodies.

Hybridomas may be screened using enzyme-linked immunosorbent assays (ELISA) in order to detect cultures secreting antibodies specific for refolded recombinant Del-1. Cultures may also be screened by ELISA to identify those cultures secreting antibodies specific for mammalian-produced Del-1. Confirmation of antibody specificity may be obtained by western blot using the same antigens. Subsequent ELISA testing may use recombinant Del-1 fragments to identify the specific portion of the Del-1 molecule with which a monoclonal antibody binds. Additional testing may be used to identify monoclonal antibodies with desired functional characteristics such as staining of histological sections, immunoprecipitation of Del-1, or neutralization of Del-1 activity. Determination of the monoclonal antibody isotype may be accomplished by ELISA, thus providing additional information concerning purification or function.

Antibody fragments which contain specific binding sites of Del-1 may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, *Science*, 246:1275–1281) to allow rapid and easy identification of monoclonal Fab fragments with the desired specificity to Del-1. Anti-Del-1 antibodies may be used to isolate Del-1-expressing cells or eliminate such cells from a cell mixture.

5.6 Uses of DEL-1 Polypeptide.

A del-1 polynucleotide may be used for diagnostic and/or therapeutic purposes. For diagnostic purposes, a del-1 polynucleotide may be used to detect del-1 gene expression or aberrant del-1 gene expression in disease states. Included in the scope of the invention are oligonucleotide sequences, that include antisense RNA and DNA molecules and ribozymes, that function to inhibit translation of del-1.

5.6.1 Diagnostic Used of a DEL-1 Polypeptide

A del-1 polynucleotide may have a number of uses for the diagnosis of diseases resulting from aberrant expression of del-1. For example, the del-1 DNA sequence may be used in hybridization assays of biopsies or autopsies to diagnose abnormalities of del-1 expression; e.g., Southern or Northern analysis, including in situ hybridization assays. Such techniques are well known in the art, and are in fact the basis of many commercially available diagnostic kits.

5.6.2 Therapeutic Uses of a DEL-1 Polypeptide

A del-1 polynucleotide may be useful in the treatment of various abnormal conditions. By introducing gene sequences into cells, gene therapy can be used to treat conditions in which the cells do not proliferate or differentiate normally due to underexpression of normal del-1 or expression of abnormal/inactive del-1. In some instances, the polynucleotide encoding a del-1 is intended to replace or act in the place of a functionally deficient endogenous gene. Alternatively, abnormal conditions characterized by overproliferation can be treated using the gene therapy techniques described below.

Abnormal cellular proliferation is an important component of a variety of disease states. Recombinant gene therapy vectors, such as viral vectors, may be engineered to express variant, signaling incompetent forms of Del-1 which may be used to inhibit the activity of the natural occurring endogenous Del-1. A signaling incompetent form may be, for example, a truncated form of the protein that is lacking all or part of its signal transduction domain. Such a truncated form may participate in normal binding to a substrate but lack signal transduction activity. Thus recombinant gene therapy vectors may be used therapeutically for treatment of diseases resulting from aberrant expression or activity of a Del-1. Accordingly, the invention provides a method of inhibiting the effects of signal transduction by an endogenous Del-1 protein in a cell comprising delivering a DNA molecule encoding a signaling incompetent form of the Del-1 protein to the cell so that the signaling incompetent Del-1 protein is produced in the cell and competes with the endogenous Del-1 protein for access to molecules in the Del-1 protein signaling pathway which activate or are activated by the endogenous Del-1 protein.

Expression vectors derived from viruses such as retroviruses, vaccinia virus, adeno-associated virus, herpes viruses, or bovine papilloma virus, may be used for delivery of recombinant Del-1 into the targeted cell population. Methods which are well known to those skilled in the art can be used to construct recombinant viral vectors containing a del-1 polynucleotide sequence. See, for example, the techniques described in Maniatis et al., 1989, *Molecular Cloning: A Laboratory Manual*, Cold Spring Harbor Laboratory, N.Y. and Ausubel et al., 1989, *Current Protocols in Molecular Biology*, Greene Publishing Associates and Wiley Interscience, N.Y. Alternatively, recombinant Del-1 molecules can be reconstituted into liposomes for delivery to target cells.

Oligonucleotide sequences, that include anti-sense RNA and DNA molecules and ribozymes that function to inhibit the translation of a del-1 mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of a del-1 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of del-1 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Methods for introducing polynucleotides into such cells or tissue include methods for in vitro introduction of polynucleotides such as the insertion of naked polynucleotide, i.e., by injection into tissue, the introduction of a del-1 polynucleotide in a cell ex vivo, i.e., for use in autologous cell therapy, the use of a vector such as a virus, retrovirus, phage or plasmid, etc. or techniques such as electroporation which may be used in vivo or ex vivo.

5.7 Uses of DEL-1 Protein

Analysis of β-gal expression in transgenic mice in which β-gal gene expression is controlled by the del-1 enhancer indicates that the del-1 gene is activated in endothelial cells undergoing vasculogenesis. Vasculogenesis refers to the development of blood vessels de novo from embryonic precursor cells. The related process of angiogenesis is the process through which existing blood vessels arise by outgrowth from preexisting ones. Vasculogenesis is limited to the embryo while angiogenesis continues throughout life as a wound healing response or to increase oxygenation of chronically stressed tissues (Pardanaud et al., 1989 *Development* 105:473; Granger 1994, *Cell and Mol. Biol. Res.* 40:81).

It is likely that Del-1 functions during embryonic vasculogenesis and in angiogenesis. For therapeutic use, it is essential that Del-1, portions of Del-1 or antibodies that block Del-1, may interact with angiogenic cells since it is stimulation or inhibition of these cells that is clinically relevant. Manipulation of Del-1 function may have significant effects on angiogenesis if Del-1 normally participates in this process.

The working examples in Sections 9 and 10 demonstrate that Del-1 exhibits an inhibitory effect on angiogenesis, which may be mediated by its interaction with αVβ3-expressing endothelial cells. Del-1 protein or recombinant proteins consisting of portions of Del-1 may function to suppress angiogenesis or induce endothelial cell apoptosis. This function could be clinically useful to prevent neovascularization of tissues such as tumor nodules. It has been demonstrated that inhibition of angiogenesis is useful in preventing tumor metastases (Fidler and Ellis, 1994, *Cell* 79:185). Recently, O'Reilly et al. (1994, *Cell* 79:315) reported that a novel angiogenesis inhibitor isolated from tumor-bearing mice, angiostatin, specifically inhibited endothelial cell proliferation. In vivo, angiostatin was a potent inhibitor of neovascularization and growth of tumor metastases. In a related report, Brooks et al. (1994, *Cell* 79:115) showed that integrin antagonists promoted tumor regression by inducing apoptosis of angiogenic blood vessels. These integrin antagonists included cyclic peptides containing an RGD amino acid sequence. Since Del-1 contains an RGD sequence, the use of this portion of the Del-1 molecule may have similar effects.

Manipulation of the discoidin I/factor VIII-like domains of Del-1 may also be used to inhibit angiogenesis. Apolipoprotein E (ApoE) has been shown to inhibit basic fibroblast growth factor (bFGF)-stimulated proliferation of endothelial cells in vitro (Vogel et al., 1994, *J. Cell. Biochem.* 54:299). This effect could also be produced with synthetic peptides based on a portion of the ApoE sequence. These results could be due to direct competition of ApoE with growth factors for binding to heparin sulfate proteoglycans, or through disruption by ApoE of cell-matrix interactions. It has been proposed that discoidin I/factor VIII-like domains such as those in Del-1 bind to proteoglycans. In addition, Del-1 is similar in structure to a number of extracellular matrix proteins. Thus, Del-1 may manipulated to effect the activity of growth factors such as bFGF or to alter interactions between endothelial cells and the extracellular matrix.

The anti-angiogenic activity of Del-1 may be used to treat abnormal conditions that result from angiogenesis. These conditions include, but are not limited to, cancer, diabetic retinopathy, rheumatoid arthritis and endometriosis. Additionally, the removal or inhibition of Del-1 in situations where it naturally inhibits blood vessel formation may be used to promote angiogenesis. These conditions include, but are not limited to, cardiac ischemia, thrombotic stroke, wound healing and peripheral vascular disease. Furthermore, Del-1 may be used to stimulate bone formation.

6. EXAMPLE

Molecular Cloning of Human and Murine DEL-1 Nucleotide Sequences 6.1. Materials and Methods
6.1.1. Generation of Transgenic Mice The SLM275 transgenic mouse line was generated in a C57BL6×DBA/F1 background, and the transgenic animals had been crossed back against similar B6D2F1 animals for maintenance of the line and the generation of embryos. This transgene had been maintained in the heterozygous state, and these heterozygous mice had normal breeding capacity. However, preliminary experiments indicated that these animals were not viable in the homozygous state.

6.1.2. Molecular Cloning of DEL-1

A genomic library was constructed from high molecular weight DNA isolated from the kidney of an SLM275 transgenic animal. This DNA was subjected to partial digestion with Sau3A to obtain an average size of 20 kb, subjected to a partial fill-in reaction, and then cloned into a similarly treated lambdaphage vector (lambdaFix, Stratagene). The library constructed in this fashion had a base of approximately 2 million clones. These clones were amplified and the library stored at −70° C. A 200 basepair (bp) probe derived from the SV40 polyadenylation signal of the transgene was used as a probe and allowed the isolation of 12 lambdaphage clones. Six of these clones were randomly chosen for further investigation. These clones were mapped, and restriction fragments which did not contain transgene sequence identified. The clones were divided into two groups on the basis of common non-transgenic fragments. One such fragment from the first group of phage allowed specific hybridization to genomic blots and provided evidence that it was derived from a region adjacent to the integration site. Genomic DNA from a non-transgenic mouse of the same genetic background (B6D2 µl) was compared to that of an SLM275 transgene animal by hybridization to this probe. Rearranged bands representing fragments disrupted by transgene integration were seen in the SLM275 lanes with both EcoR1 and BamH1 digests. The flanking sequence probe was employed to screen a commercially available lambdaFixII genomic library constructed from the 129SV mouse strain (Stratagene).

A murine cDNA fragment was used as a probe to identify cDNA clones of its human homolog. The probe corresponded to nucleotides 1249 through 1566 in the murine del-1 major sequence. Human cDNA clones were isolated from a human fetal lung cDNA library (Clontech, Inc.) following standard procedures.

6.2 Results

A transgenic mouse line was created through a fortuitous enhancer trap event. The original studies were designed to map the cell-specific and developmental-specific regulatory regions of the mouse SPARC promoter, 2.2 kilobases (kb) of the SPARC 5' flanking sequence were placed upstream of the *E. coli* lacZ (beta-galactosidase or β-gal) reporter gene. The mouse SPARC gene is normally expressed in a wide variety of adult and embryonic cells which synthesize a specific extracellular matrix (Nomura et al., 1989, *J. Biol. Chem.* 264:12201–12207). However, one of the founder mouse lines showed a highly restricted pattern of expression quite distinct from the native SPARC gene. Expression of the lacZ reporter in this particular line of mice referred to as SLM275 was seen very early in cells of the endothelial lineage. Whole mount lacZ staining was employed for initial studies, and these embryos were subsequently sectioned and examined by light microscopy. The first cells to stain were endothelial cells forming the endocardium, the outflow tract, and the developing intervertebral vessels. Staining appeared to be predominantly restricted to endothelial cells associated with forming major blood vessels. Expression began to decline after 11.5 days pc.

The genomic region targeted by this transgene is herein referred to as del-1. Initial cloning experiments were aimed at isolating genomic sequences flanking the transgene integration site. A number of lambdaphage clones were isolated and mapped (FIG. 1). Approximately 40 kb of the wild-type del-1 sequence was contained in these clones. By probing. Southern blots containing restriction digests of these lambdaphages with non-transgenic fragments from the SLM275 lambdaphage clones, the site of transgene integration was mapped. Insertion of the transgene complex was associated with the deletion of approximately 8 kb of DNA. There were approximately 25 kb of flanking sequence on one side of the integration, and approximately 5 kb of the other flanking sequence contained on these clones.

Exon trapping was used to evaluate genomic fragments for the presence of exons. This approach utilized a vector with a constitutive promoter driving transcription through a DNA fragment containing a splice donor site and a splice acceptor site. Between these splicing signals was a common cloning site where the genomic DNA fragment to be evaluated was cloned. Exons within this fragment would be spliced into the transcript when the construct was transfected into eukaryotic cells, such as COS cells. The transcript containing the trapped exon sequence was rescued from the COS cells by reverse transcriptase polymerase chain reaction (RT-PCR). PCR amplified DNA was cloned and evaluated.

A 160 bp exon was trapped from a fragment of genomic DNA located approximately 10 kb from the "left" integration site. Nucleotide sequence of the trapped exon was employed to screen various nucleic acid databanks through the BLAST routine at the NCBI, revealing no other gene with significant nucleic acid homology. The deduced amino acid sequence of the single open reading frame was subsequently employed in databank searches. These revealed that the protein domain encoded in the trapped exon was similar in part to domains in a number of proteins, including Factor V, Factor VIII and discoidin I (FIG. 2, SEQ ID NOS 1–8) (Jenny et al., 1987, *Proc. Natl. Acad. Sci.* U.S.A. 84:4846–4850; Poole et al., 1981, *J. Mol. Biol.* 153:273–289; Toole et al., 1984, *Nature* 312:342–347) The protein which was most similar was milkfat globule protein, which had been found on the surface of mammary epithelial cells (1994, WO 94/11508). It has been hypothesized that the discoidin I-like domain in this protein allows it to localize to the surface of the epithelial cell (Larocca et al., 1991, *Cancer Res.* 51:4994–4998; Stubbs et al., 1990, *Proc. Natl. Acad. Sci USA.* 87:8417–8421). The homologous regions of Factor V and Factor VIII have been implicated in their interaction with phospholipids on the surface of endothelial cells and platelets (Jenny et al., 1987, *Proc. Natl. Acad. Sci. U.S.A.* 84:4846–4850; Toole et al., 1984, *Nature* 312:342–347). Homology to the *Xenopus* protein A5 was also observed. A5 is a neuronal cell surface molecule which is expressed in retinal neurons and the neurons in the visual center with which the retinal neurons contact (Takagi et al., 1991, *Neuron* 7:295–307). A5 has been proposed to play a role as a neuronal recognition molecule in the development of this neural circuit, perhaps through mediating intercellular signaling. The protein for which this discoidin I-like domain was named is a protein expressed in *Dictyostelium discoideum*, which serves an essential role in the aggregation of individual cells.

The DNA fragment encoding the trapped exon was employed as a probe in a Southern blot experiment and shown to hybridize with regions of the del-1 locus outside of the region that was employed in the exon trap construct. Given this finding, cDNA cloning was pursued by using the exon trap probe to screen an 11.5 day embryonic mouse cDNA library. Clones were plaque purified, and inserts subcloned into plasmid for further analysis. Nucleotide sequence analysis showed that two of the embryonic cDNA clones contained the sequence of the trapped exon. Sequence from the clones was used to expand the deduced amino acid sequence of the discoidin I-like domain (FIG. 2, SEQ ID NOS 1–8). The full nucleotide sequence of these cDNAs was analyzed and cloned into plasmid vectors which allowed the generation of cRNA transcripts for RNAse protection and in situ hybridization (FIG. 3A-3D, SEQ ID NO: 9).

A human cDNA was isolated from a human fetal lung cDNA lambda phage library purchased from Clontech Inc. (FIG. 4A-4C, SEQ ID NO: 11). A portion of the mouse del-1 cDNA was used as a probe (FIG. 5, SEQ ID NO: 19). The identity of the human cDNA clone was confirmed by comparing the human and mouse DNA sequences. These clones show approximately 80% DNA sequence homology and approximately 94% amino acid sequence homology (FIG. 6, SEQ ID NOS: 10 and 30). These sequences are referred to as the "major" form of del-1. Upon initial isolation of del-1, standard molecular biology methods were used for isolating additional clones.

DNA sequence analysis of the human del-1 revealed an open reading frame of 1,446 base pairs predicted to encode a 481 amino acid protein with a molecular weight of, 53,797. The mouse cDNA encodes a 480 amino acid protein. Homology comparisons with DNA and protein databases indicated that the Del-1 protein was composed of three EGF-like protein domains, followed by two discoidin I/factor VIII-like domains (FIG. 7). Genes similar to del-1 included some key regulators of cell determination and differentiation such as Notch. Overall, the Del-1 protein has a structure similar to the membrane-associated milk fat globule membrane protein, MGF-E8, which has been used to develop antibodies for imaging breast cancer (FIG. 8, SEQ ID NOS: 20 and 21).

A physiologic function for the Del-1 protein is implicated by the activities which have been demonstrated for EGF-like and discoidin I/factor VIII-like domains in other proteins. EGF-like domains have been shown to participate in protein-protein binding interactions, while the discoidin I-like domains of factor VIII are believed to mediate binding to cell membranes through association with negatively charged phospholipids. Thus, the Del-1 protein may generate a signal for endothelial cell determination or differentiation by binding to the membranes of precursor cells and interacting with an EGF-like domain receptor protein.

Key structural features of the open reading frame of human Del-1 include:
1) the presumed initiator methionine and putative secretion signal sequence (FIG. 9, SEQ ID NO: 22)
2) the three EGF-like domains (FIG. 10, SEQ ID NOS: 23–25)
3) the two discoidin I-like domains.

Further cloning and analysis of both the human and murine del-1 genes revealed additional variant forms. For example, a human splicing variant (Z20 clone) was obtained in which 30 bp (i.e. 10 amino acids) (SEQ ID: 30 # 66-#75) between the first and second EGF-like domains of the major form (SEQ NO ID: 30) of del-1 had been removed (FIG. 11, SEQ ID NO: 31). In addition, a truncated version of murine del-1 was isolated, which contained a signal peptide sequence, all three EGF-like domains and only a partial amino-terminal discoidin I/factor VIII-like domain (about 40%). This variant is referred to as murine del-1 minor sequence, which is disclosed in FIG. 12A-12D, SEQ ID NOS: 28 and 29. This transcript was cloned only from mouse embryonic libraries, but was verified through cloning of several independent cDNAs.

7. EXAMPLE

Tissue Distribution of DEL-1 Gene Expression 7.1. Materials and Methods 7.1.1. Whole Mount Staining of Transgenic Mouse Embryos Male transgenic animals of second or third generation had been crossed with 8–10 week B6D2F1 females, and embryos harvested at 7.5, 8.5, 9.5, 10.5, and 13.5 days. Timing was based on the convention that noon of the day of plugging was 0.5 day post-coitum (pc). Embryos were harvested, dissected free of decidua and membranes, fixed in 2% glutaraldehyde, and stained as a whole mount in a standard X-gal indicator solution according to standard protocols. An exception was that embryos older than 11.5 days were bisected which allowed better penetration of the fixative and staining solution. Stained tissues were identified in whole mount embryos by examination at 7–70× with an Olympus SZH10 stereomicroscope, and photographed under darkfield illumination. Embryos 7.5, 8.5, 9.5, and 13.5 days pc were embedded in paraffin, sectioned, counterstained with nuclear fast red and examined under brightfield with a Zeiss Axioplan microscope.

7.1.2 Northern Blot Analysis

In order to study the expression of: the del-1 gene, Northern blots containing RNA obtained from a variety of human and mouse tissues (Clontech, Palo Alto, Calif.) were hybridized with a radiolabeled DNA probe as shown in FIG. 5, SEQ ID NO: 19. In addition, adult organs, 15.5 dpc whole embryos and organs dissected from embryos were disrupted with a polytron, and RNA isolated over [$C_s$Cl] CsCl gradient (Sambrook et al., 1989, Molecular Cloning, Laboratory Manual, Cold Spring Harbor Laboratory, NY). Briefly, the blots were prehybridized at 42° C. for 3–6 hours in a solution containing 5× SSPE, 10× Denhardt's solution, 100 µg/ml freshly denatured, sheared salmon sperm DNA, 50% formamide (freshly deionized), and 2% SDS. The radiolabeled probe was heat denatured and added to the prehybridization mix and allowed to hybridize at 42° C. for 18–24 hours with constant shaking. The blots were rinsed in 2×SSC, 0.05% SDS several times at room temperature before being transferred to a wash solution containing 0.1×SSC, 0.1% SDS and agitated at 50° C. for 40 minutes. The blots were then covered with plastic wrap, mounted on Whatman paper and exposed to x-ray film at −70° C. using an intensifying screen.

7.1.3 Reverse Transcription-Polymerase Chain Reaction (RT-PCR)

Total RNA was isolated using standard laboratory procedures (Sambrook et al., 1989, *Molecular Cloning, A Laboratory Manual*, Cold Spring Harbor Laboratory, NY). Approximately 1 µg of total RNA was reverse transcribed and the cDNA was amplified by PCR (Perkin Elmer, Norwalk, Conn.). The PCR amplification conditions were: 94° C. for 30 sec, 60° C. for 30 sec, 72° C. for 30 sec for a total of 40 cycles. The amplified products were resolved by agarose gel electrophoresis and visualized by ethidium bromide staining. The amplimers were:

+strand primer: ACC CAA GGG GCA AAA AGG A (SEQ ID NO: 32)

−strand primer CCT GTA ACC ATT GTG ACT G (SEQ ID NO: 33)

7.2 Results

Expression of del-1 in various human and mouse tissues and cell lines was investigated by whole mount staining, Northern blot analysis and RT-PCR. Results of experiments are summarized in the subsections below.

7.2.1 Expression Analysis by Histochemistry

Figure 13A:
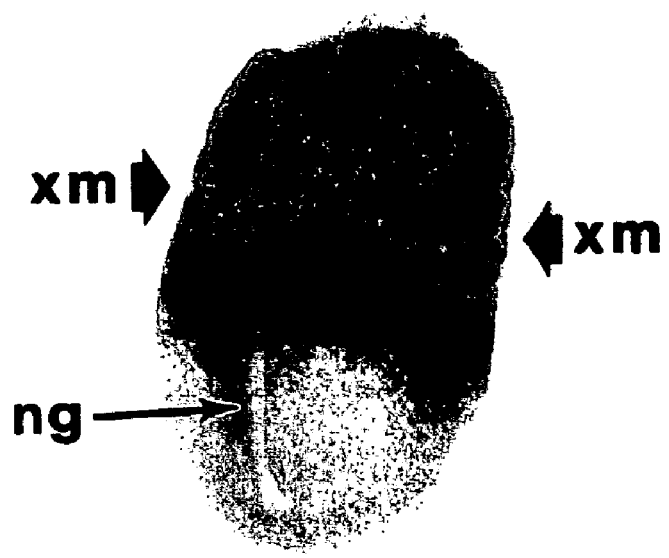

When the earliest time point was investigated by whole mount and histochemical staining in transgenic mice at day 7.5 pc, expression of the lacZ reporter gene was shown in cells forming the extra embryonic mesoderm (FIG. 13A). These cells would form the yolk sac and give rise to cells of the blood island. Expression of the lacZ reporter gene in this locus is thus one of the earliest known markers of the endothelial cell lineage. The only other marker which has been shown to be expressed in precursors of endothelial cells at this early stage of development is the receptor tyrosine kinase flk-1 (Millauer et al., 1993, *Cell* 72:835–846). However, del-1 expression was not found in the allantois, as with other early markers of the endothelium such as flk-1 (Yamaguchi et al., 1993, *Development* 118: 489–498).

Figure 13B:
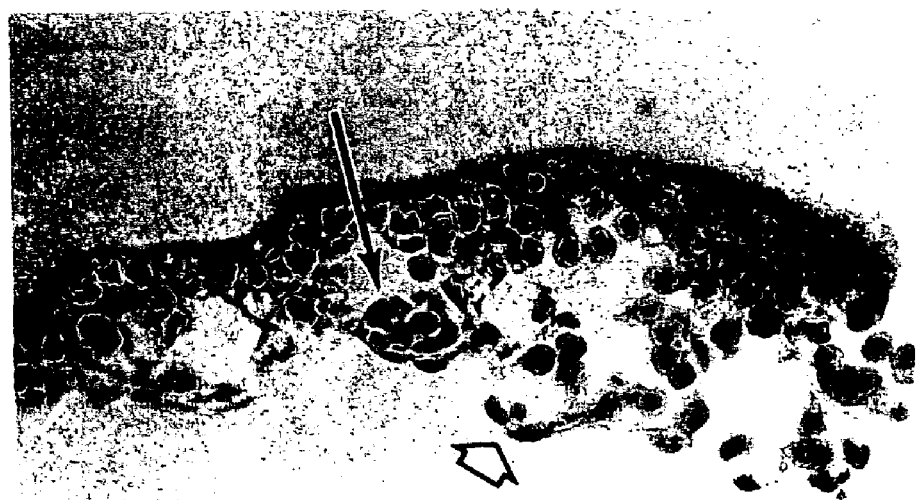
Figure 13C:
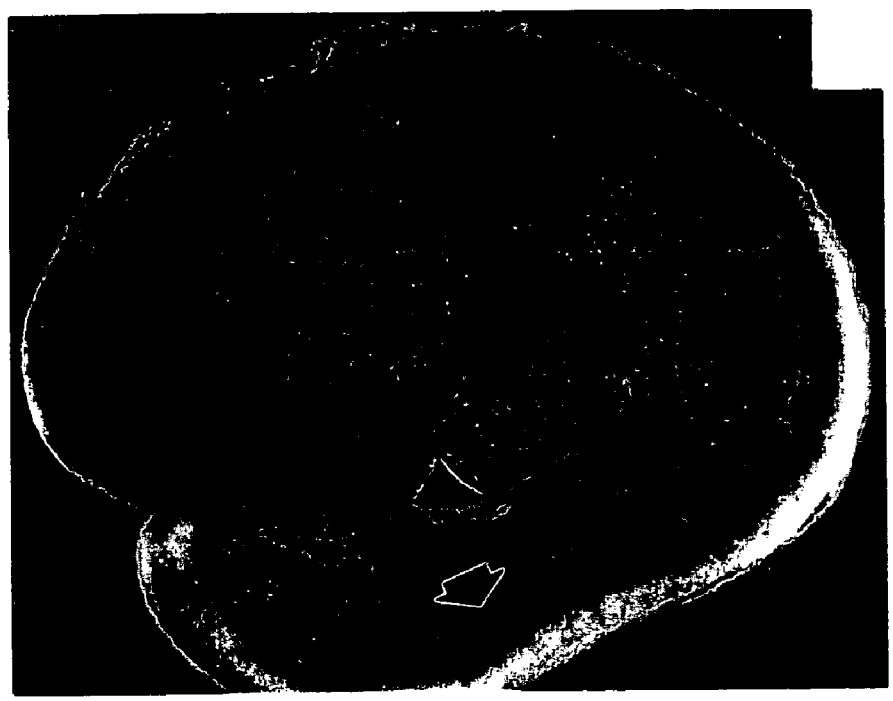
Figure 13D:
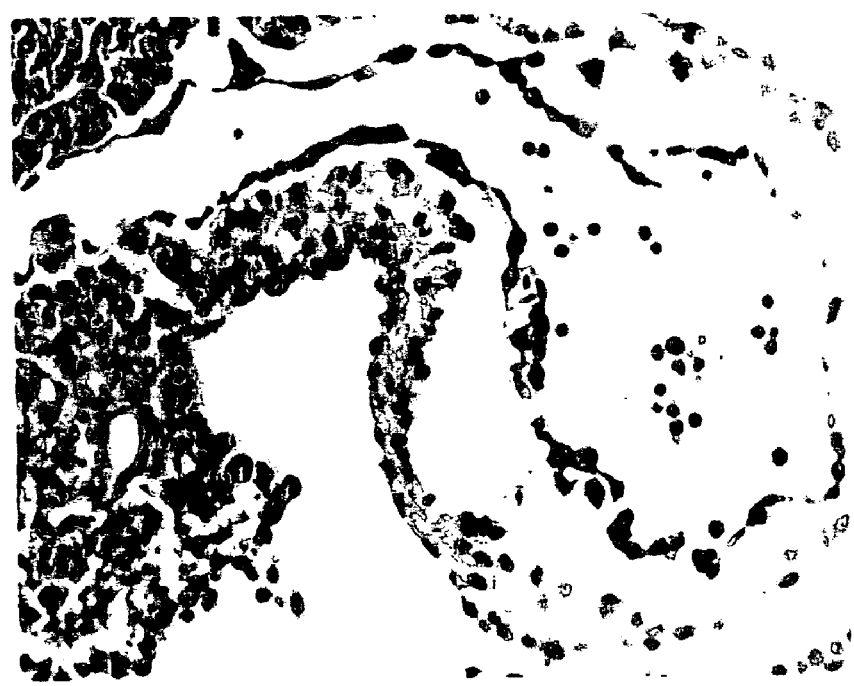

At day 8.5, lacZ staining was seen in cells in the blood islands of the yolk sac. Interestingly, staining was not detected in mature endothelial cells lining the blood island, but rather in round cells found in clumps within the blood island (FIG. 13B). These round cells had large nuclei and were closer in appearance to hematopoietic precursors rather than endothelial cells. This expression pattern was distinct from all other early endothelial markers. Thus, the del-1 locus might be expressed in early embryonic cells which were precursors to both endothelial and hematopoietic lineages. In the late primitive streak stage embryo at 8.5 days pc, there was also staining of endothelial cells associated with the developing paired dorsal aortae. LacZ staining was seen in cells in the region of the forming heart at this stage, and these were presumably endothelial cells that would form the endocardium. By day 9.5 (10–14 somites), the endocardium and endothelial cells forming the outflow tract and aorta showed lacZ staining (FIGS. 13C, 13D). This staining persisted until day 10.5 and 11.5, and by whole mount analysis endothelial cells associated with all large vascular structures were expressing the reporter gene.

Figure 13E:
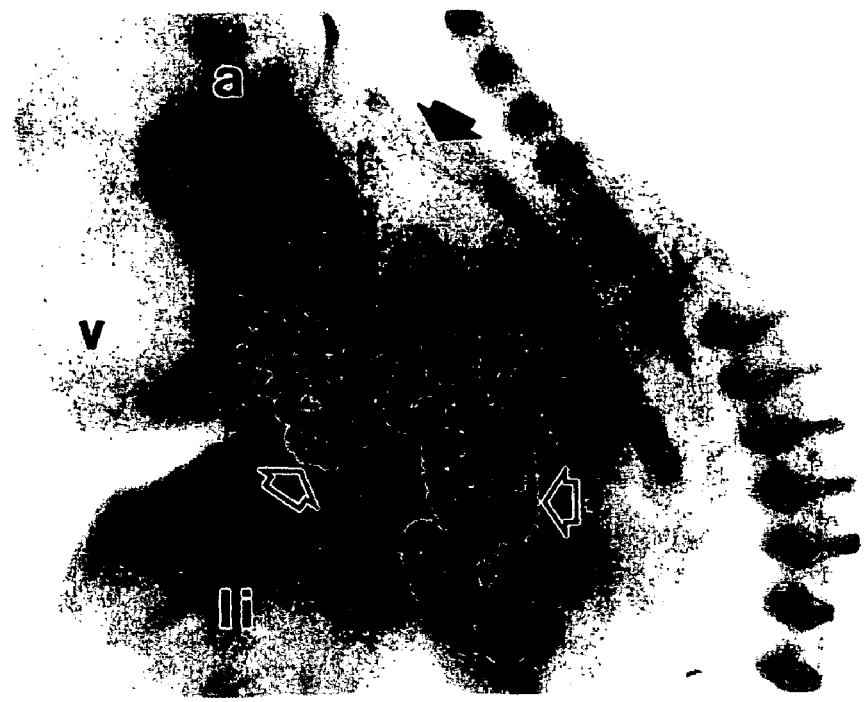
Figure 13F:
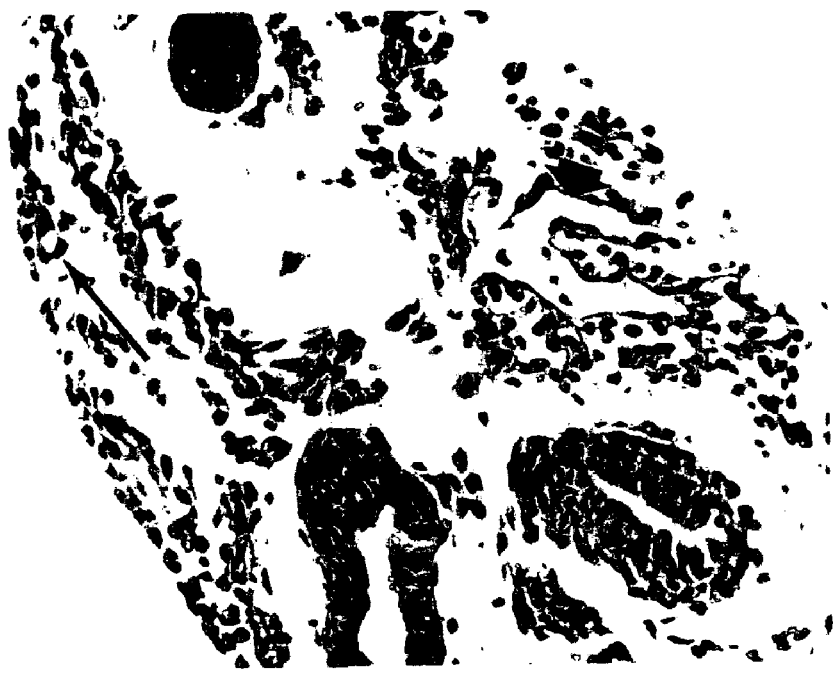
Figure 13G:
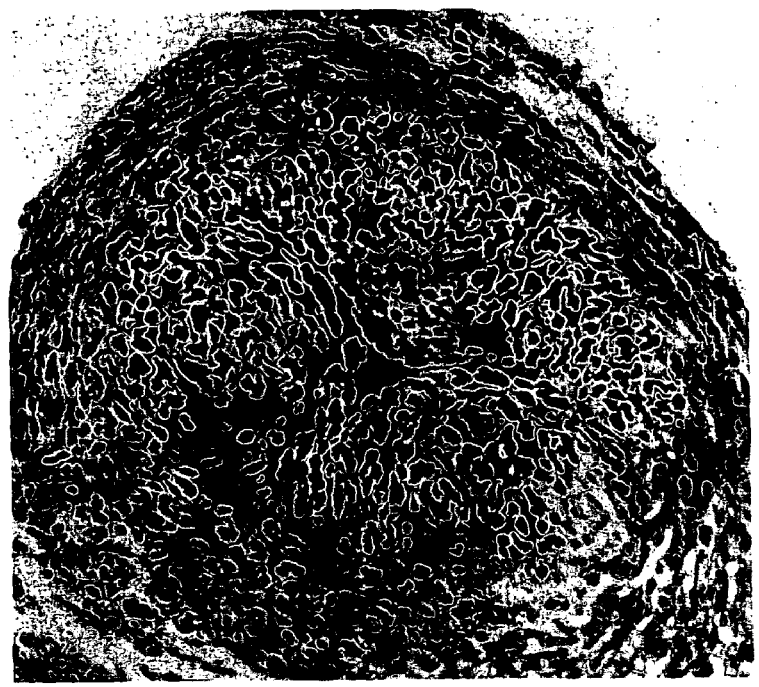
Figure 13H:
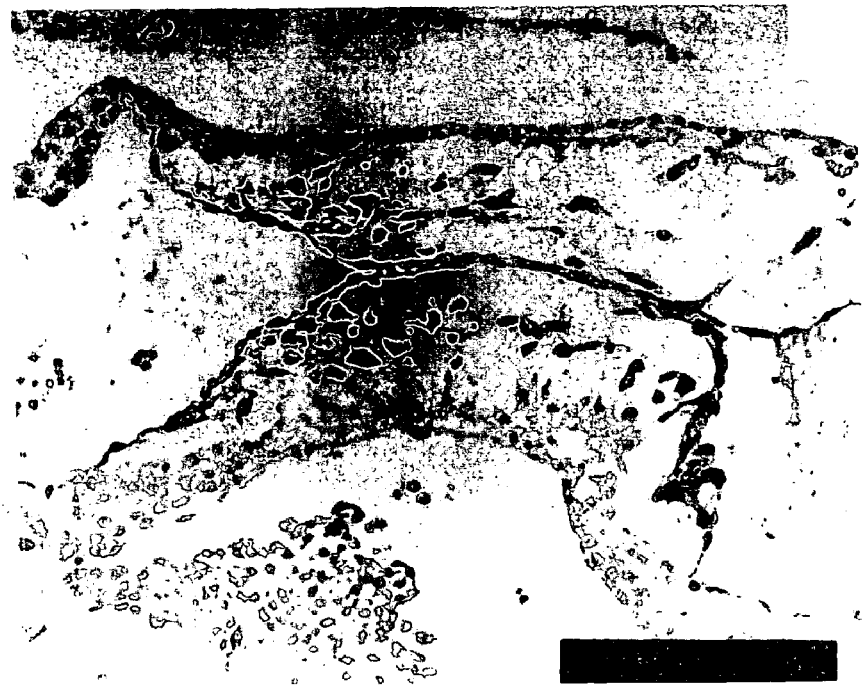

LacZ staining of embryos at day 13.5 of development was evaluated in the whole mount, and in sections made from paraffin embedded embryos. By this time, there was only patchy staining of endothelial cells in large vessels such as the aorta, whereas smaller vessels had virtually no staining (FIG. 13E). The only blood vessels which showed prominent lacZ staining at this stage were the pulmonary capillaries. The developing pulmonary vascular network stained intensely, making the entire lung appear grossly blue-green (FIG. 13E). Identification of the stained cells was made by microscopy of stained sections (FIG. 13F). Also, visualization of X-gal stained cells forming vascular channels was possible by viewing thick sections with Nomarski differential interference contrast optics. Organ vasculature associated the liver, brain and kidney showed no staining. In the heart, there was some residual staining of endothelial cells of the atrium. The majority of endothelial cells lining the ventricle no longer stained. The striking finding in the ventricle was that the cells forming the papillary muscle and the mitral valve showed marked staining. This labeling was seen not only in the endothelial cells on the surface, but in cells forming these structures. In a similar fashion, cells in the area of the forming valves of the aorta and pulmonary showed lacZ activity. Again, cells in the forming valve and in the wall of the vessel were stained (FIGS. 13G and 13H). The only non-cardiovascular staining was observed in cells in the areas of active bone formation. In particular, staining was most prominent in the proximal portions of the ribs, vertebrae, and the limb girdles (FIG. 13E). After 13.5 days, the only cells expressing the lacZ gene were pulmonary endothelial cells. After approximately 15.5 days of development, expression of the reporter transgene diminished and was completely negative by the time of birth.

The aforementioned observations indicate that the protein encoded by the transcription unit in the del-1 locus is involved in early developmental processes in the cardiovascular system. This gene is not only a lineage marker, since it is expressed in restricted groups of endothelial cells in a temporally regulated fashion. The restricted expression seen at later stages indicates a connection with the origin of these endothelial cells, the mechanism of blood vessel formation, or the context-derived phenotype of these cells. Cells of the primordial endocardium express this marker, indicating a role in cardiogenesis. Most striking is the pattern of expression in the developing valvular apparatus of the heart. Competent endothelial cells in the forming septum and valves have been shown to undergo an epithelial-mesenchymal transformation. This transformation appears to be due, at least-in part, to an inductive signal, such as transforming growth factor beta 3, which is released by the myocardium (Potts et al., 1991, *Proc. Natl. Acad. Sci. U.S.A.* 88:1516–1520; Sinning et al., 1992, *Anat. Rec.* 232:285–292). Reporter gene expression in the SLM275 mouse marked the competent cells of the endocardium which would respond to this signal, and expression appeared to persist for some time after the transformation (FIGS. 13G and 13H). This pattern of gene expression is unlike that described for any known molecule. Although the early endothelial expression pattern is similar to that characterized for the tyrosine kinases tek and flk-1 (Dumont et al., 1992, *Oncogene* 7:1471–1480; Millauer et al., 1993, *Cell* 72:835–846), there are striking differences at later stages which clearly indicate that lacZ expression in the transgenic animals marks a novel gene.

7.2.2. Expression Analysis by Northern Blot

Expression of del-1 in various fetal and adult tissues was examined by Northern blot analysis (Tables 1 and 2). A portion of the mouse cDNA clone (0.3 kb Sac I probe) was used as a probe on six poly A RNA filters purchased from Clontech Inc. Human fetal tissues which were undergoing vasculogenesis were positive (Table 2). An organ blot generated with RNA from a 15.5 day mouse embryo indicated expression in highly vascular organs such as kidney, lung, nervous system and head. Also, the time course of expression in whole mouse embryos was consistent with the β-gal staining results observed in transgenic mice (Table 3). In general, adult mouse tissues were negative, or only weakly positive (Table 4). Mouse cDNA clones isolated from a brain cDNA library appeared to be identical to the embryonic del-1. Two human cancer cell lines tested were weakly positive (Table 5). The results of Northern blot analysis were basically consistent with the pattern for a gene which was specifically active during endothelial cell development.

TABLE 1

| Human Adult | |
|---|---|
| heart | + |
| brain | ++++ |
| placenta | − |
| lung | − |
| liver | − |
| spleen | − |
| thymus | − |
| prostate | − |
| testis | − |
| ovary | + |
| skeletal muscle | − |
| kidney | − |
| pancreas | − |
| small intestine | + |
| colon | − |
| peripheral blood leukocyte | +/− |

TABLE 2

| Human Fetal | |
|---|---|
| brain | +++ |
| lung | +++ |
| liver | + |
| kidney | ++ |

(Pooled from 17-16 wks)

TABLE 3

| Mouse Embryo | |
|---|---|
| 7-day | − |
| 11-day | ++ |

TABLE 3-continued

| Mouse Embryo | |
|---|---|
| 15-day | +++ |
| 17-day | ++ |

TABLE 4

| Mouse Adult | |
|---|---|
| heart | − |
| brain | − |
| spleen | + |
| lung | − |
| liver | − |
| skeletal muscle | − |
| kidney | − |

TABLE 5

| Human Cancer Cell | |
|---|---|
| Promyelocytic leukemia HL60 | +/− |
| HeLa cell S3 | + |
| chronic myelogenous leukemia K-562 | − |
| lymphoblastic leukemia MOLT4 | − |
| Burkit's lymphoma Raji | − |
| colorectal adenocarcinoma SW480 | − |
| lung carcinoma A549 | − |
| melanoma G361 | − |

7.2.3 Expression Analysis by RT-PCR

RNA from mouse yolk sac (day 8 through day 12) and mouse fetal liver (day 13 through day 19) were tested for del-1 expression by RT-PCR. All tested samples were positive, consistent with the Northern blot analysis and results from β-gal staining in transgenic mice (Table 6). Several mouse yolk sac-derived cell lines were also tested by RT-PCR for expression of del-1. For comparison, several other cell lines and total d15 mouse fetal liver RNA samples were tested. All samples shown in Table 7 except ECV304 (a human endothelial cell line) were of mouse origin. The yolk sac-derived cell lines grown in long-term culture were not expressing del-1 at a detectable level. These cell cultures were not forming endothelial cell-like structures under these conditions. In contrast, an endothelial tumor line, EOMA, expressed high levels of del-1.

TABLE 6

| Yolk Sac and Fetal Liver | |
|---|---|
| Sample | Result |
| d8 Yolk Sac | + |
| d9 Yolk Sac | + |
| d10 Yolk Sac | + |
| d11 Yolk Sac | + |
| d12 Yolk Sac | + |
| d13 Fetal Liver | + |
| d14 Fetal Liver | + |
| d15 Fetal Liver | + |
| d16 Fetal Liver | + |
| d17 Fetal Liver | + |
| d18 Fetal Liver | −+ |

TABLE 7

Cell Lines

| cell line | del-1 |
|---|---|
| 3T3 A31 | − |
| Sto 1 | ++ |
| YS4 | − |
| Pro 135 | − |
| Pro 175 | − |
| D-1 | − |
| A10 | − |
| ROSA02 | − |
| d15FL | ++ |
| EOMA | +++ |
| ECV304 (human) | − |

A number of human tumors implanted in nude mice and cultured in vitro were shown to express del-1 by RT-PCR. For example, Table 8 shows the expression of del-1 in human osteosarcoma cell line 143B in vivo and in vitro. EOMA was used as a positive control. CD34, flk-1 and tie-2 are known markers for endothelial cells. When human and mouse del-1 specific PCR primers were used, both human (tumor) and murine (host) del-1 expression was detected. In addition, a variety of human tumor cell lines expressed del-1 in culture (Table 9). These results indicate that Del-1 may be used as a tumor marker in certain cancers diagnostically and therapeutically. In addition, host expression of del-1 is also up-regulated, possibly due to angiogenesis in tumor sites.

TABLE 8

Human osteosarcoma 143B

| Sample | Actin | del-1 | CD34 | flk-1 | tie-2 |
|---|---|---|---|---|---|
| control nude mouse skin | − | − | nd | nd | nd |
| 7 day tumor | + | + | nd | nd | nd |
| 10 day tumor | + | + | + | + | + |
| 14 day tumor | + | + | + | + | + |
| cultured 143B cells | + | + | − | − | − |
| EOMA | + | + | + | + | + | nd = not determined

TABLE 9

Human tumor cell lines

| Cell Type | Sample | 27 cycles | 33 cycles |
|---|---|---|---|
| Normal | Myoblast | + | +++ |
|  | HYSE-E | + | +++ |
|  | HYS-VS1 | ++ | ++++ |
| Leukemia | K562 | − | − |
|  | HEL | − | +/− |
|  | Mo7e | − | − |
| Glioblastoma | U-118 MG | + | +++ |
|  | U-87 MG | ++ | +++ |
| CNS Tumor | SF295 | + | +++ |
|  | U251 | ++ | ++++ |
|  | SNB75 | ++ | ++++ |
|  | SNB19 | + | +++ |
|  | SF539 | + | +++ |
| Osteosarcoma | 143B | + | ++++ |
| Breast Carcinoma | DU4475 | − | − |
|  | MCF-7 | +/− | +++ |
|  | MDA231 | + | +++ |
| Endothelial | ECV304 | − | − |
|  | HUVEC | + | +++ |

8. EXAMPLE

Immunereactivity of DEL-1 Gene Product

8.1. Materials and Methods

8.1.1. Antibody Production

A partial del-1 cDNA encoding amino acids 353 to 489 of the murine gene was cloned into pMALC2 (New England Biolabs) to generate a maltose binding protein-partial Del-1 fusion protein. The del-1 sequence included in this construct encodes a portion of the carboxyl terminal discoidin-like domain. Recombinant fusion protein was expressed and purified over an amylose affinity matrix according to the manufacturer's recommendations. Protein was emulsified into Freund's complete adjuvant, and injected as multiple subcutaneous injections into two New Zealand White rabbits. Boosting and harvesting of immune serum was performed according to established methodology (Harlow and Lane, 1988, *Antibody: A Laboratory Manual*, Cold Spring Harbor Laboratory). Immune serum obtained after the second boost was subjected to affinity purification. First, the anti-serum was precleared over a Sepharose column coupled to total bacterial lysate. Subsequently, the antiserum was purified over an affinity column made from recombinant fusion protein coupled to Sepharose. The specificity of the antiserum, was evaluated first with western blots containing proteins from bacteria expressing the recombinant fusion protein before and after cleavage with factor Xa, or the maltose binding protein alone. Whole bacterial lysates from cells induced with IPTG were run on polyacrylamide gels, transferred to nitrocellulose, and probed with the affinity-purified antiserum. While crude antiserum labeled bands corresponding to maltose binding protein and the Del-1 portion of the fusion protein, affinity-purified antiserum specifically labeled the Del-1 component of the fusion protein.

8.1.2 Western Blot

For western blots of eukaryotic proteins, cells were harvested by lysis in a standard lysis buffer or Laemmli loading buffer. Cell culture supernatant was collected and concentrated by centrifugation in a CENTRICON filter, and extracellular matrix harvested by first removing cells with 1 mM EDTA in PBS, and then scraping the cell culture dish with a small volume of Laemmli buffer at 90° C.

8.1.3 Immunohistochemistry

Immunohistochemistry was performed on sections prepared from Bouin's fixed, paraffin-embedded, staged mouse embryos according to well established methodology (Hogan et al., 1994, *Manipulating the Mouse Embryo*, Cold Spring Harbor Press; Quertermous et al., 1994 *Proc. Natl. Acad. Sci. U.S.A.* 91:7066). The affinity-purified Del-1 antiserum was employed at a dilution of 1:500 to 1:1000, and the specificity of staining verified by competition with recombinant protein. Staining of cartilage was amplified by pretreating the section with dilute trypsin solution.

8.1.4 Transfection of Yolk Sac Cells

A eukaryotic expression vector was constructed by cloning the entire open reading frame of the major del-1 transcript into ohbAPr-3-neo (Gunning et al., 1987, *Proc. Natl. Acad. Sci. U.S.A.* 84:4831). This construct was transfected into yolk sac cells with Lipofectamine (Gibco BRL), and clones selected in the presence of 1000 µg/ml of G418. Clones were evaluated for del-1 expression by northern and western blotting, and a group of clones with varying amounts of Del-1 protein were selected for further study. To serve as negative controls, a group of clones were randomly selected from a transfection with the empty phbAPr-3-neo vector.

8.2. Results

The major murine del-1 coding sequence was inserted into a eukaryotic expression vector and transfected into Del-1-non-expressing yolk sac cells (Wei et al., 1995, *Stem Cell* 13:541). Pooled transfectants with an empty expression vector or the del-1 construct were selected in G418. Lysates, cell culture supernatants and extracellular matrix were prepared from transfected cells, and reacted with an affinity-purified rabbit antiserum in Western blots. The polyclonal antiserum was generated to recombinant Del-1 fusion protein expressed in bacteria. FIG. 14A shows that a band of 52,000 daltons molecular weight was recognized in cell lysates prepared by harvesting the cells in lysis or standard Laemmli gel loading buffer, and in extracellular matrix. This band corresponds with the predicted molecular weight for Del-1 based on the deduced amino acid sequence, and represented the full-length Del-1 protein. In contrast, no protein was identified with culture supernatants harvested from the transfectants, even when concentrated 100-fold. Additionally, smaller proteolytic fragments were also detected. These results indicate that Del-1 is secreted across the surface of endothelial cells, and deposited in the extracellular matrix.

Several stably transfected yolk sac cell clones with the del-1 gene were selected (FIG. 14B). When the transfected cells were reacted with the aforementioned antibody, both the membrane of certain yolk sac cells and the extracellular matrix were stained as compared with mock-transfected yolk sac cells as negative control (FIGS. 15A, 15B). In keeping with this staining pattern, immunostaining of developing bone of a 13.5 day mouse embryo detected the Del-1 protein in the lacunae within the bone, which were composed of extracellular matrix proteins (FIG. 16).

Figure 17A:
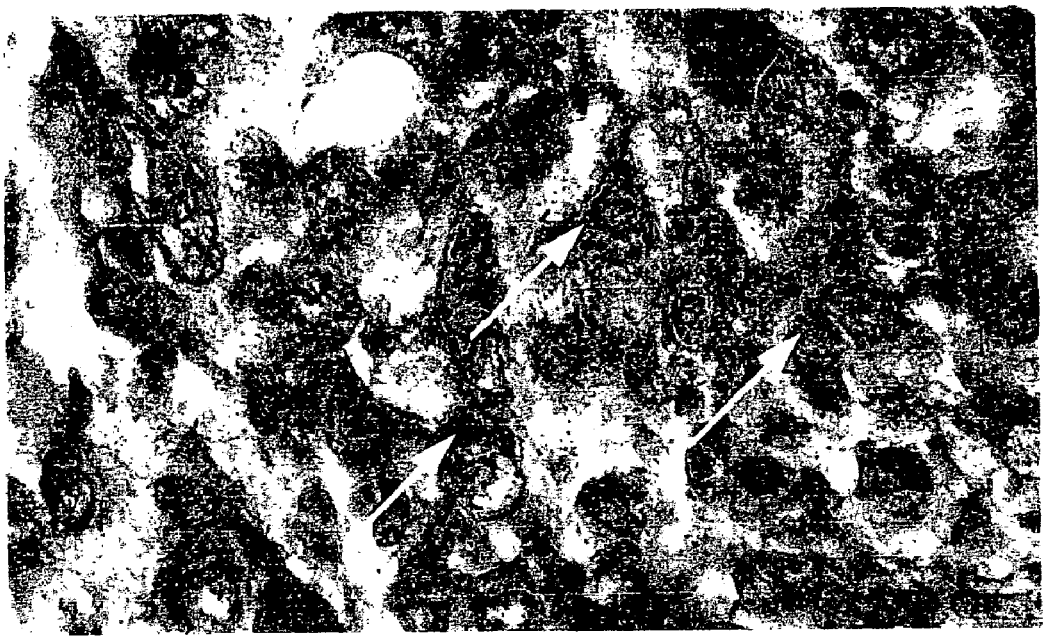
Figure 17B:
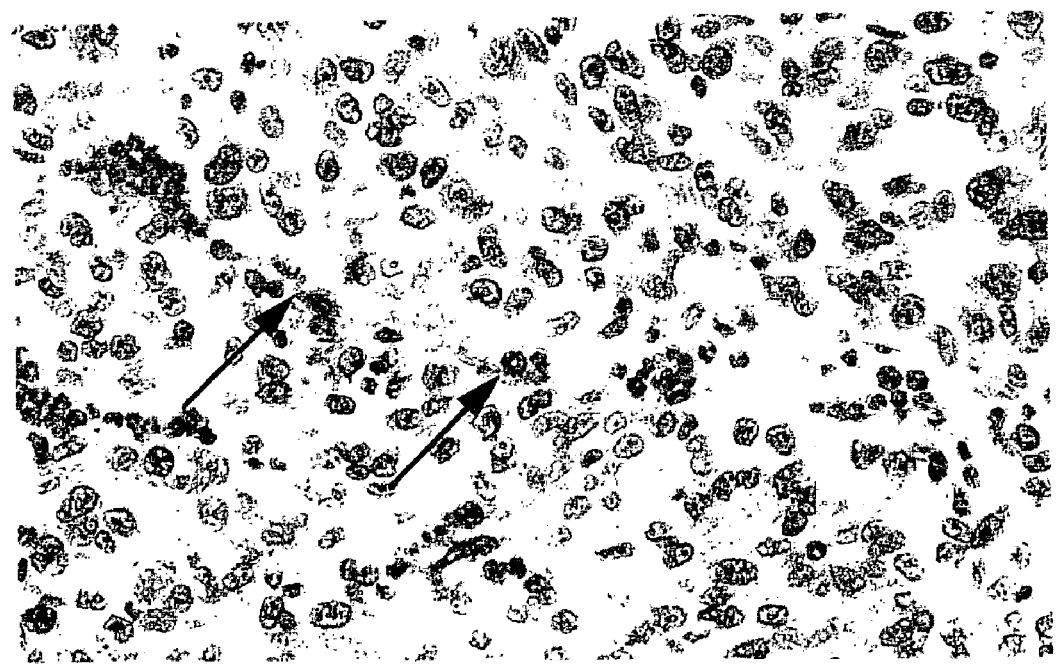

In order to test the expression of del-1 in tumor cells by immunohistochemistry, human glioma cells were implanted in nude mice. The tumor was isolated, sectioned and stained with the aforementioned antibody followed by an anti-rabbit antibody conjugated with horse radish peroxidase and developed with Sigma Fast Red substitute. FIG. 17A shows that the in vivo tumor cells were stained with the antibody in a polarized fashion. Polarization of del-1 expression in tumor cells might have resulted from the interaction of the gene product with cellular receptors on adjacent cells. In addition, a blood vessel of mouse origin traversing the human tumor was also stained with the antibody (FIG. 17B).

9. EXAMPLE

DEL-1 Inhibits Vascular Formulation 9.1 Materials and Methods 9.1.1. Angiogenesis Assays In vitro angiogenesis assays on "MATRIGEL" (Biocoat, Becton Dickinson) were conducted in 24 well plates coated with 50 µl of "MATRIGEL". del-1 transfectants and control transfectants were plated at a density of $5 \times 10^4$ cells/well (low density) or $2 \times 10^5$ cells/well (high density), and observed for seven days.

For the assay evaluating morphogenetic potential of wild type yolk sac cells on del-1 conditioned matrix, the matrix was generated by growing $10^6$ del-1 transfectants in 6 cm dishes for 7 days. A control matrix was generated by growing control transfectants under identical conditions. Transfected cells were removed with 0.5 M EDTA and extensive washing, and $10^6$ wild type yolk sac cells were plated on the matrix produced by the del-1 or the control transfectants. Cells were cultured and observed for seven days.

For the in vitro angiogenesis sprouting assay, del-1 and control transfectants were trypsinized, and $10^6$ cells cultured in a 15 ml conical tubes for 48 hours. Cell cultures were then transferred into a bacterial petri dish, and cultured for 4–7 days. Under these conditions, cell aggregates were formed. Several aggregates were collected for del-1 and control transfectants, and these were transferred to 24 well plates coated with "MATRIGEL". Sprouting angiogenesis was evaluated at 24 and 43 hours.

9.2 Results

Figure 18A:
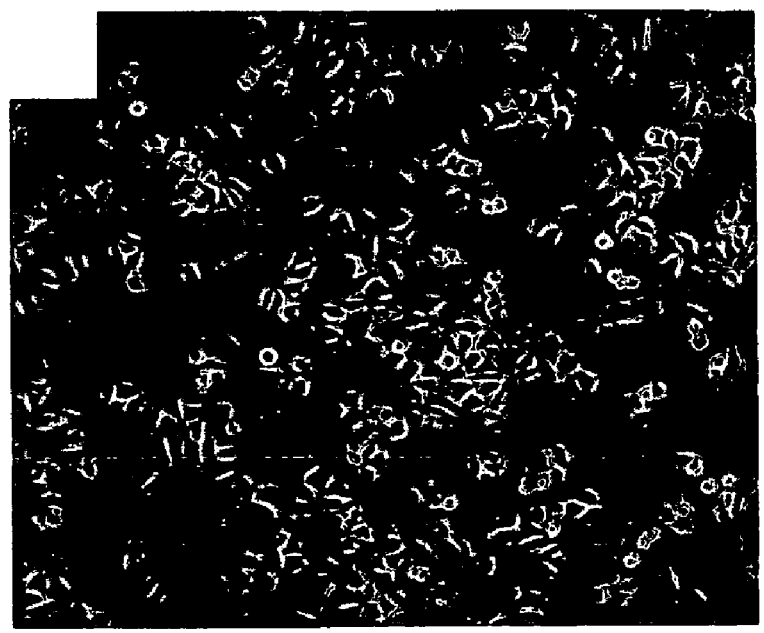
Figure 18B:

The yolk sac cell line, YS-B, was chosen as the parental cell for del-1 tansfection because it had characteristics of embryonic endothelial cells, did not express del-1, was clonal and long lived in culture (FIG. 18A). Most importantly, these cells provided a model of vascularization of the early yolk sac. While they were easily grown and maintained with frequent passage, when allowed to accumulate to high density they spontaneously formed vascular structures. This process was accelerated when the cells were plated on the basement membrane-like material "MATRIGEL", on which they behaved similar to various types of cultured endothelial cells (FIG. 18B). Cell lines transfected with the cDNA encoding of the major form of del-1 were selected for varying levels of expression of the transfected construct (FIG. 14B). Cell lines transfected with the empty expression plasmid were selected to serve as negative controls.

Figure 18C:
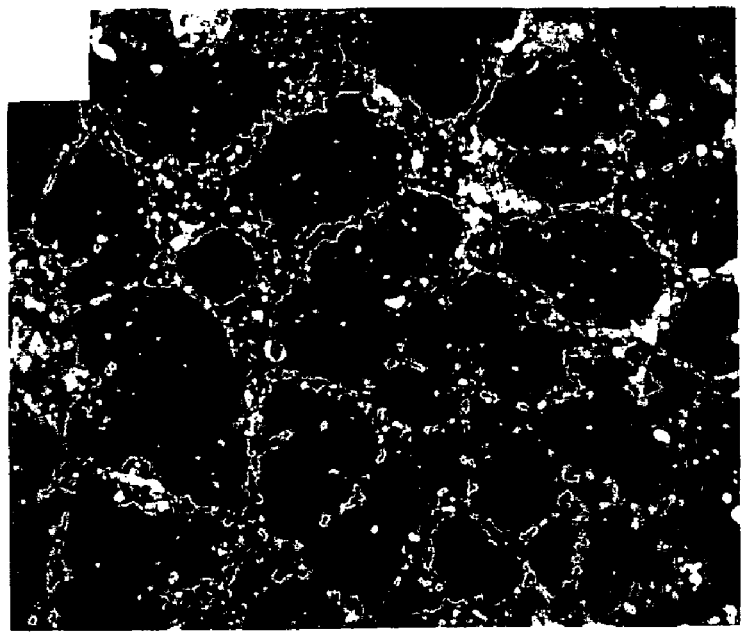
Figure 18D:
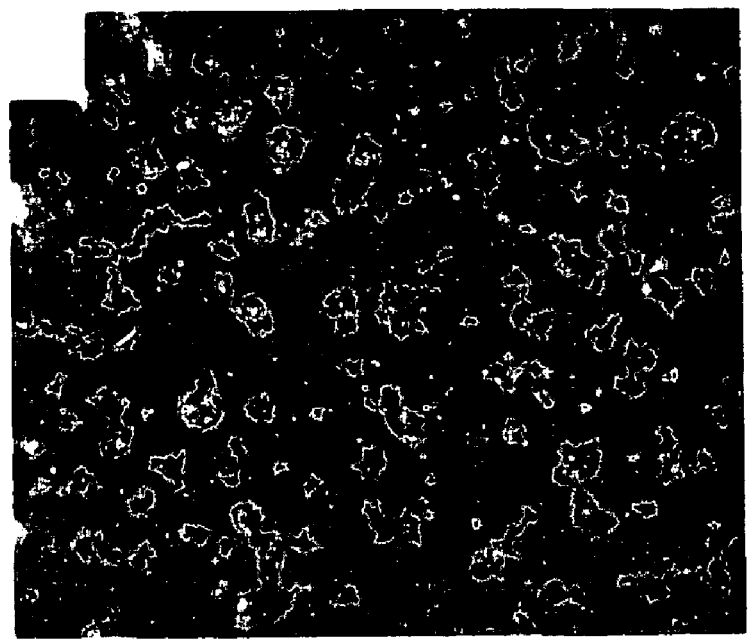

The del-1 transfected yolk sac clones and mock-transfected yolk sac lines were compared for their ability to form branching vascular-like structures on "MATRIGEL". After 24 hours on "MATRIGEL", the negative control transfectants had established an intricate network typical for these cells (FIG. 18C). Cells (L10) expressing high levels of del-1 showed a markedly different pattern, assembling into multiple well-spaced clusters (FIG. 18D). This abrogation of morphogenesis was directly related to the level of del-1 expression, as low del-1 expressing clones, L13 and L14, showed some degree of branching morphology.

Figure 18E:
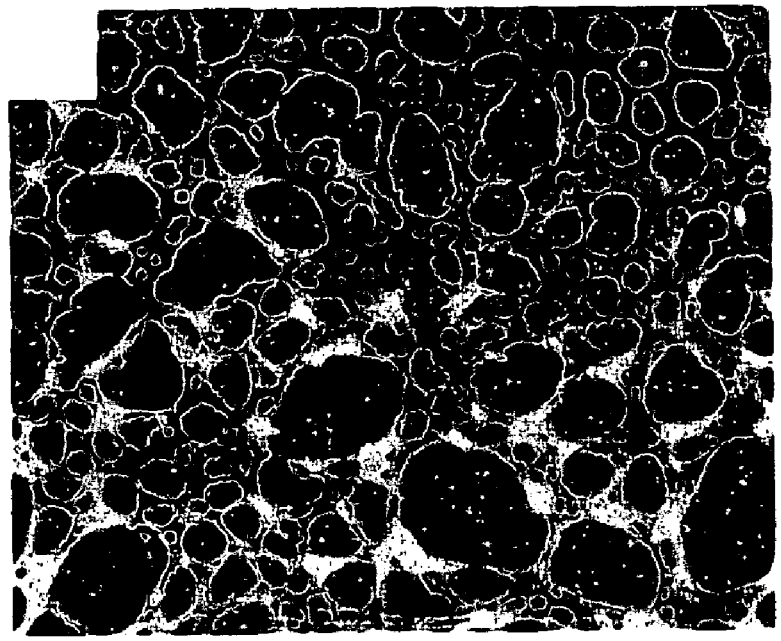
Figure 18F:
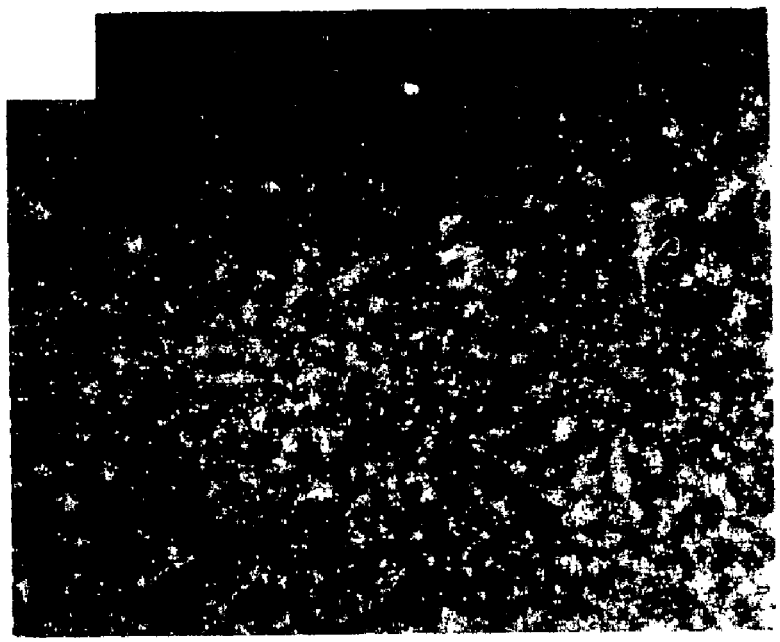

Since Del-1 protein is deposited in the extracellular matrix, one del-1 expressing clone, L10, was used to generate a cell culture matrix containing Del-1 protein. Matrix generated by negative control clones should differ only by the absence of Del-1. Transfected and control lines were cultured for 7 days, and then gently removed from the culture dish by extensive washing with 1 mM EDTA. By visual inspection, only a rare cell was not removed with this technique. Non-transfected native yolk sac cells were then plated on the Del-1-containing and the control matrices, and scored for their ability co assemble into a network. The yolk sac cells required several days at high density to undergo morphogenesis, and the network was lace-like in appearance. Cells grown on the matrix produced by negative control transfectants were able to produce the network (FIG. 18E). In contrast, yolk sac cells grown on matrix containing Del-1 revealed no evidence of morphogenesis. They formed instead a dense monolayer (FIG. 18F).

Figure 18G:
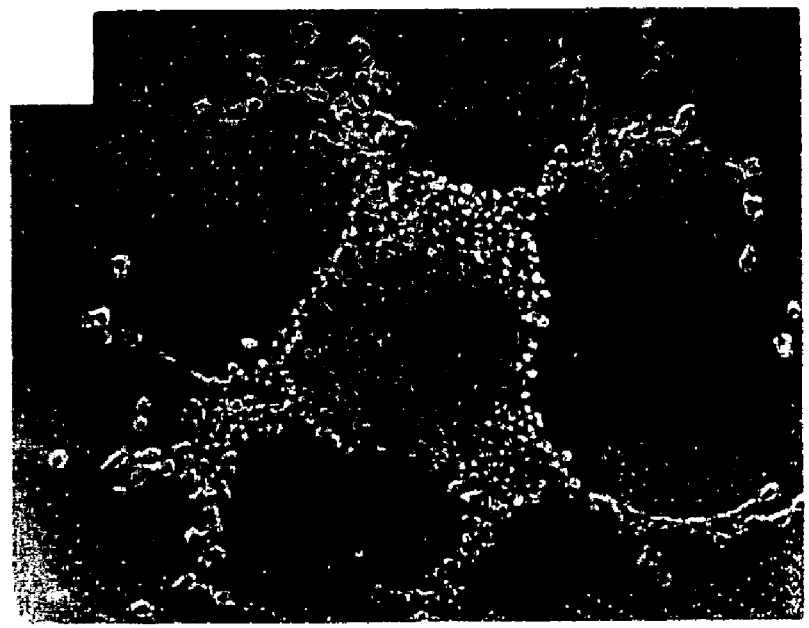
Figure 18H:
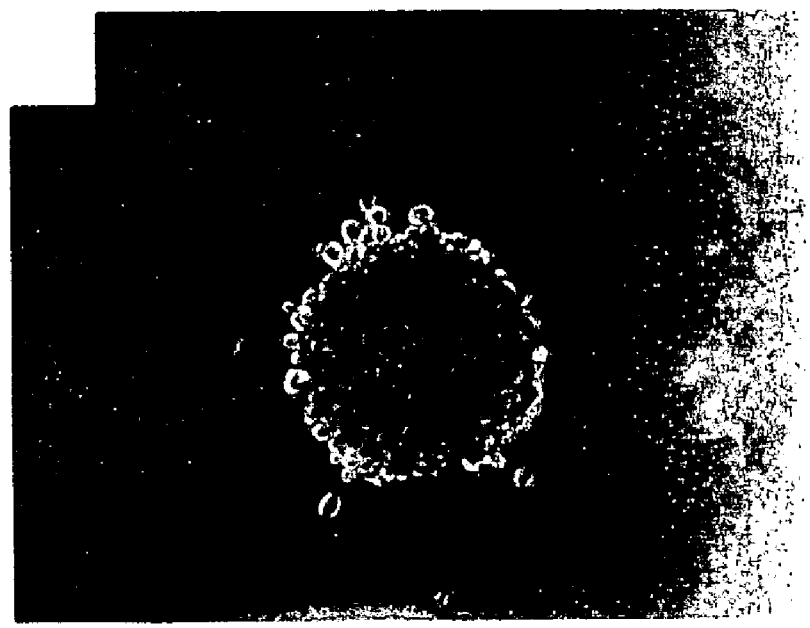

Next, an in vitro angiogenesis sprouting assay was employed with the transfected yolk sac lines. This assay has been employed to evaluate angiogenic potential (Pepper et al. 1991, *J. Cell. Physiol.* 146:170). Transfected cells were allowed to stand overnight in a conical tube to allow them to aggregate, and the cell mass was then placed on "MATRIGEL". The ability of the del-1 expressing cells to migrate onto the "MATRIGEL" and assemble into branching structures was compared to control cells. Within 24 hours, the control cells formed a series of branching projections, while the cells expressing del-1 remained virtually confined to the cellular aggregate (FIGS. 18G and 18H). While there was some evidence of spreading of the del-1 expressing cells after 48 hours, it was more as a sheet rather than a sprouting structure.

Hence, Del-1 inhibits vascular morphogenesis and may be used to regulate endothelial cell differentiation.

10. EXAMPLE

DEL-1 Binds to Integrin Alpha V Beta 3

10.1 Materials and Methods 10.1.1. Recombinant DEL-1 Purification and Refolding

Recombinant murine Del-1 protein (major form) was prepared using an *E. coli* expression system and protein refolding technique. *E. coli* cells with the del-1 containing pET28a vector (Novagen Inc.) were grown and induced following the protocol recommended by the manufacturer. Approximately 50 to 100 mg of crude recombinant Del-1 were routinely produced from 1 L of bacterial culture in the form of insoluble cytoplasmic inclusion bodies. Inclusion bodies were isolated by sonication of the *E. coli* cells, centrifugation and collection of the pellet fraction. Inclusion bodies from 500 ml of culture were then washed three times with 50 ml of 2M Urea, 0.025 M Tris-Cl (pH 8.0), 0.025% Triton X100. This procedure yielded a crude, insoluble, Del-1 product of >80% purity.

Recombinant Del-1 was dissolved by suspending the pellet from 500 ml of culture in 2.5 ml of 8M Urea, 100 mM DTT, 0.1 M Tris-Cl (pH 8.0), 0.05% Triton X100, followed by incubation at room temperature for 1 hr. Insoluble material remaining was removed by centrifugation and the soluble supernatant fraction was diluted 10 fold to 25 ml with 8M Urea, 100 mM Tris-Cl (pH 8.0), 0.05% Triton X100. Protein concentration was then measured by Bradford protein determination assay.

Soluble, reduced Del-1 was refolded by diluting to a final concentration of 0.01 mg/ml into refolding buffer: 100 mM Tris-Cl (pH 8.0), 100 mM $(NH_4)_2SO_4$, 2 mM reduced glutathione, 0.5 mM oxidized glutathione, 0.05% sodium azide, 0.025 mg/ml PMSF. Refolding was performed by incubating this reaction mix at 4° C. for one week. Refolded Del-1 was then concentrated using an Amicon spiral concentrator and the soluble material remaining was collected.

The recombinant Del-1 product produced from the pET28a expression vector is a fusion protein with both N-terminal and C-terminal polyhistidine tags. This product was purified using the Novagen His tag resin purification system, following the protocol recommended by the supplier.

Refolded murine recombinant Del-1 was soluble and stable when stored at 4° C. in Tris-Cl buffer with 100 mM $(NH_4)_2SO_4$ at concentrations of less than or equal to 100 mg/ml.

10.1.2. Cell Adhesion Assays

Human umbilical vein endothelial cells (HUVEC) (Clonetics Inc., San Diego, Calif.) were grown as indicated by the supplier in endothelial growth media supplemented with 10 ng/ml human recombinant epidermal growth factor, 1 μg/ml hydrocortisone, 50 μg/ml gentamicin, 12 μg/ml bovine brain extract and 2% FBS. Cells were grown at: 37° C./5% $CO_2$ to 70% confluency before use in the binding assay. Non-tissue culture treated 96 well plates were coated with appropriate levels of target protein (1–20 μg of either murine recombinant Del-1, vitronectin, or BSA) diluted in calcium and magnesium free PBS for 24 hrs at 4° C. The plates were washed with PBS and blocked for 30 min with a solution of heat treated (95° C. for 5 min) PBS containing 3% BSA. HUVEC cells were harvested by trypsinization and resuspended in an adhesion buffer (Hanks balanced salt solution pH 7.4 containing 10 mM Hepes, 2.2 mM $MgCl_2$, 0.2 mM $MnCl_2$ and 1% BSA). Cells ($10^4$/100 μl) were added to each well in the presence or absence of the indicated antagonists or controls at varying concentrations. Antagonists included anti-human αVβ3 (clone LM609, Chemicon Inc.), RGE peptides (the inactive control GRGESP) or RGD the stable antagonist GPenGRGDSPCA or GRGDdSP all from Gibco). Cells were incubated at 37° C./5% $CO_2$ for 60–90 min and wells were washed until no cells remained in the BSA control. To count remaining cells, 100 μl of endothelial media was added to each well. Cells number was determined by the Promega Cell titer AQ as indicated by the manufacturer.

10.2 Results

Recombinant Del-1 protein and del-1 transfectants bound HUVEC. In order to identify a cellular receptor on HUVEC for Del-1, various peptides and antibodies were used to inhibit the interactions between Del-1 and HUVEC in cell adhesion assays. FIG. 19 shows that an anti-αVβ3 antibody specifically inhibited recombinant Del-1 binding to HUVEC. In contrast, anti-αVβ5 did not inhibit, nor did the control Ig. Furthermore, an RGD peptide was also shown to inhibit Del-1 binding to HUVEC (FIG. 20). Similar results were obtained using extracellular matrix obtained from del-1 transfected cells. Therefore, Del-1 binds to αVβ3 expressed by HUVEC, possibly via RGD in its second EGF-like domain.

αVβ3 is an integrin expressed by certain cell types and is associated with bFGF-induced angiogenic endothelial cells. Agents that bind to this integrin induce apoptosis of angiogenic endothelial cells. Since Del-1 binds to this integrin, it may be used to induce apoptosis during angiogenesis in tumor sites to reduce tumor growth.

11. EXAMPLE

Chromosomal Localization of Human DEL-1

DNA from P1 clone 10043 was labeled with digoxigenin dUTP by nick translation. The labeled probe was combined with sheared human DNA and hybridized to normal metaphase chromosomes derived from PHA stimulated peripheral blood lymphocytes in a solution containing 50% formamide, 10% dextran sulfate and 2×SSC. Specific hybridization signals were detected by incubating the hybridized slides in fluoresceinated antidigoxigenin antibodies followed by counterstaining with DAPI. The initial experiment resulted in specific labeling of the long arm of a group B chromosome.

A second experiment was conducted in which a probe that had previously been mapped to 5q34, and confirmed by cohybridization with a probe from the cri du chat locus which is known to localize to 5p15, was cohybridized with clone 10043. This experiment resulted in the specific labeling of the mid and distal long arm of chromosome 5 (FIGS. 21A and B). Measurements of 10 specifically hybridized chromosomes 5 demonstrated that clone 10043 was located at a position which was 29% of the distance from the centromere to the telomere of chromosome arm 5q, an area that corresponded to band 5q14. A total of 80 metaphase cells were analyzed with 74 exhibiting specific labeling.

This region of the chromosome has been found to be a break point in some human cancers (Wieland and Bohm, 1994, *Cancer Res.* 54:1772; Fong et al., 1995, *Cancer Res.* 55:220; Wieland et al., 1996, 12:97, *Oncogene* 12:97). Thus, chromosome 5 aberrations may lead to altered expression of del-1 and contribute to the malignant phenotype.

12. Deposit of Microorganisms

The following organisms were deposited with the American Type Culture Collection (ATCC), 12301 Parklawn Drive, Rockville, Md. 20852.

Strain Designation Accession No.
Hu DEL-1.Z1 ATCC 97155
Hu DEL-1.Z20 ATCC 97154
mus DEL-1.1 ATCC 97196
mus DEL-1.18 ATCC 97197

The present invention is not to be limited in scope by the exemplified embodiments or deposited organisms which are intended as illustrations of single aspect of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

---

What is claimed is:

1. An isolated, purified antibody which binds to a polypeptide of a mammalian Del-1, wherein said mammalian Del-1 comprises an amino acid sequence as shown in a SEQ ID NO selected from the group consisting of: SEQ ID NO:10; SEQ ID NO:29; SEQ ID NO:30 and SEQ ID NO:31.

2. The antibody of claim 1 wherein the antibody specifically binds to an epitope of said mammalian Del-1.

3. The antibody of claim 1 wherein the antibody is selected from a group consisting of single chain, chimeric, Fab, F(ab')$_2$, and a fragment produced by an Fab expression library.

4. The antibody of claim 1 wherein the antibody is a polyclonal antibody.

5. The antibody of claim 1 wherein the antibody is a monoclonal antibody.

6. The antibody of claim 1 wherein said mammalian Del-1 is a human Del-1 comprising an amino acid sequence as shown in a SEQ IDs selected from the group consisting of: SEQ ID NO:30 and SEQ ID NO:31.

7. The antibody of claim 6 wherein said human Del-1 comprises the amino acid sequence as shown in SEQ ID NO:30.

8. The antibody of claim 6 wherein said human Del-1 comprises the amino acid sequence as shown in SEQ ID NO:31.

9. The antibody of claim 6 wherein the antibody specifically binds to an epitope of said human Del-1.

10. The antibody of claim 6 wherein the antibody is selected from a group consisting of single chain, chimeric, Fab, F(ab')$_2$, and a fragment produced by an Fab expression library.

11. The antibody of claim 6 which is a polyclonal antibody.

12. The antibody of claim 6 which is a monoclonal antibody.

* * * * *

SEQUENCE LISTING

<160> NUMBER OF SEQ ID NOS: 33

<210> SEQ ID NO 1
<211> LENGTH: 81
<212> TYPE: PRT
<213> ORGANISM: Mus sp.

<400> SEQUENCE: 1

```
Asp Leu Leu Val Pro Thr Lys Val Thr Gly Ile Ile Thr Gln Gly Ala
1               5                   10                  15

Lys Asp Phe Gly Asp Val Leu Phe Val Gly Ser Tyr Lys Leu Ala Tyr
            20                  25                  30

Ser Asn Asp Gly Glu His Trp Met Val His Gln Asp Glu Lys Gln Arg
        35                  40                  45

Lys Asp Lys Val Phe Gln Gly Asn Phe Asp Asn Asp Thr His Arg Lys
    50                  55                  60

Asn Val Ile Asp Pro Pro Ile Tyr Ala Arg Phe Ile Arg Ile Leu Pro
65                  70                  75                  80

Leu
```

<210> SEQ ID NO 2
<211> LENGTH: 81
<212> TYPE: PRT
<213> ORGANISM: Homo sapiens

<400> SEQUENCE: 2

```
Asp Leu Gly Ser Ser Lys Glu Val Thr Gly Ile Ile Thr Gln Gly Ala
1               5                   10                  15

Arg Asn Phe Gly Ser Val Gln Phe Val Ala Ser Tyr Lys Val Ala Tyr
            20                  25                  30

Ser Asn Asp Ser Ala Asn Trp Thr Glu Tyr Gln Asp Pro Arg Thr Gly
        35                  40                  45

Ser Ser Lys Val Phe Gln Gly Asn Leu Asp Asn Ser His Lys Lys
    50                  55                  60

Asn Ile Phe Glu Lys Pro Phe Met Ala Arg Tyr Val Arg Val Leu Pro
65                  70                  75                  80

Val
```

<210> SEQ ID NO 3
<211> LENGTH: 81
<212> TYPE: PRT
<213> ORGANISM: homo sapiens

```
<400> SEQUENCE: 3

Asp Leu Leu Lys Ile Lys Lys Ile Thr Ala Ile Ile Thr Gln Gly Cys
1               5                   10                  15

Lys Ser Leu Ser Ser Glu Met Tyr Val Lys Ser Tyr Thr Ile His Tyr
                20                  25                  30

Ser Glu Gln Gly Val Glu Trp Lys Pro Tyr Arg Leu Lys Ser Ser Met
            35                  40                  45

Val Asp Lys Ile Phe Glu Gly Asn Thr Asn Lys Gly His Val Lys
        50                  55                  60

Asn Phe Phe Asn Pro Pro Ile Ile Ser Arg Phe Ile Arg Val Ile Pro
65                  70                  75                  80

Lys

<210> SEQ ID NO 4
<211> LENGTH: 72
<212> TYPE: PRT
<213> ORGANISM: mus sp.

<400> SEQUENCE: 4

Asp Leu Gln Lys Thr Met Lys Val Thr Gly Ile Ile Thr Gln Gly Val
1               5                   10                  15

Lys Ser Leu Phe Thr Ser Met Phe Val Lys Glu Phe Leu Ile Ser Ser
                20                  25                  30

Ser Gln Asp Gly His His Trp Thr Gln Ile Leu Tyr Asn Gly Lys Val
            35                  40                  45

Lys Val Phe Gln Gly Asn Gln Asp Ser Ser Thr Pro Met Met Asn Ser
        50                  55                  60

Leu Asp Pro Pro Leu Leu Thr Arg
65                  70

<210> SEQ ID NO 5
<211> LENGTH: 83
<212> TYPE: PRT
<213> ORGANISM: Xenopus sp.

<400> SEQUENCE: 5

Asp Leu Glu Asn Leu Arg Phe Val Ser Gly Ile Gly Thr Gln Gly Ala
1               5                   10                  15

Ile Ser Lys Glu Thr Lys Lys Tyr Phe Val Lys Ser Tyr Lys Val
                20                  25                  30

Asp Ile Ser Ser Asn Gly Glu Asp Trp Ile Thr Leu Lys Asp Gly Asn
            35                  40                  45

Lys His Leu Val Phe Thr Gly Asn Thr Asp Ala Thr Asp Val Val Tyr
        50                  55                  60

Arg Pro Phe Ser Lys Pro Val Ile Thr Arg Phe Val Arg Leu Arg Pro
65                  70                  75                  80

Val Thr Trp

<210> SEQ ID NO 6
<211> LENGTH: 79
<212> TYPE: PRT
<213> ORGANISM: xenopus sp.

<400> SEQUENCE: 6

Asp Leu Ala Glu Glu Lys Ile Val Arg Gly Val Ile Ile Gln Gly Gly
1               5                   10                  15
```

```
Lys His Lys Glu Asn Lys Val Phe Met Arg Lys Phe Lys Ile Gly Tyr
            20                  25                  30

Ser Asn Asn Gly Thr Glu Trp Glu Met Ile Met Asp Ser Ser Lys Asn
            35                  40                  45

Lys Pro Lys Thr Phe Glu Gly Asn Thr Asn Tyr Asp Thr Pro Glu Leu
 50                  55                  60

Arg Thr Phe Ala His Ile Thr Thr Gly Phe Ile Arg Ile Ile Pro
 65                  70                  75

<210> SEQ ID NO 7
<211> LENGTH: 75
<212> TYPE: PRT
<213> ORGANISM: homo sapiens

<400> SEQUENCE: 7

Gly Cys Glu Val Pro Arg Thr Phe Met Cys Val Ala Leu Gln Gly Arg
 1                5                  10                  15

Gly Asp Ala Asp Gln Trp Val Thr Ser Tyr Lys Ile Arg Tyr Ser Leu
            20                  25                  30

Asp Asn Val Ser Trp Phe Glu Tyr Arg Asn Gly Ala Ala Ile Thr Gly
            35                  40                  45

Val Thr Asp Arg Asn Thr Val Val Asn His Phe Phe Asp Thr Pro Ile
 50                  55                  60

Arg Ala Arg Ser Ile Ala Ile His Pro Leu Thr
 65                  70                  75

<210> SEQ ID NO 8
<211> LENGTH: 85
<212> TYPE: PRT
<213> ORGANISM: artificial sequence
<220> FEATURE:
<223> OTHER INFORMATION: consensus sequence of SEQ ID NOS:1-7
<220> FEATURE:
<221> NAME/KEY: MISC_FEATURE
<222> LOCATION: (3)..(7)
<223> OTHER INFORMATION: nonconsensus sequence of SEQ ID NOS:1-7
<220> FEATURE:
<221> NAME/KEY: MISC_FEATURE
<222> LOCATION: (16)..(18)
<223> OTHER INFORMATION: nonconsensus sequence of SEQ ID NOS:1-7
<220> FEATURE:
<221> NAME/KEY: MISC_FEATURE
<222> LOCATION: (20)..(25)
<223> OTHER INFORMATION: nonconsensus sequence of SEQ ID NOS:1-7
<220> FEATURE:
<221> NAME/KEY: MISC_FEATURE
<222> LOCATION: (28)..(28)
<223> OTHER INFORMATION: nonconsensus sequence of SEQ ID NOS:1-7
<220> FEATURE:
<221> NAME/KEY: MISC_FEATURE
<222> LOCATION: (33)..(33)
<223> OTHER INFORMATION: nonconsensus sequence of SEQ ID NOS:1-7
<220> FEATURE:
<221> NAME/KEY: MISC_FEATURE
<222> LOCATION: (36)..(36)
<223> OTHER INFORMATION: nonconsensus sequence of SEQ ID NOS:1-7
<220> FEATURE:
<221> NAME/KEY: MISC_FEATURE
<222> LOCATION: (39)..(40)
<223> OTHER INFORMATION: nonconsensus sequence of SEQ ID NOS:1-7
<220> FEATURE:
<221> NAME/KEY: MISC_FEATURE
<222> LOCATION: (42)..(50)
<223> OTHER INFORMATION: nonconsensus sequence of SEQ ID NOS:1-7
<220> FEATURE:
<221> NAME/KEY: MISC_FEATURE
<222> LOCATION: (52)..(52)
<223> OTHER INFORMATION: nonconsensus sequence of SEQ ID NOS:1-7
<220> FEATURE:
```

```
<221> NAME/KEY: MISC_FEATURE
<222> LOCATION: (56)..(56)
<223> OTHER INFORMATION: nonconsensus sequence of SEQ ID NOS:1-7
<220> FEATURE:
<221> NAME/KEY: MISC_FEATURE
<222> LOCATION: (61)..(62)
<223> OTHER INFORMATION: nonconsensus sequence of SEQ ID NOS:1-7
<220> FEATURE:
<221> NAME/KEY: MISC_FEATURE
<222> LOCATION: (64)..(66)
<223> OTHER INFORMATION: nonconsensus sequence of SEQ ID NOS:1-7
<220> FEATURE:
<221> NAME/KEY: MISC_FEATURE
<222> LOCATION: (68)..(68)
<223> OTHER INFORMATION: nonconsensus sequence of SEQ ID NOS:1-7
<220> FEATURE:
<221> NAME/KEY: MISC_FEATURE
<222> LOCATION: (70)..(71)
<223> OTHER INFORMATION: nonconsensus sequence of SEQ ID NOS:1-7
<220> FEATURE:
<221> NAME/KEY: MISC_FEATURE
<222> LOCATION: (74)..(75)
<223> OTHER INFORMATION: nonconsensus sequence of SEQ ID NOS:1-7
<220> FEATURE:
<221> NAME/KEY: MISC_FEATURE
<222> LOCATION: (80)..(81)
<223> OTHER INFORMATION: nonconsensus sequence of SEQ ID NOS:1-7
<220> FEATURE:
<221> NAME/KEY: MISC_FEATURE
<222> LOCATION: (83)..(85)
<223> OTHER INFORMATION: nonconsensus sequence of SEQ ID NOS:1-7

<400> SEQUENCE: 8

Asp Leu Xaa Xaa Xaa Xaa Val Thr Gly Ile Ile Thr Gln Gly Xaa
1               5                   10                  15

Xaa Xaa Lys Xaa Xaa Xaa Xaa Xaa Phe Val Xaa Ser Tyr Lys Ile
            20                  25                  30

Xaa Tyr Ser Xaa Asp Gly Xaa Xaa Trp Xaa Xaa Xaa Xaa Xaa Xaa
            35                  40                  45

Xaa Xaa Lys Xaa Lys Val Phe Xaa Gly Asn Thr Asp Xaa Xaa Thr Xaa
        50                  55                  60

Xaa Xaa Asn Xaa Phe Xaa Xaa Pro Ile Xaa Xaa Arg Phe Ile Arg Xaa
65                  70                  75                  80

Xaa Pro Xaa Xaa Xaa
            85

<210> SEQ ID NO 9
<211> LENGTH: 2303
<212> TYPE: DNA
<213> ORGANISM: Mus sp.
<220> FEATURE:
<221> NAME/KEY: CDS
<222> LOCATION: (619)..(2058)

<400> SEQUENCE: 9
gaattccggt taactgagga caaagggtaa tgcagaagtg atatttgatt tccattctca      60
ttcccagtgg ccttgatatt taaactgatt cctgccacca ggtccttggg ccaccctgtc     120
cctgcgtctc atatttctgc atgctgcttt gtttgtatat agtgcgctcc tggcctcagg     180
ctcgctcccc tccagctctc gcttcattgt tctccaagtc agaagccccc gcatccgccg     240
cgcagcagcg tgagccgtag tcactgctgg ccgcttcgcc tgcgtgcgcg cacgaaaatc     300
ggggagccag gaacccaagg agccgccgtc cgcccgctgt gcctctgcta gaccactcgc     360
agccccagcc tctctcaagc gcacccacct ccgcgcaccc cagctcaggc gaagctggag     420
tgagggtgaa tcacccttc tctagggcca ccactctttt atcgcccttc ccaagatttg      480
```

```
                                                      -continued agaagcgctg cgggaggaaa gacgtcctct tgatctctga cagggcgggg tttactgctg    540
tcctgcaggc gcgcctcgcc tactgtgccc tccgctacga ccccggacca gcccaggtca    600
cgtccgtgag aagggatc atg aag cac ttg gta gca gcc tgg ctt ttg gtt     651
                    Met Lys His Leu Val Ala Ala Trp Leu Leu Val
                     1               5                  10 gga ctc agc ctc ggg gtg ccc cag ttc ggc aaa ggt gac att tgc aac     699
Gly Leu Ser Leu Gly Val Pro Gln Phe Gly Lys Gly Asp Ile Cys Asn
            15                  20                  25 ccg aac ccc tgt gaa aat ggt ggc atc tgt ctg tca gga ctg gct gat     747
Pro Asn Pro Cys Glu Asn Gly Gly Ile Cys Leu Ser Gly Leu Ala Asp
        30                  35                  40 gat tcc ttt tcc tgt gag tgt cca gaa ggc ttc gca ggt ccg aac tgc     795
Asp Ser Phe Ser Cys Glu Cys Pro Glu Gly Phe Ala Gly Pro Asn Cys
    45                  50                  55 tct agt gtt gtg gag gtt gca tca gat gaa gaa aag cct act tca gca     843
Ser Ser Val Val Glu Val Ala Ser Asp Glu Glu Lys Pro Thr Ser Ala
60                  65                  70                  75 ggt ccc tgc atc cct aac cca tgc cat aac gga gga acc tgt gag ata     891
Gly Pro Cys Ile Pro Asn Pro Cys His Asn Gly Gly Thr Cys Glu Ile
                80                  85                  90 agc gaa gcc tat cga gga gac aca ttc ata ggc tat gtt tgt aaa tgt     939
Ser Glu Ala Tyr Arg Gly Asp Thr Phe Ile Gly Tyr Val Cys Lys Cys
            95                  100                 105 cct cgg gga ttt aat ggg att cac tgt cag cac aat ata aat gaa tgt     987
Pro Arg Gly Phe Asn Gly Ile His Cys Gln His Asn Ile Asn Glu Cys
        110                 115                 120 gaa gct gag cct tgc aga aat ggc gga ata tgt acc gac ctt gtt gct     1035
Glu Ala Glu Pro Cys Arg Asn Gly Gly Ile Cys Thr Asp Leu Val Ala
    125                 130                 135 aac tac tct tgt gaa tgc cca gga gaa ttt atg gga cga aat tgt caa     1083
Asn Tyr Ser Cys Glu Cys Pro Gly Glu Phe Met Gly Arg Asn Cys Gln
140                 145                 150                 155 tat aaa tgc tct ggg cac ttg gga atc gaa ggt ggg atc ata tct aat     1131
Tyr Lys Cys Ser Gly His Leu Gly Ile Glu Gly Gly Ile Ile Ser Asn
                160                 165                 170 cag caa atc aca gct tca tct aat cac cga gct ctt ttt gga ctc cag     1179
Gln Gln Ile Thr Ala Ser Ser Asn His Arg Ala Leu Phe Gly Leu Gln
            175                 180                 185 aag tgg tat ccc tac tat gct cga ctt aat aag aag ggc ctt ata aat     1227
Lys Trp Tyr Pro Tyr Tyr Ala Arg Leu Asn Lys Lys Gly Leu Ile Asn
        190                 195                 200 gcc tgg aca gct gct gaa aat gac aga tgg cca tgg att cag ata aat     1275
Ala Trp Thr Ala Ala Glu Asn Asp Arg Trp Pro Trp Ile Gln Ile Asn
    205                 210                 215 ttg caa aga aaa atg aga gtc act ggt gtt att acc caa gga gca aaa     1323
Leu Gln Arg Lys Met Arg Val Thr Gly Val Ile Thr Gln Gly Ala Lys
220                 225                 230                 235 agg att gga agc cca gag tac ata aaa tcc tac aaa att gcc tac agc     1371
Arg Ile Gly Ser Pro Glu Tyr Ile Lys Ser Tyr Lys Ile Ala Tyr Ser
                240                 245                 250 aat gac ggg aag acc tgg gca atg tac aaa gta aaa ggc acc aat gaa     1419
Asn Asp Gly Lys Thr Trp Ala Met Tyr Lys Val Lys Gly Thr Asn Glu
            255                 260                 265 gag atg gtc ttt cgt gga aat gtt gat aac aac aca cca tat gct aat     1467
Glu Met Val Phe Arg Gly Asn Val Asp Asn Asn Thr Pro Tyr Ala Asn
        270                 275                 280 tct ttc aca ccc cca atc aaa gct cag tat gta aga ctc tac ccc caa     1515
Ser Phe Thr Pro Pro Ile Lys Ala Gln Tyr Val Arg Leu Tyr Pro Gln
    285                 290                 295
```

```
att tgt cga agg cat tgt act tta aga atg gaa ctt ctt ggc tgt gag      1563
Ile Cys Arg Arg His Cys Thr Leu Arg Met Glu Leu Leu Gly Cys Glu
300                 305                 310                 315 ctc tca ggc tgt tca gaa cct ttg ggg atg aaa tca ggg cat ata caa      1611
Leu Ser Gly Cys Ser Glu Pro Leu Gly Met Lys Ser Gly His Ile Gln
            320                 325                 330 gac tac cag atc act gcc tcc agc gtc ttc aga aca ctc aac atg gac      1659
Asp Tyr Gln Ile Thr Ala Ser Ser Val Phe Arg Thr Leu Asn Met Asp
335                 340                 345 atg ttt act tgg gaa cca agg aaa gcc agg ctg gac aag caa ggc aaa      1707
Met Phe Thr Trp Glu Pro Arg Lys Ala Arg Leu Asp Lys Gln Gly Lys
        350                 355                 360 gta aat gcc tgg act tcc ggc cat aac gac cag tca caa tgg tta cag      1755
Val Asn Ala Trp Thr Ser Gly His Asn Asp Gln Ser Gln Trp Leu Gln
365                 370                 375 gtt gat ctt ctt gtc cct act aag gtg aca ggc atc att aca caa gga      1803
Val Asp Leu Leu Val Pro Thr Lys Val Thr Gly Ile Ile Thr Gln Gly
380                 385                 390                 395 gct aaa gat ttt ggt cac gtg cag ttt gtt ggg tca tac aaa cta gct      1851
Ala Lys Asp Phe Gly His Val Gln Phe Val Gly Ser Tyr Lys Leu Ala
            400                 405                 410 tac agc aat gat gga gaa cac tgg atg gtg cac cag gat gaa aaa cag      1899
Tyr Ser Asn Asp Gly Glu His Trp Met Val His Gln Asp Glu Lys Gln
        415                 420                 425 agg aaa gac aag gtt ttt caa ggc aat ttt gac aat gac act cac agg      1947
Arg Lys Asp Lys Val Phe Gln Gly Asn Phe Asp Asn Asp Thr His Arg
430                 435                 440 aaa aat gtc atc gac cct ccc atc tat gca cga ttc ata aga atc ctt      1995
Lys Asn Val Ile Asp Pro Pro Ile Tyr Ala Arg Phe Ile Arg Ile Leu
        445                 450                 455 cct tgg tcc tgg tat gga agg atc act ctg cgg tca gag ctg ctg ggc      2043
Pro Trp Ser Trp Tyr Gly Arg Ile Thr Leu Arg Ser Glu Leu Leu Gly
460                 465                 470                 475 tgc gca gag gag gaa tgaagtgcgg ggccgcacat cccacaatgc ttttctttat     2098
Cys Ala Glu Glu Glu
                480 tttcctataa gtatctccac gaaatgaact gtgtgaagct gatggaaact gcatttgttt     2158 ttttcaaagt gttcaaatta tggtaggcta ctgactgtct ttttaggagt tctaagcttg     2218 ccttttttaat aatttaattt ggtttccttt gctcaactct cttatgtaat atcacactgt    2278 ctgtgagtta ctcttcttgt tctct                                          2303

<210> SEQ ID NO 10
<211> LENGTH: 480
<212> TYPE: PRT
<213> ORGANISM: Mus sp.

<400> SEQUENCE: 10

Met Lys His Leu Val Ala Ala Trp Leu Leu Val Gly Leu Ser Leu Gly
1               5                   10                  15

Val Pro Gln Phe Gly Lys Gly Asp Ile Cys Asn Pro Asn Pro Cys Glu
            20                  25                  30

Asn Gly Gly Ile Cys Leu Ser Gly Leu Ala Asp Asp Ser Phe Ser Cys
        35                  40                  45

Glu Cys Pro Glu Gly Phe Ala Gly Pro Asn Cys Ser Ser Val Val Glu
    50                  55                  60

Val Ala Ser Asp Glu Glu Lys Pro Thr Ser Ala Gly Pro Cys Ile Pro
65                  70                  75                  80
```

```
Asn Pro Cys His Asn Gly Gly Thr Cys Glu Ile Ser Glu Ala Tyr Arg
             85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Ala Glu Pro Cys
            115                 120                 125

Arg Asn Gly Gly Ile Cys Thr Asp Leu Val Ala Asn Tyr Ser Cys Glu
    130                 135                 140

Cys Pro Gly Glu Phe Met Gly Arg Asn Cys Gln Tyr Lys Cys Ser Gly
145                 150                 155                 160

His Leu Gly Ile Glu Gly Ile Ile Ser Asn Gln Gln Ile Thr Ala
                165                 170                 175

Ser Ser Asn His Arg Ala Leu Phe Gly Leu Gln Lys Trp Tyr Pro Tyr
            180                 185                 190

Tyr Ala Arg Leu Asn Lys Lys Gly Leu Ile Asn Ala Trp Thr Ala Ala
            195                 200                 205

Glu Asn Asp Arg Trp Pro Trp Ile Gln Ile Asn Leu Gln Arg Lys Met
    210                 215                 220

Arg Val Thr Gly Val Ile Thr Gln Gly Ala Lys Arg Ile Gly Ser Pro
225                 230                 235                 240

Glu Tyr Ile Lys Ser Tyr Lys Ile Ala Tyr Ser Asn Asp Gly Lys Thr
                245                 250                 255

Trp Ala Met Tyr Lys Val Lys Gly Thr Asn Glu Glu Met Val Phe Arg
            260                 265                 270

Gly Asn Val Asp Asn Thr Pro Tyr Ala Asn Ser Phe Thr Pro Pro
            275                 280                 285

Ile Lys Ala Gln Tyr Val Arg Leu Tyr Pro Gln Ile Cys Arg Arg His
    290                 295                 300

Cys Thr Leu Arg Met Glu Leu Leu Gly Cys Glu Leu Ser Gly Cys Ser
305                 310                 315                 320

Glu Pro Leu Gly Met Lys Ser Gly His Ile Gln Asp Tyr Gln Ile Thr
                325                 330                 335

Ala Ser Ser Val Phe Arg Thr Leu Asn Met Asp Met Phe Thr Trp Glu
            340                 345                 350

Pro Arg Lys Ala Arg Leu Asp Lys Gln Gly Lys Val Asn Ala Trp Thr
            355                 360                 365

Ser Gly His Asn Asp Gln Ser Gln Trp Leu Gln Val Asp Leu Leu Val
    370                 375                 380

Pro Thr Lys Val Thr Gly Ile Ile Thr Gln Gly Ala Lys Asp Phe Gly
385                 390                 395                 400

His Val Gln Phe Val Gly Ser Tyr Lys Leu Ala Tyr Ser Asn Asp Gly
                405                 410                 415

Glu His Trp Met Val His Gln Asp Glu Lys Gln Arg Lys Asp Lys Val
            420                 425                 430

Phe Gln Gly Asn Phe Asp Asn Asp Thr His Arg Lys Asn Val Ile Asp
            435                 440                 445

Pro Pro Ile Tyr Ala Arg Phe Ile Arg Ile Leu Pro Trp Ser Trp Tyr
    450                 455                 460

Gly Arg Ile Thr Leu Arg Ser Glu Leu Leu Gly Cys Ala Glu Glu
465                 470                 475                 480

<210> SEQ ID NO 11
<211> LENGTH: 1780
```

```
<212> TYPE: DNA
<213> ORGANISM: homo sapiens
<220> FEATURE:
<221> NAME/KEY: CDS
<222> LOCATION: (1)..(1779)

<400> SEQUENCE: 11 tct ctt tag tca cca ctc tcg ccc tct cca aga att tgt tta aca aag        48
Ser Leu     Ser Pro Leu Ser Pro Ser Pro Arg Ile Cys Leu Thr Lys
1               5                   10                  15 cgc tga gga aag aga acg tct tct tga att ctt tag tag ggg cgg agt        96
Arg     Gly Lys Arg Thr Ser Ser     Ile Leu             Gly Arg Ser
                20                                  25 ctg ctg ctg ccc tgc gct gcc acc tcg gct aca ctg ccc tcc gcg acg       144
Leu Leu Leu Pro Cys Ala Ala Thr Ser Ala Thr Leu Pro Ser Ala Thr
            30                  35                  40 acc cct gac cag ccg ggg tca cgt ccg gga gac ggg atc atg aag cgc       192
Thr Pro Asp Gln Pro Gly Ser Arg Pro Gly Asp Gly Ile Met Lys Arg
        45                  50                  55 tcg gta gcc gtc tgg ctc ttg gtc ggg ctc agc ctc ggt gtc ccc cag       240
Ser Val Ala Val Trp Leu Leu Val Gly Leu Ser Leu Gly Val Pro Gln
60                  65                  70                  75 ttc ggc aaa ggt gat att tgt gat ccc aat cca tgt gaa aat gga ggt       288
Phe Gly Lys Gly Asp Ile Cys Asp Pro Asn Pro Cys Glu Asn Gly Gly
                80                  85                  90 atc tgt ttg cca gga ttg gct gta ggt tcc ttt tcc tgt gag tgt cca       336
Ile Cys Leu Pro Gly Leu Ala Val Gly Ser Phe Ser Cys Glu Cys Pro
            95                  100                 105 gat ggc ttc aca gac ccc aac tgt tct agt gtt gtg gag gtt gca tca       384
Asp Gly Phe Thr Asp Pro Asn Cys Ser Ser Val Val Glu Val Ala Ser
        110                 115                 120 gat gaa gaa gaa cca act tca gca ggt ccc tgc act cct aat cca tgc       432
Asp Glu Glu Glu Pro Thr Ser Ala Gly Pro Cys Thr Pro Asn Pro Cys
    125                 130                 135 cat aat gga gga acc tgt gaa ata agt gaa gca tac cga ggg gat aca       480
His Asn Gly Gly Thr Cys Glu Ile Ser Glu Ala Tyr Arg Gly Asp Thr
140                 145                 150                 155 ttc ata ggc tat gtt tgt aaa tgt ccc cga gga ttt aat ggg att cac       528
Phe Ile Gly Tyr Val Cys Lys Cys Pro Arg Gly Phe Asn Gly Ile His
                160                 165                 170 tgt cag cac aac ata aat gaa tgc gaa gtt gag cct tgc aaa aat ggt       576
Cys Gln His Asn Ile Asn Glu Cys Glu Val Glu Pro Cys Lys Asn Gly
            175                 180                 185 gga ata tgt aca gat ctt gtt gct aac tat tcc tgt gag tgc cca ggc       624
Gly Ile Cys Thr Asp Leu Val Ala Asn Tyr Ser Cys Glu Cys Pro Gly
        190                 195                 200 gaa ttt atg gga aga aat tgt caa tac aaa tgc tca ggc cca ctg gga       672
Glu Phe Met Gly Arg Asn Cys Gln Tyr Lys Cys Ser Gly Pro Leu Gly
    205                 210                 215 att gaa ggt gga att ata tca aac cag caa atc aca gct tcc tct act       720
Ile Glu Gly Gly Ile Ile Ser Asn Gln Gln Ile Thr Ala Ser Ser Thr
220                 225                 230                 235 cac cga gct ctt ttt gga ctc caa aaa tgg tat ccc tac tat gca cgt       768
His Arg Ala Leu Phe Gly Leu Gln Lys Trp Tyr Pro Tyr Tyr Ala Arg
                240                 245                 250 ctt aat aag aag ggg ctt ata aat gcg tgg aca gct gca gaa aat gac       816
Leu Asn Lys Lys Gly Leu Ile Asn Ala Trp Thr Ala Ala Glu Asn Asp
            255                 260                 265 aga tgg aac cgg tgg att cag ata aat ttg caa aga aaa atg aga gtt       864
Arg Trp Asn Arg Trp Ile Gln Ile Asn Leu Gln Arg Lys Met Arg Val
        270                 275                 280
```

```
act ggt gtg att acc caa ggg gcc aag agg att gga agc cca gag tat      912
Thr Gly Val Ile Thr Gln Gly Ala Lys Arg Ile Gly Ser Pro Glu Tyr
285                 290                 295 ata aaa ttc tac aaa att gcc tac agt aat gat gga aag act tgg gca      960
Ile Lys Phe Tyr Lys Ile Ala Tyr Ser Asn Asp Gly Lys Thr Trp Ala
300                 305                 310                 315 atg tac aaa gtg aaa ggc acc aat gaa gac atg gtg ttt cgt gga aac     1008
Met Tyr Lys Val Lys Gly Thr Asn Glu Asp Met Val Phe Arg Gly Asn
                320                 325                 330 att gat aac aac act cca tat gct aac tct ttc aca ccc ccc ata aaa     1056
Ile Asp Asn Asn Thr Pro Tyr Ala Asn Ser Phe Thr Pro Pro Ile Lys
            335                 340                 345 gct cag tat gta aga ctc tat ccc caa gtt tgt cga aga cat tgc act     1104
Ala Gln Tyr Val Arg Leu Tyr Pro Gln Val Cys Arg Arg His Cys Thr
        350                 355                 360 ttg cga atg gaa ctt ctt ggc tgt gaa ctg tcg ggt tgt tct gag cct     1152
Leu Arg Met Glu Leu Leu Gly Cys Glu Leu Ser Gly Cys Ser Glu Pro
    365                 370                 375 ctg ggt atg aaa tca gga cat ata caa gac tat cag atc act gcc tcc     1200
Leu Gly Met Lys Ser Gly His Ile Gln Asp Tyr Gln Ile Thr Ala Ser
380                 385                 390                 395 agc atc ttc aga acg ctc aac atg gac atg ttc act tgg gaa cca agg     1248
Ser Ile Phe Arg Thr Leu Asn Met Asp Met Phe Thr Trp Glu Pro Arg
                400                 405                 410 aaa gct cgg ctg gac aag caa ggc aaa gtg aat gcc tgg acc tct ggc     1296
Lys Ala Arg Leu Asp Lys Gln Gly Lys Val Asn Ala Trp Thr Ser Gly
            415                 420                 425 cac aat gac cag tca caa tgg tta cag gtg gat ctt ctt gtt cca acc     1344
His Asn Asp Gln Ser Gln Trp Leu Gln Val Asp Leu Leu Val Pro Thr
        430                 435                 440 aaa gtg act ggc atc att aca caa gga gct aaa gat ttt ggt cat gta     1392
Lys Val Thr Gly Ile Ile Thr Gln Gly Ala Lys Asp Phe Gly His Val
    445                 450                 455 cag ttt gtt ggc tcc tac aaa ctg gct tac agc aat gat gga gaa cac     1440
Gln Phe Val Gly Ser Tyr Lys Leu Ala Tyr Ser Asn Asp Gly Glu His
460                 465                 470                 475 tgg act gta tac cag gat gaa aag caa aga aaa gat aag gtt ttc cag     1488
Trp Thr Val Tyr Gln Asp Glu Lys Gln Arg Lys Asp Lys Val Phe Gln
                480                 485                 490 gga aat ttt gac aat gac act cac aga aaa aat gtc atc gac cct ccc     1536
Gly Asn Phe Asp Asn Asp Thr His Arg Lys Asn Val Ile Asp Pro Pro
            495                 500                 505 atc tat gca cga cac ata aga atc ctt cct tgg tcc tgg tac ggg agg     1584
Ile Tyr Ala Arg His Ile Arg Ile Leu Pro Trp Ser Trp Tyr Gly Arg
        510                 515                 520 atc aca ttg gcg tca gag ctg ctg ggc tgc aca gag gag gaa tga ggg     1632
Ile Thr Leu Ala Ser Glu Leu Leu Gly Cys Thr Glu Glu Glu     Gly
    525                 530                 535 gag gct aca ttt cac aac cgt ctt ccc tat ttg ggt aaa agt atc tcc     1680
Glu Ala Thr Phe His Asn Arg Leu Pro Tyr Leu Gly Lys Ser Ile Ser
540                 545                 550 atg gaa tga act gtg taa aat ctg tag gaa act gaa tgg ttt ttt ttt     1728
Met Glu     Thr Val     Asn Leu     Glu Thr Glu Trp Phe Phe Phe
555                         560 ttt tca tga aaa agt ggt caa att atg gta ggc aac taa cgg tgt ttt     1776
Phe Ser     Lys Ser Gly Gln Ile Met Val Gly Asn     Arg Cys Phe
            570                 575                 580 tac c                                                                1780
Tyr
```

<210> SEQ ID NO 12
<211> LENGTH: 14
<212> TYPE: PRT
<213> ORGANISM: homo sapiens

<400> SEQUENCE: 12

Ser Pro Leu Ser Pro Ser Pro Arg Ile Cys Leu Thr Lys Arg
1               5                   10

<210> SEQ ID NO 13
<211> LENGTH: 6
<212> TYPE: PRT
<213> ORGANISM: homo sapiens

<400> SEQUENCE: 13

Gly Lys Arg Thr Ser Ser
1               5

<210> SEQ ID NO 14
<211> LENGTH: 513
<212> TYPE: PRT
<213> ORGANISM: homo sapiens

<400> SEQUENCE: 14

Gly Arg Ser Leu Leu Pro Cys Ala Ala Thr Ser Ala Thr Leu Pro
1               5                   10                  15

Ser Ala Thr Thr Pro Asp Gln Pro Gly Ser Arg Pro Gly Asp Gly Ile
                20                  25                  30

Met Lys Arg Ser Val Ala Val Trp Leu Leu Val Gly Leu Ser Leu Gly
            35                  40                  45

Val Pro Gln Phe Gly Lys Gly Asp Ile Cys Asp Pro Asn Pro Cys Glu
    50                  55                  60

Asn Gly Gly Ile Cys Leu Pro Gly Leu Ala Val Gly Ser Phe Ser Cys
65                  70                  75                  80

Glu Cys Pro Asp Gly Phe Thr Asp Pro Asn Cys Ser Ser Val Val Glu
                85                  90                  95

Val Ala Ser Asp Glu Glu Pro Thr Ser Ala Gly Pro Cys Thr Pro
                100                 105                 110

Asn Pro Cys His Asn Gly Gly Thr Cys Glu Ile Ser Glu Ala Tyr Arg
            115                 120                 125

Gly Asp Thr Phe Ile Gly Tyr Val Cys Lys Cys Pro Arg Gly Phe Asn
    130                 135                 140

Gly Ile His Cys Gln His Asn Ile Asn Glu Cys Glu Val Glu Pro Cys
145                 150                 155                 160

Lys Asn Gly Gly Ile Cys Thr Asp Leu Val Ala Asn Tyr Ser Cys Glu
                165                 170                 175

Cys Pro Gly Glu Phe Met Gly Arg Asn Cys Gln Tyr Lys Cys Ser Gly
            180                 185                 190

Pro Leu Gly Ile Glu Gly Gly Ile Ile Ser Asn Gln Gln Ile Thr Ala
    195                 200                 205

Ser Ser Thr His Arg Ala Leu Phe Gly Leu Gln Lys Trp Tyr Pro Tyr
210                 215                 220

Tyr Ala Arg Leu Asn Lys Lys Gly Leu Ile Asn Ala Trp Thr Ala Ala
225                 230                 235                 240

Glu Asn Asp Arg Trp Asn Arg Trp Ile Gln Ile Asn Leu Gln Arg Lys
                245                 250                 255

-continued

```
Met Arg Val Thr Gly Val Ile Thr Gln Gly Ala Lys Arg Ile Gly Ser
            260                 265                 270

Pro Glu Tyr Ile Lys Phe Tyr Lys Ile Ala Tyr Ser Asn Asp Gly Lys
        275                 280                 285

Thr Trp Ala Met Tyr Lys Val Lys Gly Thr Asn Glu Asp Met Val Phe
    290                 295                 300

Arg Gly Asn Ile Asp Asn Asn Thr Pro Tyr Ala Asn Ser Phe Thr Pro
305                 310                 315                 320

Pro Ile Lys Ala Gln Tyr Val Arg Leu Tyr Pro Gln Val Cys Arg Arg
                325                 330                 335

His Cys Thr Leu Arg Met Glu Leu Leu Gly Cys Glu Leu Ser Gly Cys
            340                 345                 350

Ser Glu Pro Leu Gly Met Lys Ser Gly His Ile Gln Asp Tyr Gln Ile
        355                 360                 365

Thr Ala Ser Ser Ile Phe Arg Thr Leu Asn Met Asp Met Phe Thr Trp
    370                 375                 380

Glu Pro Arg Lys Ala Arg Leu Asp Lys Gln Gly Lys Val Asn Ala Trp
385                 390                 395                 400

Thr Ser Gly His Asn Asp Gln Ser Gln Trp Leu Gln Val Asp Leu Leu
                405                 410                 415

Val Pro Thr Lys Val Thr Gly Ile Ile Thr Gln Gly Ala Lys Asp Phe
            420                 425                 430

Gly His Val Gln Phe Val Gly Ser Tyr Lys Leu Ala Tyr Ser Asn Asp
        435                 440                 445

Gly Glu His Trp Thr Val Tyr Gln Asp Glu Lys Gln Arg Lys Asp Lys
    450                 455                 460

Val Phe Gln Gly Asn Phe Asp Asn Asp Thr His Arg Lys Asn Val Ile
465                 470                 475                 480

Asp Pro Pro Ile Tyr Ala Arg His Ile Arg Ile Leu Pro Trp Ser Trp
                485                 490                 495

Tyr Gly Arg Ile Thr Leu Ala Ser Glu Leu Leu Gly Cys Thr Glu Glu
            500                 505                 510

Glu
```

<210> SEQ ID NO 15
<211> LENGTH: 19
<212> TYPE: PRT
<213> ORGANISM: homo sapiens

<400> SEQUENCE: 15

```
Gly Glu Ala Thr Phe His Asn Arg Leu Pro Tyr Leu Gly Lys Ser Ile
1               5                   10                  15

Ser Met Glu
```

<210> SEQ ID NO 16
<211> LENGTH: 9
<212> TYPE: PRT
<213> ORGANISM: homo sapiens

<400> SEQUENCE: 16

```
Glu Thr Glu Trp Phe Phe Phe Phe Ser
1               5
```

<210> SEQ ID NO 17
<211> LENGTH: 9
<212> TYPE: PRT
<213> ORGANISM: homo sapiens

-continued

```
<400> SEQUENCE: 17

Lys Ser Gly Gln Ile Met Val Gly Asn
1               5

<210> SEQ ID NO 18
<211> LENGTH: 4
<212> TYPE: PRT
<213> ORGANISM: homo sapiens

<400> SEQUENCE: 18

Arg Cys Phe Tyr
1

<210> SEQ ID NO 19
<211> LENGTH: 318
<212> TYPE: DNA
<213> ORGANISM: mus sp.

<400> SEQUENCE: 19
gacagatggc catggattca gataaatttg caaagaaaaa tgagagtcac tggtgttatt      60
acccaaggag caaaaaggat tggaagccca gagtacataa aatcctacaa aattgcctac     120
agcaatgacg ggaagacctg ggcaatgtac aaagtaaaag gcaccaatga agagatggtc     180
tttcgtggaa atgttgataa caacacacca tatgctaatt ctttcacacc cccaatcaaa     240
gctcagtatg taagactcta cccccaaatt tgtcgaaggc attgtacttt aagaatggaa     300
cttcttggct gtgagctc                                                   318

<210> SEQ ID NO 20
<211> LENGTH: 316
<212> TYPE: PRT
<213> ORGANISM: homo sapiens

<400> SEQUENCE: 20

Cys Ser Thr Gln Leu Gly Met Glu Gly Gly Ala Ile Ala Asp Ser Gln
1               5                   10                  15

Ile Ser Ala Ser Tyr Val Tyr Met Gly Phe Met Gly Leu Gln Arg Trp
            20                  25                  30

Gly Pro Glu Leu Ala Arg Leu Tyr Arg Thr Gly Ile Val Asn Ala Trp
        35                  40                  45

His Ala Ser Asn Tyr Asp Ser Lys Pro Trp Ile Gln Val Asn Leu Leu
    50                  55                  60

Arg Lys Met Arg Val Ser Gly Val Met Thr Gln Gly Ala Ser Arg Ala
65                  70                  75                  80

Gly Arg Ala Glu Tyr Leu Lys Thr Phe Lys Val Ala Tyr Ser Leu Asp
                85                  90                  95

Gly Arg Lys Phe Glu Phe Ile Gln Asp Glu Ser Gly Gly Asp Lys Glu
            100                 105                 110

Phe Leu Gly Asn Leu Asp Asn Asn Ser Leu Lys Val Asn Met Phe Asn
        115                 120                 125

Pro Thr Leu Glu Ala Gln Tyr Ile Arg Leu Tyr Pro Val Ser Cys His
    130                 135                 140

Arg Gly Cys Thr Leu Arg Phe Glu Leu Leu Gly Cys Glu Leu His Gly
145                 150                 155                 160

Cys Leu Glu Pro Leu Gly Leu Lys Asn Asn Thr Ile Pro Asp Ser Gln
                165                 170                 175

Met Ser Ala Ser Ser Ser Tyr Lys Thr Trp Asn Leu Arg Ala Phe Gly
```

```
                    180             185              190
Trp Tyr Pro His Leu Gly Arg Leu Asp Asn Gln Gly Lys Ile Asn Ala
        195                 200                 205

Trp Thr Ala Gln Ser Asn Ser Ala Lys Glu Trp Leu Gln Val Asp Leu
    210                 215                 220

Gly Thr Gln Arg Gln Val Thr Gly Ile Ile Thr Gln Gly Ala Arg Asp
225                 230                 235                 240

Phe Gly His Ile Gln Tyr Val Glu Ser Tyr Lys Val Ala His Ser Asp
                245                 250                 255

Asp Gly Val Gln Trp Thr Val Tyr Glu Glu Gln Gly Ser Ser Lys Val
                260                 265                 270

Phe Gln Gly Asn Leu Asp Asn Asn Ser His Lys Lys Asn Ile Phe Glu
            275                 280                 285

Lys Pro Phe Met Ala Arg Tyr Val Arg Val Leu Pro Val Ser Trp His
        290                 295                 300

Asn Arg Ile Thr Leu Arg Leu Glu Leu Leu Gly Cys
305                 310                 315

<210> SEQ ID NO 21
<211> LENGTH: 321
<212> TYPE: PRT
<213> ORGANISM: homo sapiens
<220> FEATURE:
<221> NAME/KEY: UNSURE
<222> LOCATION: (225)..(225)
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: UNSURE
<222> LOCATION: (243)..(243)
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: UNSURE
<222> LOCATION: (266)..(266)
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: UNSURE
<222> LOCATION: (277)..(277)
<220> FEATURE:
<221> NAME/KEY: misc_feature
<222> LOCATION: (277)..(277)
<223> OTHER INFORMATION: Xaa can be any naturally occurring amino acid

<400> SEQUENCE: 21

Cys Ser Gly Pro Leu Gly Ile Glu Gly Gly Ile Ile Ser Asn Gln Gln
1               5                   10                  15

Ile Thr Ala Ser Ser Thr His Arg Ala Leu Phe Gly Leu Gln Lys Trp
            20                  25                  30

Tyr Pro Tyr Tyr Ala Arg Leu Asn Lys Lys Gly Leu Ile Asn Ala Trp
        35                  40                  45

Thr Ala Ala Glu Asn Asp Arg Trp Asn Arg Trp Ile Gln Ile Asn Leu
    50                  55                  60

Gln Arg Lys Met Arg Val Thr Gly Val Ile Thr Gln Gly Ala Lys Arg
65                  70                  75                  80

Ile Gly Ser Pro Glu Tyr Ile Lys Phe Tyr Lys Ile Ala Tyr Ser Asn
                85                  90                  95
```

```
Asp Gly Lys Thr Trp Ala Met Tyr Lys Val Lys Gly Thr Asn Glu Asp
            100                 105                 110

Met Val Phe Arg Gly Asn Ile Asp Asn Asn Thr Pro Tyr Ala Asn Ser
        115                 120                 125

Phe Thr Pro Pro Ile Lys Ala Gln Tyr Val Arg Leu Tyr Pro Gln Val
    130                 135                 140

Cys Arg Arg His Cys Thr Leu Arg Met Glu Leu Leu Gly Cys Glu Leu
145                 150                 155                 160

Ser Gly Cys Ser Glu Pro Leu Gly Met Lys Ser Gly His Ile Gln Asp
                165                 170                 175

Tyr Gln Ile Thr Ala Ser Ser Ile Phe Arg Thr Leu Asn Met Asp Met
            180                 185                 190

Phe Thr Trp Glu Pro Arg Lys Ala Arg Leu Asp Lys Gln Gly Lys Val
        195                 200                 205

Asn Ala Trp Thr Ser Gly His Asn Asp Gln Ser Gln Trp Leu Gln Val
    210                 215                 220

Xaa Leu Leu Val Pro Thr Lys Val Thr Gly Ile Ile Thr Gln Gly Ala
225                 230                 235                 240

Lys Asp Xaa Gly His Val Gln Phe Val Gly Ser Tyr Lys Leu Ala Tyr
                245                 250                 255

Ser Asn Asp Gly Glu His Trp Thr Val Xaa Gln Asp Glu Lys Gln Arg
            260                 265                 270

Lys Asp Lys Val Xaa Gln Gly Asn Phe Asp Asn Asp Thr His Arg Lys
        275                 280                 285

Asn Val Ile Asp Pro Pro Ile Tyr Ala Arg His Ile Arg Ile Leu Pro
    290                 295                 300

Trp Ser Trp Tyr Gly Arg Ile Thr Leu Ala Ser Glu Leu Leu Gly Cys
305                 310                 315                 320

Thr

<210> SEQ ID NO 22
<211> LENGTH: 25
<212> TYPE: PRT
<213> ORGANISM: homo sapiens

<400> SEQUENCE: 22

Met Lys Arg Ser Val Ala Val Trp Leu Leu Val Gly Leu Ser Leu Gly
1               5                   10                  15

Val Pro Gln Phe Gly Lys Gly Asp Ile
            20                  25

<210> SEQ ID NO 23
<211> LENGTH: 52
<212> TYPE: PRT
<213> ORGANISM: homo sapiens

<400> SEQUENCE: 23

Cys Asp Pro Asn Pro Cys Glu Asn Gly Gly Ile Cys Leu Pro Gly Leu
1               5                   10                  15

Ala Val Gly Ser Phe Ser Cys Glu Cys Pro Asp Gly Phe Thr Asp Pro
            20                  25                  30

Asn Cys Ser Ser Val Val Glu Val Ala Ser Asp Glu Glu Pro Thr
            35                  40                  45

Ser Ala Gly Pro
    50
```

```
<210> SEQ ID NO 24
<211> LENGTH: 45
<212> TYPE: PRT
<213> ORGANISM: homo sapiens

<400> SEQUENCE: 24

Cys Thr Pro Asn Pro Cys His Asn Gly Gly Thr Cys Glu Ile Ser Glu
1               5                   10                  15

Ala Tyr Arg Gly Asp Thr Phe Ile Gly Tyr Val Cys Lys Cys Pro Arg
            20                  25                  30

Gly Phe Asn Gly Ile His Cys Gln His Asn Ile Asn Glu
        35                  40                  45

<210> SEQ ID NO 25
<211> LENGTH: 35
<212> TYPE: PRT
<213> ORGANISM: homo sapiens

<400> SEQUENCE: 25

Cys Glu Val Glu Pro Cys Lys Asn Gly Gly Ile Cys Thr Asp Leu Val
1               5                   10                  15

Ala Asn Tyr Ser Cys Glu Cys Pro Gly Glu Phe Met Gly Arg Asn Cys
            20                  25                  30

Gln Tyr Lys
        35

<210> SEQ ID NO 26
<211> LENGTH: 40
<212> TYPE: PRT
<213> ORGANISM: artificial sequence
<220> FEATURE:
<223> OTHER INFORMATION: Consensus EGF domain
<220> FEATURE:
<221> NAME/KEY: MISC_FEATURE
<222> LOCATION: (2)..(4)
<223> OTHER INFORMATION: nonconsensus sequence
<220> FEATURE:
<221> NAME/KEY: MISC_FEATURE
<222> LOCATION: (7)..(7)
<223> OTHER INFORMATION: nonconsensus sequence
<220> FEATURE:
<221> NAME/KEY: MISC_FEATURE
<222> LOCATION: (11)..(11)
<223> OTHER INFORMATION: nonconsensus sequence
<220> FEATURE:
<221> NAME/KEY: MISC_FEATURE
<222> LOCATION: (13)..(25)
<223> OTHER INFORMATION: nonconsensus sequence
<220> FEATURE:
<221> NAME/KEY: MISC_FEATURE
<222> LOCATION: (26)..(26)
<223> OTHER INFORMATION: Y or F
<220> FEATURE:
<221> NAME/KEY: MISC_FEATURE
<222> LOCATION: (27)..(27)
<223> OTHER INFORMATION: nonconsensus sequence
<220> FEATURE:
<221> NAME/KEY: MISC_FEATURE
<222> LOCATION: (29)..(29)
<223> OTHER INFORMATION: nonconsensus sequence
<220> FEATURE:
<221> NAME/KEY: MISC_FEATURE
<222> LOCATION: (31)..(32)
<223> OTHER INFORMATION: nonconsensus sequence
<220> FEATURE:
<221> NAME/KEY: MISC_FEATURE
<222> LOCATION: (34)..(34)
<223> OTHER INFORMATION: Y or F
<220> FEATURE:
<221> NAME/KEY: MISC_FEATURE
```

```
<222> LOCATION: (35)..(35)
<223> OTHER INFORMATION: nonconsensus sequence
<220> FEATURE:
<221> NAME/KEY: MISC_FEATURE
<222> LOCATION: (37)..(38)
<223> OTHER INFORMATION: nonconsensus sequence
<220> FEATURE:
<221> NAME/KEY: MISC_FEATURE
<222> LOCATION: (40)..(40)
<223> OTHER INFORMATION: nonconsensus sequence

<400> SEQUENCE: 26

Cys Xaa Xaa Xaa Pro Cys Xaa Asn Gly Gly Xaa Cys Xaa Xaa Xaa Xaa
1               5                   10                  15

Xaa Xaa Xaa Xaa Xaa Xaa Xaa Xaa Xaa Xaa Cys Xaa Cys Xaa Xaa
            20                  25                  30

Gly Xaa Xaa Gly Xaa Xaa Cys Xaa
        35                  40

<210> SEQ ID NO 27
<211> LENGTH: 310
<212> TYPE: DNA
<213> ORGANISM: homo sapiens
<220> FEATURE:
<221> NAME/KEY: misc_feature
<222> LOCATION: (1)..(1)
<223> OTHER INFORMATION: n is a, c, g, t or u

<400> SEQUENCE: 27
ngtgatattt gtgatcccaa tccatgtgaa aatggaggta tctgtttgcc aggattggct      60
gtaggttcct tttcctgtga gtgtccagat ggcttcacag accccaactg ttctagtgtt    120
gtggaggttg gtccctgcac tcctaatcca tgccataatg gaggaacctg tgaaataagt    180
gaagcatacc gagggatac attcataggc tatgtttgta aatgtccccg aggatttaat    240
gggattcact gtcagcacaa cataaatgaa tgcgaagttg agccttgcaa aaatggtgga    300
atatgtacag                                                            310

<210> SEQ ID NO 28
<211> LENGTH: 2308
<212> TYPE: DNA
<213> ORGANISM: mus sp.
<220> FEATURE:
<221> NAME/KEY: CDS
<222> LOCATION: (550)..(1212)
<220> FEATURE:
<221> NAME/KEY: misc_feature
<222> LOCATION: (1819)..(1821)
<223> OTHER INFORMATION: n is a, c, g, t or u

<400> SEQUENCE: 28
gaattccggg agggagggta gggggggcggg ccgcggggc ccaaagccag ctaggctcag       60
tctcacacgc gcgccgccac tgtttgtata tagtgcgctc ctggcctcag gctcgctccc    120
ctccagctct cgcttcattg ttctccaagt cagaagcccc cgcatccgcc gcgcagcagc    180
gtgagccgta gtcactgctg gccgcttcgc ctgcgtgcgc gcacggaaat cggggagcca    240
ggaacccaag gagccgccgt ccgcccgctg tgcctctgct agaccactcg cagccccagc    300
ctctctcaag cgcacccacc tccgcgcacc ccagctcagg cgaagctgga gtgagggtga    360
atcacccttt ctctagggcc accactcttt tatcgcccct cccaagattt gagaagcgct    420 gcggaggaa agacgtcctc ttgatctctg cagggcggg gtttactgct gtcctgcagg    480
cgcgcctcgc ctactgtgcc ctccgctacg acccccggacc agcccaggtc acgtccgtga    540
```

```
gaagggatc atg aag cac ttg gta gca gcc tgg ctt ttg gtt gga ctc agc    591
          Met Lys His Leu Val Ala Ala Trp Leu Leu Val Gly Leu Ser
          1               5                   10 ctc ggg gtg ccc cag ttc ggc aaa ggt gac att tgc aac ccg aac ccc      639
Leu Gly Val Pro Gln Phe Gly Lys Gly Asp Ile Cys Asn Pro Asn Pro
15              20                  25                  30 tgt gaa aat ggt ggc atc tgt ctg tca gga ctg gct gat gat tcc ttt      687
Cys Glu Asn Gly Gly Ile Cys Leu Ser Gly Leu Ala Asp Asp Ser Phe
                35                  40                  45 tcc tgt gag tgt cca gaa ggc ttc gca ggt ccg aac tgc tct agt gtt      735
Ser Cys Glu Cys Pro Glu Gly Phe Ala Gly Pro Asn Cys Ser Ser Val
        50                  55                  60 gtg gag gtt gca tca gat gaa gaa aag cct act tca gca ggt ccc tgc      783
Val Glu Val Ala Ser Asp Glu Glu Lys Pro Thr Ser Ala Gly Pro Cys
            65                  70                  75 atc cct aac cca tgc cat aac gga gga acc tgt gag ata agc gaa gcc      831
Ile Pro Asn Pro Cys His Asn Gly Gly Thr Cys Glu Ile Ser Glu Ala
    80                  85                  90 tat cga gga gac aca ttc ata ggc tat gtt tgt aaa tgt cct cgg gga      879
Tyr Arg Gly Asp Thr Phe Ile Gly Tyr Val Cys Lys Cys Pro Arg Gly
95                  100                 105                 110 ttt aat ggg att cac tgt cag cac aat ata aat gaa tgt gaa gct gag      927
Phe Asn Gly Ile His Cys Gln His Asn Ile Asn Glu Cys Glu Ala Glu
                115                 120                 125 cct tgc aga aat ggc gga ata tgt acc gac ctt gtt gct aac tac tct      975
Pro Cys Arg Asn Gly Gly Ile Cys Thr Asp Leu Val Ala Asn Tyr Ser
        130                 135                 140 tgt gaa tgc cca gga gaa ttt atg gga cga aat tgt caa tat aaa tgc      1023
Cys Glu Cys Pro Gly Glu Phe Met Gly Arg Asn Cys Gln Tyr Lys Cys
            145                 150                 155 tct ggg cac ttg gga atc gaa ggt ggg atc ata tct aat cag caa atc      1071
Ser Gly His Leu Gly Ile Glu Gly Gly Ile Ile Ser Asn Gln Gln Ile
    160                 165                 170 aca gct tca tct aat cac cga gct ctt ttt gga ctc cag aag tgg tat      1119
Thr Ala Ser Ser Asn His Arg Ala Leu Phe Gly Leu Gln Lys Trp Tyr
175                 180                 185                 190 ccc tac tat gct aga ctt aat aag aag ggc ctt ata aat gcc tgg aca      1167
Pro Tyr Tyr Ala Arg Leu Asn Lys Lys Gly Leu Ile Asn Ala Trp Thr
                195                 200                 205 gct gct gaa aat gac aga tgg cca tgg att cag gta aca gtg gga           1212
Ala Ala Glu Asn Asp Arg Trp Pro Trp Ile Gln Val Thr Val Gly
        210                 215                 220 tgagacaaat ccatttccca aattatcaga atcattatag aagtaggtta gggagaattg     1272
gctgtgattc tttctcatgg ttaaaatgtg atttagttca gaattaacat ggttggaaac     1332
tctaaaaaat gtggaaaaca ggaacattct atgtctgaaa atctgaaaat agcatcaaga     1392
tgaaaacatt ctttagtcat aaatatactc ttttaagtta tagtagagaa aaagatctta     1452
tcatttcata agtggacttt tgggatagca ttggaaatgt aaatgaaata aatacctaat     1512 tgaaaaagt  ttattctaaa gtgttaatat ttagcaacag attcagagac aagaaagtaa     1572
caattcaatc tgtgtatttt ttgtgagaaa tagtttccca tgtgcaaata taaagtgcgc     1632
atcatatcat gataatatcc aactgtctgc agaactccct ttcataaatg agagaatttt     1692
aattcatagt gccttatatc ctcatcagcc atctgacttt actacagaag aaaacaatga     1752
aatgatgcat taagtgcttt gctagaagaa acatcatagc aaagctgata gcccacattc     1812
tgtgcannna agcttccaga gcactcgaga aaaagcagaa atgagatgtt ttatgaaaac     1872
cgaaaagata atctgatttc tgtgaaatat acttttgatc atgtggttct ttaagatagt     1932
```

-continued

```
cactaacaag tcattagtag cagataccaa atgggagaaa atttccagta tactgagggt    1992
caaggcagtc atgctgaaac tacatgaggt caggaaagtt ttgaaataag gtgattttgg    2052
aaggatacct tcaactggcc tagattttca agaaacagtg taatcaacag ccaaacatga    2112
gaatctagct aacagcattt agaaaaccag aactaagagt gttactgggg aattgcattt    2172
aaatccagta tgagagtttg caatgccgt attcttctaa ggggtttgtg ccacattttg     2232
ttaccatgga gtcctctgta agaactttat tagataaatc atctttacac tataatttga    2292
ataaaagccg gaattc                                                    2308
```

<210> SEQ ID NO 29
<211> LENGTH: 221
<212> TYPE: PRT
<213> ORGANISM: mus sp.

<400> SEQUENCE: 29

Met Lys His Leu Val Ala Ala Trp Leu Leu Val Gly Leu Ser Leu Gly
1               5                   10                  15

Val Pro Gln Phe Gly Lys Gly Asp Ile Cys Asn Pro Asn Pro Cys Glu
            20                  25                  30

Asn Gly Gly Ile Cys Leu Ser Gly Leu Ala Asp Asp Ser Phe Ser Cys
        35                  40                  45

Glu Cys Pro Glu Gly Phe Ala Gly Pro Asn Cys Ser Ser Val Val Glu
    50                  55                  60

Val Ala Ser Asp Glu Glu Lys Pro Thr Ser Ala Gly Pro Cys Ile Pro
65                  70                  75                  80

Asn Pro Cys His Asn Gly Gly Thr Cys Glu Ile Ser Glu Ala Tyr Arg
                85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Ala Glu Pro Cys
        115                 120                 125

Arg Asn Gly Gly Ile Cys Thr Asp Leu Val Ala Asn Tyr Ser Cys Glu
130                 135                 140

Cys Pro Gly Glu Phe Met Gly Arg Asn Cys Gln Tyr Lys Cys Ser Gly
145                 150                 155                 160

His Leu Gly Ile Glu Gly Gly Ile Ile Ser Asn Gln Gln Ile Thr Ala
                165                 170                 175

Ser Ser Asn His Arg Ala Leu Phe Gly Leu Gln Lys Trp Tyr Pro Tyr
            180                 185                 190

Tyr Ala Arg Leu Asn Lys Lys Gly Leu Ile Asn Ala Trp Thr Ala Ala
        195                 200                 205

Glu Asn Asp Arg Trp Pro Trp Ile Gln Val Thr Val Gly
    210                 215                 220

<210> SEQ ID NO 30
<211> LENGTH: 481
<212> TYPE: PRT
<213> ORGANISM: homo sapiens
<220> FEATURE:
<221> NAME/KEY: SIGNAL
<222> LOCATION: (1)..(23)
<220> FEATURE:
<221> NAME/KEY: DOMAIN
<222> LOCATION: (26)..(59)
<223> OTHER INFORMATION: egf-1
<220> FEATURE:
<221> NAME/KEY: DOMAIN

```
<222> LOCATION: (78)..(116)
<223> OTHER INFORMATION: egf-2
<220> FEATURE:
<221> NAME/KEY: MISC_FEATURE
<222> LOCATION: (96)..(98)
<220> FEATURE:
<221> NAME/KEY: DOMAIN
<222> LOCATION: (123)..(154)
<223> OTHER INFORMATION: egf-3
<220> FEATURE:
<221> NAME/KEY: DOMAIN
<222> LOCATION: (158)..(315)
<223> OTHER INFORMATION: discoidin-1
<220> FEATURE:
<221> NAME/KEY: DOMAIN
<222> LOCATION: (320)..(477)
<223> OTHER INFORMATION: discoidin-2
<220> FEATURE:
<221> NAME/KEY: UNSURE
<222> LOCATION: (382)..(382)
<220> FEATURE:
<221> NAME/KEY: misc_feature
<222> LOCATION: (382)..(382)
<223> OTHER INFORMATION: Xaa can be any naturally occurring amino acid
<220> FEATURE:
<221> NAME/KEY: UNSURE
<222> LOCATION: (400)..(400)
<220> FEATURE:
<221> NAME/KEY: misc_feature
<222> LOCATION: (400)..(400)
<223> OTHER INFORMATION: Xaa can be any naturally occurring amino acid
<220> FEATURE:
<221> NAME/KEY: UNSURE
<222> LOCATION: (423)..(423)
<220> FEATURE:
<221> NAME/KEY: misc_feature
<222> LOCATION: (423)..(423)
<223> OTHER INFORMATION: Xaa can be any naturally occurring amino acid
<220> FEATURE:
<221> NAME/KEY: UNSURE
<222> LOCATION: (434)..(434)
<220> FEATURE:
<221> NAME/KEY: misc_feature
<222> LOCATION: (434)..(434)
<223> OTHER INFORMATION: Xaa can be any naturally occurring amino acid

<400> SEQUENCE: 30

Met Lys Arg Ser Val Ala Val Trp Leu Leu Val Gly Leu Ser Leu Gly
1               5                  10                  15

Val Pro Gln Phe Gly Lys Gly Asp Ile Cys Asp Pro Asn Pro Cys Glu
            20                  25                  30

Asn Gly Gly Ile Cys Leu Pro Gly Leu Ala Val Gly Ser Phe Ser Cys
        35                  40                  45

Glu Cys Pro Asp Gly Phe Thr Asp Pro Asn Cys Ser Ser Val Val Glu
    50                  55                  60

Val Ala Ser Asp Glu Glu Glu Pro Thr Ser Ala Gly Pro Cys Thr Pro
65                  70                  75                  80

Asn Pro Cys His Asn Gly Gly Thr Cys Glu Ile Ser Glu Ala Tyr Arg
                85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Val Glu Pro Cys
        115                 120                 125

Lys Asn Gly Gly Ile Cys Thr Asp Leu Val Ala Asn Tyr Ser Cys Glu
    130                 135                 140

Cys Pro Gly Glu Phe Met Gly Arg Asn Cys Gln Tyr Lys Cys Ser Gly
145                 150                 155                 160

Pro Leu Gly Ile Glu Gly Gly Ile Ile Ser Asn Gln Gln Ile Thr Ala
```

```
                        165                 170                 175
Ser Ser Thr His Arg Ala Leu Phe Gly Leu Gln Lys Trp Tyr Pro Tyr
            180                 185                 190

Tyr Ala Arg Leu Asn Lys Lys Gly Leu Ile Asn Ala Trp Thr Ala Ala
                195                 200                 205

Glu Asn Asp Arg Trp Asn Arg Trp Ile Gln Ile Asn Leu Gln Arg Lys
        210                 215                 220

Met Arg Val Thr Gly Val Ile Thr Gln Gly Ala Lys Arg Ile Gly Ser
225                 230                 235                 240

Pro Glu Tyr Ile Lys Phe Tyr Lys Ile Ala Tyr Ser Asn Asp Gly Lys
                    245                 250                 255

Thr Trp Ala Met Tyr Lys Val Lys Gly Thr Asn Glu Asp Met Val Phe
                260                 265                 270

Arg Gly Asn Ile Asp Asn Asn Thr Pro Tyr Ala Asn Ser Phe Thr Pro
            275                 280                 285

Pro Ile Lys Ala Gln Tyr Val Arg Leu Tyr Pro Gln Val Cys Arg Arg
        290                 295                 300

His Cys Thr Leu Arg Met Glu Leu Leu Gly Cys Glu Leu Ser Gly Cys
305                 310                 315                 320

Ser Glu Pro Leu Gly Met Lys Ser Gly His Ile Gln Asp Tyr Gln Ile
                    325                 330                 335

Thr Ala Ser Ser Ile Phe Arg Thr Leu Asn Met Asp Met Phe Thr Trp
                340                 345                 350

Glu Pro Arg Lys Ala Arg Leu Asp Lys Gln Gly Lys Val Asn Ala Trp
            355                 360                 365

Thr Ser Gly His Asn Asp Gln Ser Gln Trp Leu Gln Val Xaa Leu Leu
        370                 375                 380

Val Pro Thr Lys Val Thr Gly Ile Ile Thr Gln Gly Ala Lys Asp Xaa
385                 390                 395                 400

Gly His Val Gln Phe Val Gly Ser Tyr Lys Leu Ala Tyr Ser Asn Asp
                    405                 410                 415

Gly Glu His Trp Thr Val Xaa Gln Asp Glu Lys Gln Arg Lys Asp Lys
                420                 425                 430

Val Xaa Gln Gly Asn Phe Asp Asn Asp Thr His Arg Lys Asn Val Ile
        435                 440                 445

Asp Pro Pro Ile Tyr Ala Arg His Ile Arg Ile Leu Pro Trp Ser Trp
    450                 455                 460

Tyr Gly Arg Ile Thr Leu Ala Ser Glu Leu Leu Gly Cys Thr Glu Glu
465                 470                 475                 480

Glu

<210> SEQ ID NO 31
<211> LENGTH: 103
<212> TYPE: PRT
<213> ORGANISM: homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 31

Xaa Asp Ile Cys Asp Pro Asn Pro Cys Glu Asn Gly Gly Ile Cys Leu
1               5                   10                  15

Pro Gly Leu Ala Val Gly Ser Phe Ser Cys Glu Cys Pro Asp Gly Phe
            20                  25                  30
```

```
Thr Asp Pro Asn Cys Ser Ser Val Val Glu Val Gly Pro Cys Thr Pro
         35                  40                  45

Asn Pro Cys His Asn Gly Gly Thr Cys Glu Ile Ser Glu Ala Tyr Arg
     50                  55                  60

Gly Asp Thr Phe Ile Gly Tyr Val Cys Lys Cys Pro Arg Gly Phe Asn
 65              70                  75                      80

Gly Ile His Cys Gln His Asn Ile Asn Glu Cys Glu Val Glu Pro Cys
                 85                  90                  95

Lys Asn Gly Gly Ile Cys Thr
            100

<210> SEQ ID NO 32
<211> LENGTH: 19
<212> TYPE: DNA
<213> ORGANISM: artificial sequence
<220> FEATURE:
<223> OTHER INFORMATION: 5' RT-PCR Primer

<400> SEQUENCE: 32
acccaagggg caaaaagga                                              19

<210> SEQ ID NO 33
<211> LENGTH: 19
<212> TYPE: DNA
<213> ORGANISM: artificial sequence
<220> FEATURE:
<223> OTHER INFORMATION: minus strand RT-PCR primer

<400> SEQUENCE: 33
cctgtaacca ttgtgactg                                              19
```